(12) United States Patent
Vankayalapati et al.

(10) Patent No.: US 10,266,536 B2
(45) Date of Patent: *Apr. 23, 2019

(54) METHODS AND COMPOSITIONS FOR INHIBITION OF BROMODOMAIN-CONTAINING PROTEINS

(71) Applicant: ConverGene LLC, Cambridge, MD (US)

(72) Inventors: Hariprasad Vankayalapati, Draper, UT (US); Makoto Yoshioka, Gaithersburg, MD (US); Jeffrey W. Strovel, Cambridge, MD (US); Janak Khimchand Padia, Germantown, MD (US)

(73) Assignee: ConverGene LLC, Cambridge, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/634,768

(22) Filed: Jun. 27, 2017

(65) Prior Publication Data

US 2018/0134715 A1 May 17, 2018

Related U.S. Application Data

(63) Continuation of application No. 14/774,387, filed as application No. PCT/US2014/025289 on Mar. 13, 2014, now Pat. No. 9,695,179.

(60) Provisional application No. 61/781,988, filed on Mar. 14, 2013.

(51) Int. Cl.

| | | |
|---|---|---|
| C07D 487/04 | (2006.01) |
| C07C 217/84 | (2006.01) |
| C07D 261/08 | (2006.01) |
| C07D 215/22 | (2006.01) |
| C07D 215/38 | (2006.01) |
| C07D 265/22 | (2006.01) |
| C07D 409/14 | (2006.01) |
| C07D 471/04 | (2006.01) |
| C07D 413/04 | (2006.01) |
| C07D 401/14 | (2006.01) |
| C07D 265/26 | (2006.01) |
| C07D 405/06 | (2006.01) |
| C07D 405/04 | (2006.01) |
| C07D 401/12 | (2006.01) |
| C07D 401/04 | (2006.01) |
| C07D 215/227 | (2006.01) |
| C07D 413/14 | (2006.01) |
| C07D 409/06 | (2006.01) |

(52) U.S. Cl.
CPC .......... *C07D 487/04* (2013.01); *C07C 217/84* (2013.01); *C07D 215/22* (2013.01); *C07D 215/227* (2013.01); *C07D 215/38* (2013.01); *C07D 261/08* (2013.01); *C07D 265/22* (2013.01); *C07D 265/26* (2013.01); *C07D 401/04* (2013.01); *C07D 401/12* (2013.01); *C07D 401/14* (2013.01); *C07D 405/04* (2013.01); *C07D 405/06* (2013.01); *C07D 409/06* (2013.01); *C07D 409/14* (2013.01); *C07D 413/04* (2013.01); *C07D 413/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 3,755,332 A | 8/1973 | Wasley |
| 9,695,179 B2 | 7/2017 | Vankayalapati et al. |
| 2010/0286127 A1 | 11/2010 | Miyoshi et al. |
| 2012/0157428 A1 | 6/2012 | Albrecht et al. |
| 2012/0220573 A1 | 8/2012 | Gosmini et al. |
| 2012/0252781 A1 | 10/2012 | Bailey et al. |

FOREIGN PATENT DOCUMENTS

| | | |
|---|---|---|
| CN | 101910182 | 12/2010 |
| CN | 102762569 | 10/2012 |
| CN | 102781943 | 11/2012 |
| EP | 0393926 | 10/1990 |
| EP | 1012166 | 10/2003 |
| EP | 1430030 | 5/2005 |
| EP | 1854789 | 11/2007 |
| EP | 2072502 | 6/2009 |
| EP | 2221301 | 8/2010 |
| EP | 2650286 | 10/2013 |
| EP | 1865958 | 7/2015 |
| EP | 3056207 | 8/2016 |
| FR | 1 369 627 | 8/1964 |
| WO | WO 93/03030 | 2/1993 |
| WO | WO 03/106452 | 12/2003 |
| WO | WO 2006/121767 | 11/2006 |
| WO | WO 2007/109251 | 9/2007 |

(Continued)

OTHER PUBLICATIONS

Abel et al., "Epigenetic targets of HDAC inhibition in neurodegenerative and psychiatric disorders," Curr Opin Pharmacol., 8(1):57-64 (2008).

(Continued)

*Primary Examiner* — Brian J Davis
(74) *Attorney, Agent, or Firm* — Fish & Richardson P.C.

(57) ABSTRACT

The present invention relates to compounds that bind to and otherwise modulate the activity of bromodomain-containing proteins, to processes for preparing these compounds, to pharmaceutical compositions containing these compounds, and to methods of using these compounds for treating a wide variety of conditions and disorders.

29 Claims, No Drawings

(56) References Cited

FOREIGN PATENT DOCUMENTS

| WO | WO 2008/054599 | 5/2008 |
|---|---|---|
| WO | WO 2008/117079 | 10/2008 |
| WO | WO 2011/054844 | 5/2011 |
| WO | WO 2011/054846 | 5/2011 |
| WO | WO 2011/054848 | 5/2011 |
| WO | WO 2008/141843 | 11/2011 |
| WO | WO 2011/140442 | 11/2011 |
| WO | WO 2012/040499 | 3/2012 |
| WO | WO 2012/125913 | 9/2012 |
| WO | WO 2012/143416 | 10/2012 |
| WO | WO 2013/003586 | 1/2013 |
| WO | WO 2013/027168 | 2/2013 |
| WO | WO 2014/089546 | 6/2014 |
| WO | WO 2015/015318 | 5/2015 |
| WO | WO 2016/077656 | 5/2016 |
| WO | WO 2016/120808 | 8/2016 |

OTHER PUBLICATIONS

Abouzid K et al. "Design, synthesis and in vitro antitumor activity of 4-aminoquinoline and 4-aminoquinazoline derivatives targeting EGFR tyrosine kinase", Bioorganic & Medicinal Chemistry, Pergamon, Gb, Aug. 2008, vol. 16, 16:7543-7551.
Andreae et al., "Electrophile Aminierung von C-H-aciden Verbindungen mit 1-Oxa-2-azaspiro [ 2.51 octan," European Journal of European Chemistry, Mar. 1992, 1992(3): 239-256.
Bhavin Marvania et al: "The synthesis and biological evaluation of new DNA-directed alkylating agents, phenyl N-mustard-4-anilinoquinoline conjugates containing a urea linker" European Journal of Medicinal Chemistry., Aug. 1, 2014, 83:695-708.
Chemical Abstract compound, STN express. RN 1136445-44-7 (Entered STN: Apr. 19, 2009).
Chemical Abstract compounds, STN express. RN 792868-63-4 (Entered STN: Dec. 6, 2004) and RN 765232-57-3 (Entered STN: Oct. 18, 2004).
Chinese Office Action in Chinese Application No. 201480028551.7, dated Jan. 25, 2017, 16 pages (English Translation).
Chung et al., "Progress in the discovery of small-molecule inhibitors of bromodomain-histone interactions," J Biomol Screen., 16(10):1170-85 (2011).
Database CAPLUS in STN, Acc. No. 1964:16656, FR M1580 (Dec. 17, 1962) (abstract).
Delmore et al., "BET bromodomain inhibition as a therapeutic strategy to target c-Myc," Cell., 146(6):904-17 (2011).
Denis et al., "An emerging role for bromodomain-containing proteins in chromatin regulation and transcriptional control of adipogenesis," FEBS Lett., 584(15):3260-8 (2010).
Denis, "Bromodomain coactivators in cancer, obesity, type 2 diabetes, and inflammation," Discov Med., 10(55):489-99 (2010).
European Search Report in European Application No. 14776141.5, dated Feb. 6, 2017, 24 pages.
Farhanullah et al., "Design and synthesis of quinolinones as methionyl-tRNA synthetase inhibitors", Bioorganic & Medicinal Chemistry, 2006, vol. 14, pp. 7154-7159 See abstract; and p. 7157.
Filippakopoulos et al., "Selective inhibition of BET bromodomains," Nature., 468(7327):1067-73 (2010).
Florence et al., "You bet-cha: a novel family of transcriptional regulators," Front Biosci., 6:D1008-18 (2001).
Furdas et al., "Inhibition of bromodomain-mediated protein-protein interactions as a novel therapeutic strategy," Med Chem Commun., 3:123-134 (2012).
Gao et al. "Identification of Essential Residues Involved in the Allosteric Modulation of the Human A3 Adenosine Receptor", Molecular Pharmacology, vol. 63, No. 5, 1 May 1, 2003, pp. 1021-1031.
International Preliminary Report on Patentability and Written Opinion in International Application No. PCT/US2015/060494, dated May 16, 2017, 10 pages.

International Preliminary Report on Patentability in International Application No. PCT/US2014/025289, dated Sep. 15, 2015, 8 pages.
International Search Report and Written Opinion in International Application No. PCT/US2014/025289, dated Aug. 26, 2014, 11 pages.
International Search Report and Written Opinion in International Application No. PCT/US2015/060494, dated Jun. 30, 2016, 13 pages.
International Search Report and Written Opinion in International Application No. PCT/US2016/063485, dated Jan. 24, 2017, 11 pages.
McPhillips et al., "Interaction of bovine papillomavirus E2 protein with Brd4 stabilizes its association with chromatin," J Virol., 79(14):8920-32 (2005).
Mertz et al., "Targeting MYC dependence in cancer by inhibiting BET bromodomains," Proc Natl Acad Sci U.S.A., 108(40):16669-74 (2011).
Moyer et al. "The Synthesis and Identification of 4,6-Diaminoquinoline Derivatives as Potent Immunostimulants", Bioorganic & Medicinal Chemisty Letters, Pergamon, Amsterdam, Nl, Jan. 1, 1992, vol. 2, No. 12:1589-1594.
Sahai et al., "BET Bromodomain Inhibitors Block Growth of Pancreatic Cancer Cells in Three-Dimensional Collagen" Mol Cancer Ther, May 7, 2014: 13(7): 1907-17.
Puissant et al., "Targeting MYCN in neuroblastoma by BET bromodomain inhibition," Cancer Discov., 3(3):308-23 (2013).
Sanchez et al., "The role of human bromodomains in chromatin biology and gene transcription," Curr Opin Drug Discov Devel., 12(5):659-65 (2009).
Stilling et al. "The role of histone acetylation in age-associated memory impairment an Alzheimer's disease," Neurobiology of Learning and memory, 2011, 96:19-26.
Shu et al., "Response and resistance to BET bromodomain inhibitors in triple negative breat cancer" Nature. Jan. 21, 2016; 529(7586): 413-417.
Shimamura et al., "Efficacy of BET bromodomain inhibition in Kras-mutant non-small cell lung cancer," Clin Cancer Res. Nov. 15, 2013; 19(22).
Seal et al., "Identificafion of a novel series of BET family brmodomain inhibitors: Binding mode and profile of I-BET151 (GSK1210151A)," Bioorganic & Medicinal Chemistry Letters, Apr. 2012, 22(8): 2968-2972.
Stuhlmiller et al. "Inhibition of Lapatinib-lnduced Kinome Reprogramming in ERBB2-Ppsitive Breast Cancer by Targeting BET Family Bromodomains", Cell Reports, Apr. 1, 2015, vol. 11, 3:390-404.
Tamkun et al., "brahma: a regulator of Drosophila homeotic genes structurally related to the yeast transcriptional activator SNF2/SWI2," Cell., 68(3):561-72 (1992).
Tiwari, Abhishek et al., "Synthesis of new pyrazolidine 3,5 dione 1-3,7,8 derivatives of potential analgesic, antipyretic and anti-inflammatory activities", Middle-East Journal of Scientific Research, 2013, Vo 1, 17, No. 7, pp. 926-993 See abstract; p. 927; and Fig. 1.
Ukrainets et al., "4-Hydroxy-2-quinolones. 92. Reaction of 1-R-4-chloro-3-ethoxycarbonyl-2-oxo-1,2-dihydroquinolines with anilines," Chemistry of Hetercyclic Compounds, Mar. 2006, 42(3): 343-351.
Ukrainets, I. V. et al., "4-Hydroxy-2-Quinolones. 192.* Relationship of Structure and Analgesic Activity of 4-Amino-2-0X0-1,2-Dihydroquinoline-3-Carboxylic Acids and Their Derivatives", Chemistry of Heterocyclic Compounds, Feb. 2011, vol. 46, No. 11, pp. 1371-1379 (Russian Original vol. 46, No. 1, Nov. 2010) See Abstract; and p. 1372.
Ukrainets, I. V. et al., "4-Hydroxyquinol-2-0Nes. 87*. Unusual Synthesis of 1-R-4-Hydroxy-2-0X0-1,2-Dihydroquinoline-3-Carboxylic Acid Pyridylamides", Chemistry of Heterocyclic Compounds, 2005, vol. 41, No. 9, pp. 1158 1166 See abstract; and p. 1159.
Wu et al., "The double bromodomain-containing chromatin adaptor Brd4 and transcriptional regulation," J Biol Chem., 282(18):13141-5 (2007).
Yang et al. "Synthesis, in vitro and in vivo evaluation of 3-arylisoquinolinamines as potent antitumor agents", Bioorganic &

(56) References Cited

OTHER PUBLICATIONS

Medicinal Chemistry Letters, Pergamon, Amsterdam. Nl, vol. 20, No. 17, Sep. 1, 2010 pp. 5277-5281.
You et al., "Kaposi's sarcoma-associated herpesvirus latency-associated nuclear antigen interacts with bromodomain protein Brd4 on host mitotic chromosomes," J Virol., 80(18):8909-19 (2006).
Yuan et al., "Enhanced homology searching through genome reading frame predetermination," Bioinformatics., 20(9):1416-27 (2004).
Wyce et al., "Abstract 382: Inhibition of BET bromodomain proteins as a therapeutic approach in prostate cancer," Oncotarget, December, vol. 4, No. 12: 2419-2429, 2013.

METHODS AND COMPOSITIONS FOR INHIBITION OF BROMODOMAIN-CONTAINING PROTEINS

CROSS-REFERENCE TO RELATED APPLICATION

This is a continuation of U.S. patent application Ser. No. 14/774,387, filed Sep. 10, 2015, which is a 35 U.S.C. § 371 National Stage Application of International Application No. PCT/US2014/025289, filed Mar. 13, 2014, which claims priority to U.S. Provisional Application No. 61/781,988, filed on Mar. 14, 2013, the disclosure of each of which is incorporated herein by reference in its entirety.

FIELD OF THE INVENTION

The present invention relates to compounds that inhibit bromodomain-containing proteins from binding acetylated proteins, to processes for preparing these compounds, to pharmaceutical compositions containing these compounds, and to methods of using these compounds for treating a wide variety of conditions and disorders.

BACKGROUND OF THE INVENTION

Epigenetic chromatin remodeling is a central mechanism for the regulation of gene expression. Pharmacological modulation of epigenetic change represents a new mode of therapeutic interventions for cancer and inflammation. Emerging evidence suggests that such epigenetic modulations may also provide therapeutic means for obesity, as well as metabolic, cardiovascular, neurodegenerative, psychiatric and infectious diseases.

The eukaryotic genome is organized into a basic packaging unit called a nucleosome, which is comprised of approximately 147 base pairs of double-stranded DNA helix wound around a histone octamer, which, in turn, consists of two subunits each of H2A, H2B, H3, and H4 proteins. Nucleosomes are further packaged into chromatin structures, which can exist in a relatively loose state of euchromatin or in a tightly packed heterochromatin structure. Transition from heterochromatin to euchromatin allows transcription of genes, although not all of the genes in euchromatin structure are transcribed. This transition from heterochromatin to euchromatin is controlled by post-translational modifications of histone proteins, including acetylation of lysine residues in H3/H4 proteins. Histone acetylation is catalyzed by histone acetyltransferases (HATs), resulting in open euchromatin structures that allow transcription of genes including tumor suppressor genes. Conversely, histone deacetylation leads to suppression of such genes and this activity is catalyzed by histone deacetylases (HDACs). Inhibition of histone deacetylases is a mode of cancer treatment and vorinostat (Zolinza®), a histone deacetylase inhibitor, has been shown to be an effective drug for cutaneous T-cell lymphoma in humans.

Histone acetylation also is monitored by bromodomain-containing proteins. Bromodomains are approximately 110 amino acid-long evolutionary conserved modules that bind to acetyllysine residues of acetylated proteins and are present in a number of chromatin-associated proteins including HATs. Bromodomains were first identified as a motif in *Drosophila* Brahma from which the name was derived but are also found in proteins in humans and yeast either as single-copy or contiguously repeated domains, and are thought to confer specificity for the complex pattern of epigenetic modifications known as the histone code (Cell. 1992 Feb. 7; 68(3):561-72; J Biomol Screen. 2011 December; 16(10):1170-85). The human genome encodes approximately 50 bromodomain-containing proteins (Bioinformatics. 2004 Jun. 12; 20(9):1416-27), some of which may be involved in etiology of cancer, inflammation, obesity, metabolic, cardiovascular, neurodegenerative, psychiatric and infectious diseases (Med Chem Commun. 2012 Jan. 4 3(2):123-134; Curr Opin Drug Discov Devel. 2009 September; 12(5):659-65; Discov Med. 2010 December; 10(55): 489-99; FEBS Lett. 2010 Aug. 4; 584(15):3260-8; J Virol. 2006 September; 80(18):8909-19; J Virol. 2005 July; 79(14):8920-32; Curr Opin Pharmacol. 2008 February; 8(1): 57-64). Thus, inhibition and/or modulation of bromodomain-containing proteins may present a new mode of pharmacological intervention for such diseases. For example, inhibition of bromodomain and extra-terminal domain (BET) family of proteins, which play a key role in controlling cell fate and cell cycle progression by recruiting transcriptional regulators to specific genomic locations (Front Biosci. 2001 Aug. 1; 6:D1008-18; J Biol Chem. 2007 May 4; 282(18):13141-5), is of particular interest as a treatment for cancer. Inhibition of the BET family of proteins was shown to be effective in rodent models for human NUT midline carcinoma, multiple myeloma, Burkitt's lymphoma and acute myeloid leukemia by indirectly reducing the expression of a proto-oncogene MYC (Nature. 2010 Dec. 23; 468(7327):1067-73; Cell. 2011 Sep. 16; 146(6):904-1; Proc Natl Acad Sci USA. 2011 Oct. 4; 108(40):16669-74). Bromodomain-containing proteins bind to acetyllysine residues of proteins including acetylated histones as well as acetylated non-histone proteins, such as transcription factors and the HIV-1 Tat protein.

Of approximately 50 bromodomain-containing proteins encoded by human genome, BET proteins represent a small protein family that includes BRD2, BRD3, BRD4 and BRDT and contains two tandem bromodomains and an extraterminal domain (J Biol Chem. 2007 May 4; 282(18): 13141-5). BET proteins bind to acetylated nucleosomes and are thought to function by opening chromatin structure and/or by facilitating transcriptional initiation (Front Biosci. 2001 Aug. 1; 6:D1008-18). Inhibition of BET proteins was shown to be an effective mode of intervention in rodent models of human NUT midline carcinoma, multiple myeloma, Burkitt's lymphoma and acute myeloid leukemia by suppressing the expression of MYC gene (Nature. 2010 Dec. 23; 468(7327):1067-73; Cell. 2011 Sep. 16; 146(6): 904-1; Proc Natl Acad Sci USA. 2011 Oct. 4; 108(40): 16669-74), as well as MYCN gene (Cancer Discov. 2013 March: 3(3) 308-23). MYC and homologous genes are some of the most overexpressed genes in human cancers; however, there has not been a pharmaceutical compound that directly antagonizes the activity of proteins encoded by the genes to date partly due to the lack of effective drug binding sites.

Thus, there exists a need for a means of indirect suppression of the expression of the MYC and homologous genes by inhibiting bromodomains of BET proteins which provide an effective mode of treatment for various diseases and conditions, including various cancers.

SUMMARY OF THE INVENTION

The present invention includes compounds which bind to and otherwise modulate acetylated protein binding to bromodomain-containing proteins. The present invention also relates to pharmaceutically acceptable salts prepared from these compounds.

According to one aspect, the present invention includes a compound as represented by Formula I:

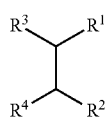

Formula I wherein:

R¹ and R² are independently —H, C₁-C₆ alkyl optionally substituted with halo or alkoxy, or C₂-C₆ alkene optionally substituted with halo or alkoxy; or R¹ and R² form a six-membered aryl or heteroaryl ring optionally substituted with halo, alkyl, alkoxy, aryl, —S(O)₂—R⁶, —NH—(R⁵)—(R⁶), S(O)₂—NR⁵—R⁶, C(O)₂—NR⁵—R⁶, heterocycle, or heteroaryl ring, the heterocycle and heteroaryl having one to three heteroatoms independently selected from the group consisting of oxygen, nitrogen and sulfur, wherein the heterocycle and heteroaryl are optionally substituted with one or more hydroxyl, alkyl, alkoxy, amido, sulfamido, halo, or —C(O)₂-alkyl, wherein R⁵ is —C(O)— or —S(O)₂—, and wherein R⁶ is one or more —H, alkyl, C₂-C₆ alkene, cycloalkyl, aryl, heterocycle, or heteroaryl ring, the heterocycle or heteroaryl having one to three heteroatoms independently selected from the group consisting of oxygen, nitrogen and sulfur, and wherein each C₂-C₆ alkene, cycloalkyl, aryl, heterocycle, or heteroaryl is optionally substituted with hydroxyl, sulfhydryl, CN, CF₃, NO₂, halo, alkyl, aryl, alkoxy, carboxyamido, sulfamido, or mono or dialkylsubstituted amine;

R³ and R⁴ are independently

C₁-C₇ alkyl optionally substituted with hydroxyl, heterocycle, or heteroaryl, the heterocycle and heteroaryl having one to three heteroatoms independently selected from the group consisting of oxygen, nitrogen and sulfur, wherein the heterocycle and heteroaryl are optionally substituted with one or more substituents selected from hydroxyl, sulfhydryl, CN, CF₃, NO₂, halo, alkyl, aryl, alkoxy, carboxyamido, sulfamido, or mono or dialkylsubstituted amine;

C₂-C₇ alkene optionally substituted with hydroxyl, heterocycle, or heteroaryl, the heterocycle and heteroaryl having one to three heteroatoms independently selected from the group consisting of oxygen, nitrogen and sulfur, wherein the heterocycle and heteroaryl are optionally substituted with one or more substituents selected from hydroxyl, sulfhydryl, CN, CF₃, NO₂, halo, alkyl, aryl, alkoxy, carboxyamido, sulfamido, or mono or dialkylsubstituted amine;

—NC(O)R⁷, wherein R⁷ is C₁-C₇ alkyl or C₂-C₇ alkene; or

R³ and R⁴ form a ring (i), (ii), (iii), (iv), (v), or (vi)

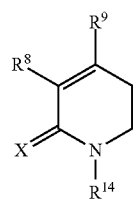

(i)

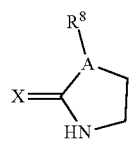

(ii)

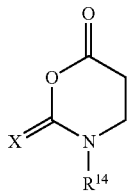

(iii)

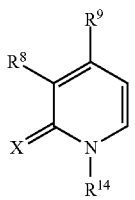

(iv)

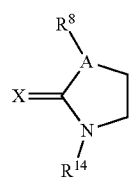

(v)

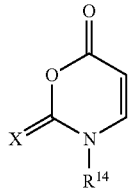

(vi)

wherein,
A is N or CH;
X is O, S or NH;
R⁸ is
halo;
C₁-C₆ alkyl optionally substituted with aryl, heterocycle, or heteroaryl, the heterocycle and heteroaryl having one to three heteroatoms independently selected from the group consisting of oxygen, nitrogen and sulfur, wherein the heterocycle and heteroaryl are optionally substituted with one or more substituents selected from hydroxyl, sulfhydryl, CN, CF₃, NO₂, halo, alkyl, aryl, alkoxy, carboxyamido, sulfamido, or mono or dialkylsubstituted amine;
C₂-C₆ alkene optionally substituted with aryl, heterocycle, or heteroaryl, the heterocycle and heteroaryl having one to three heteroatoms independently selected from the group consisting of oxygen, nitrogen and sulfur, wherein the heterocycle and heteroaryl are optionally substituted with one or more substituents selected from hydroxyl, sulfhydryl, CN, $CF_3$, $NO_2$, halo, alkyl, aryl, alkoxy, carboxyamido, sulfamido, or mono or dialkylsubstituted amine;

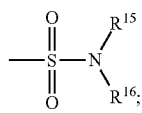

wherein $R^{15}$ and $R^{16}$ are alkyl or cycloalkyl or heterocycle, or $R^{15}$ and $R^{16}$ can form a heterocycle;
—C(O)—$R^{17}$, wherein $R^{17}$ is alkyl, cycloalkyl or heterocycle;
—S—$R^{18}$, wherein $R^{18}$ is alkyl, aryl, or cycloalkyl;
—S—C(O)—N($R^{15}R^{16}$);
a five-membered heterocycle or heteroaryl having one to three heteroatoms independently selected from the group consisting of oxygen, nitrogen and sulfur, wherein the five-membered heterocycle and heteroaryl are optionally substituted with one or more halo, alkyl, alkoxy, sulfur, heterocycle or heteroaryl ring, or one or more of $R^1$, $R^2$, $R^3$ or $R^4$ groups;

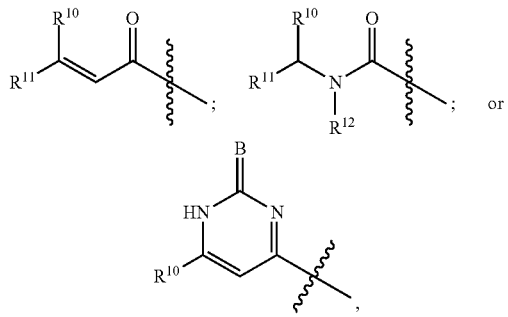

wherein B is O, S, or NH,
wherein $R^{10}$ and $R^{11}$ are independently —H; alkyl; aryl; heterocycle; heterocyclyl; or heteroaryl, the heterocycle, heterocyclyl, and heteroaryl having one to three heteroatoms independently selected from the group consisting of oxygen, nitrogen and sulfur, wherein the aryl, heterocycle, heterocyclyl, and heteroaryl are optionally substituted with one or more hydroxyl, sulfhydryl, CN, $CF_3$, $NO_2$, halo, alkyl, aryl, alkoxy, carboxyamido, sulfamido, or mono or dialkylsubstituted amine, and
wherein $R^{12}$ is —H or alkyl;
$R^9$ is H; OH; aryl; heterocycle; heteroaryl; —$SO_2$—NH—Z; —NH—Z; or —O—$SO_2$—$R^{13}$,
wherein the heterocycle and heteroaryl have one to three heteroatoms independently selected from the group consisting of oxygen, nitrogen and sulfur, and wherein the heterocycle and heteroaryl are optionally substituted with one or more hydroxyl, sulfhydryl, CN, $CF_3$, $NO_2$, halo, alkyl, aryl, alkoxy, carboxyamido, sulfamido, mono or dialkylsubstituted amine,
wherein $R^{13}$ is heterocycle or heteroaryl, the heterocycle and heteroaryl optionally substituted with one or more hydroxyl, sulfhydryl, CN, $CF_3$, $NO_2$, halo, alkyl, aryl, alkoxy, carboxyamido, sulfamido, mono or dialkylsubstituted amine, or $R^8$, and wherein Z is alkyl, heteroaryl, or aryl, wherein the alkyl, heteroaryl, or aryl is optionally substituted with one or more hydroxyl, sulfhydryl, CN, $CF_3$, $NO_2$, halo, alkyl, aryl, alkoxy, carboxyamido, sulfamido, or mono or dialkylsubstituted amine; and $R^{14}$ is —H or $C_1$-$C_6$ alkyl optionally substituted with aryl, wherein the aryl is optionally substituted with one or more hydroxyl, sulfhydryl, CN, $CF_3$, $NO_2$, halo, alkyl, aryl, alkoxy, carboxyamido, sulfamido, or mono or dialkylsubstituted amine.

According to one embodiment, X is O. According to one embodiment, $R^8$ is

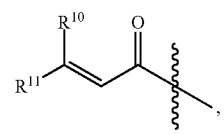

wherein $R^{10}$ and $R^{11}$ are independently —H; alkyl; aryl; or a five-membered or six-membered heterocycle, heterocyclyl, or heteroaryl having one to three heteroatoms independently selected from the group consisting of oxygen, nitrogen and sulfur, wherein the aryl, five-membered or six-membered heterocycle, heterocyclyl, or heteroaryl are optionally substituted with alkyl, halo, alkoxy, or —$N(CH_3)_2$.

According to an alternative embodiment, $R^8$ is

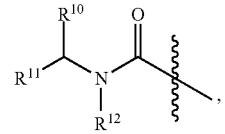

wherein $R^{10}$ and $R^{11}$ are independently —H; alkyl; aryl; or a five-membered or six-membered heterocycle, heterocyclyl, or heteroaryl having one to three heteroatoms independently selected from the group consisting of oxygen, nitrogen and sulfur, wherein the aryl, five-membered or six-membered heterocycle, heterocyclyl, or heteroaryl are optionally substituted with alkyl, halo, alkoxy, or —$N(CH_3)_2$, and wherein $R^{12}$ is H or alkyl.

According to another embodiment, $R^1$ and $R^2$ form a six-membered aryl ring, the six-membered aryl ring substituted with one or more hydroxyl, sulfhydryl, CN, $CF_3$, $NO_2$, halo, alkyl, aryl, alkoxy, carboxyamido, sulfamido, or mono or dialkylsubstituted amine, and wherein $R^3$ and $R^4$ form a ring (i). According to such an embodiment, $R^9$ may be —O—$SO_2$—$R^{13}$. According to yet another such embodiment, $R^8$ may be —S—$R^{18}$. According to yet another such embodiment, $R^8$ may be —S—C(O)—N($R^{15}R^{16}$).

According to one embodiment, $R^{11}$ is phenyl optionally substituted with one or more alkyl, halo, —$OCH_3$, or —$N(CH_3)_2$.

According to one embodiment, $R^9$ is —$SO_2$—NH—Z, —NH—Z, or —O—$SO_2$—$R^{13}$.

According to one embodiment, $R^1$ and $R^2$ form an optionally substituted six-membered aryl ring.

According to another aspect, compounds of Formula 1A, IB, IC and ID are provided,

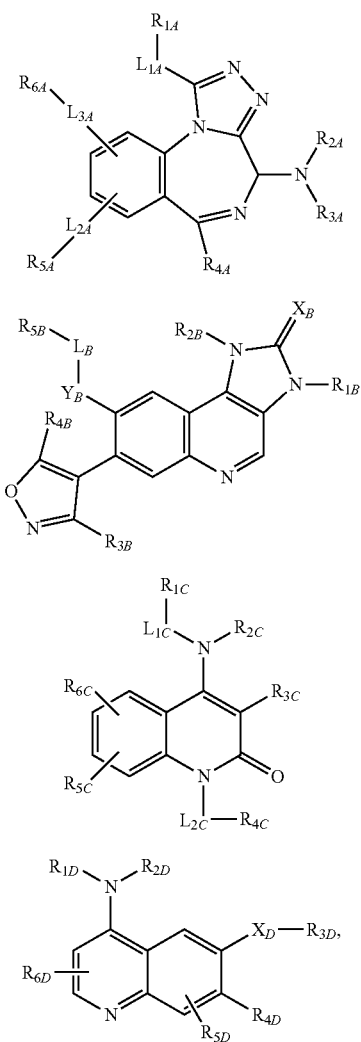

Formula 1A
Formula 1B
Formula 1C
Formula 1D including pharmaceutically acceptable salts and isomers thereof. According to such an embodiment, $R_{1A}$ is selected from alkyl, substituted or unsubstituted aryl, substituted or unsubstituted heteroaryl, substituted or unsubstituted cycloalkyl, and substituted or unsubstituted heterocycloalkyl including nitrogen, oxygen or sulfur as a heteroatom of the heterocycloalkyl, wherein said substitutions are selected from hydrogen, hydroxyl, sulfhydryl, alkoxy, thioalkoxy, alkyl, halogen, CN, $CF_3$, $NO_2$, $COOR_{7A}$, NC(O)$OR_{7A}$, $CONR_{7A}R_{8A}$, $NR_{7A}COR_{8A}$, $NR_{7A}SO_2R_{8A}$, $NR_{9A}CONR_{7A}R_{8A}$, and $NR_{7A}R_{8A}$, wherein $NR_{7A}R_{8A}$ optionally forms a substituted or unsubstituted mono or bicyclic ring having one to four heteroatoms selected from N, O and S, wherein said substitutions are selected from hydrogen, hydroxyl, sulfhydryl, alkoxy, thioalkoxy, alkyl and halogen;

wherein $R_{7A}$, $R_{8A}$ and $R_{9A}$ are each independently selected from hydrogen, alkyl, heteroalkyl, substituted or unsubstituted aryl, substituted or unsubstituted arylalkyl, substituted or unsubstituted heteroaryl, substituted or unsubstituted heteroarylalkyl, substituted or unsubstituted cycloalkyl, and substituted or unsubstituted heterocycloalkyl, wherein said substitutions are selected from hydrogen, hydroxyl, sulfhydryl, alkoxy, thioalkoxy, alkyl and halogen; or $R_{7A}$ and $R_{8A}$ optionally form a 4, 5, 6 or 7-member ring; $R_{2A}$ is hydrogen, alkyl, C(O)$OR_{7A}$, $CONR_{7A}R_{8A}$, $NR_{7A}R_{8A}$, $NR_{7A}COR_{8A}$, $NR_{7A}SO_2R_{8A}$, or $NR_{9A}CONR_{7A}R_{8A}$;

$R_{3A}$ is hydrogen or alkyl;

$R_{4A}$ is alkyl, substituted or unsubstituted aryl, substituted or unsubstituted heteroaryl, substituted or unsubstituted cycloalkyl, or substituted or unsubstituted heterocycloalkyl, wherein the heterocycloalkyl includes nitrogen, oxygen or sulfur as a heteroatom, wherein said substitutions are selected from hydrogen, hydroxyl, sulfhydryl, alkoxy, thioalkoxy, alkyl, halogen, CN, $CF_3$, $NO_2$, $COOR_{7A}$, NC(O)$OR_{7A}$, $CONR_{7A}R_{8A}$, $NR_{7A}R_{8A}$, $NR_{7A}COR_{8A}$, $NR_{7A}SO_2R_{8A}$, and $NR_{7A}CONR_{8A}R_{9A}$; and wherein $R_{7A}$, $R_{8A}$ and $R_{9A}$ are as defined above;

$R_{5A}$ and $R_{6A}$ are independently selected from hydrogen, alkyl, substituted or unsubstituted aryl, substituted or unsubstituted heteroaryl, substituted or unsubstituted cycloalkyl and substituted or unsubstituted heterocycloalkyl wherein the heteroatom is nitrogen, oxygen or sulfur, wherein said substitutions are selected from hydrogen, hydroxyl, sulfhydryl, alkoxy, thioalkoxy, alkyl, halogen, CN, $CF_3$, $NO_2$, $COOR_{7A}$, NC(O)$OR_{7A}$, $CONR_{7A}R_{8A}$, $NR_{7A}R_{8A}$, $NR_{7A}COR_{8A}$, $NR_{7A}SO_2R_{8A}$, $NR_{7A}CONR_{8A}R_{9A}$; and wherein $R_{7A}$, $R_{8A}$ and $R_{9A}$ are as defined above;

$L_{1A}$ is —(C—$R_{10A}R_{11A}$)$_{nA}$— wherein $R_{10A}$ and $R_{11A}$ are independently selected from hydrogen and alkyl and nA is 1, 2, or 3;

$L_{2A}$ and $L_{3A}$ are independently selected from —(C—$R_{10A}R_{11A}$)$_n$—, —CON($R_{7A}$)—, —$SO_2N(R_{7A})$—, —$R_{7A}CON(R_{8A})$— and —OCON($R_{7A}$); wherein n is 1, 2, or 3; provided when $L_{1A}$=0, and $L_{2A}$=0, $R_{1A}$ is a phenyl ring substituted with at least one methyl group, and $R_{2A}$ cannot be hydrogen.

$R_{1B}$ is selected from substituted or unsubstituted aryl, substituted or unsubstituted heteroaryl, substituted or unsubstituted cycloalkyl, and substituted or unsubstituted heterocycloalkyl wherein the heterocycloalkyl includes nitrogen, oxygen or sulfur as a heteroatom, wherein said substitutions are selected from hydrogen, hydroxyl, sulfhydryl, alkoxy, thioalkoxy, alkyl, halogen, CN, $CF_3$, $NO_2$, $COOR_{7B}$, NC(O)$OR_{7B}$, $CONR_{7B}R_{8B}$, $NR_{7B}R_{8B}$, $NR_{7B}COR_{8B}$, $NR_{7B}SO_2R_{8B}$, and $NR_{9B}CONR_{7B}R_{8B}$;

wherein $R_{7B}$, $R_{8B}$ and $R_{9B}$ are as each independently selected from hydrogen, alkyl, heteroalkyl, substituted or unsubstituted aryl, substituted or unsubstituted arylalkyl, substituted or unsubstituted heteroaryl, substituted or unsubstituted heteroarylalkyl, substituted or unsubstituted cycloalkyl, and substituted or unsubstituted heterocycloalkyl;

wherein $NR_{7B}R_{8B}$ optionally form a substituted or unsubstituted mono or bicyclic ring including one to four heteroatoms selected from N, O and S; and wherein $R_{7B}$ and $R_{8B}$ may form a 4, 5, 6 or 7-member ring; wherein said substitutions are selected from hydrogen, hydroxyl, sulfhydryl, alkoxy, thioalkoxy, alkyl and halogen;

$R_{2B}$ is selected from hydrogen, substituted or unsubstituted alkyl group, substituted or unsubstituted cycloalkyl and substituted or unsubstituted heterocycloalkyl, wherein the heterocycloalkyl heteroatom is nitrogen, oxygen or sulfur;

wherein said substitutions are selected from hydrogen, hydroxyl, sulfhydryl, alkoxy, thioalkoxy, $COOR_{7B}$, $CONR_{7B}R_{8B}$, $NR_{7B}R_{8B}$, $NR_{7B}COR_{8B}$, and $NR_{7B}SO_2R_{8B}$;

$R_{3B}$ and $R_{4B}$ are independently selected from hydrogen and substituted or unsubstituted alkyl;

$R_{5B}$ is selected from hydrogen and substituted or unsubstituted alkyl;

$L_B$ is —(C—$R_{10B}R_{11B})_{nB}$— wherein $R_{10B}$ and $R_{11B}$ are independently selected from hydrogen and alkyl; and nB is 0, 1, 2, or 3;

X is selected from O, S and $NR_{12B}$ wherein $R_{12B}$ is selected from hydrogen or alkyl;

Y is selected from —(C—$R_{10B}R_{11B})_{mB}$—, O, —$NR_{7B}R_{8B}$, —$N(R_{7B})CO$—, —$SO_2N(R_{7B})$— and —$NR_{7B}CON(R_{8B})$—, provided that when Y is O, nB=0, mB=0 and $R_{5B}$ is methyl, $R_{3B}$ and $R_{4B}$ cannot be methyl;

$R_{1C}$ is selected from alkyl, substituted or unsubstituted aryl, substituted or unsubstituted heteroaryl, substituted or unsubstituted cycloalkyl and substituted or unsubstituted heterocycloalkyl wherein the heteroaryl and heterocycloalkyl include nitrogen, oxygen or sulfur as a heteroatom, and wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}$, $CONR_{7C}R_{8C}$, $NR_{7C}R_{8C}$, $NR_{7C}COR_{8C}$, $NR_{7C}SO_2R_{8C}$, $NR_{9C}CONR_{7C}R_{8C}$;
    wherein $R_{7C}$, $R_{8C}$ and $R_{9C}$ are as each independently selected from hydrogen, alkyl, heteroalkyl, substituted or unsubstituted aryl, substituted or unsubstituted arylalkyl, substituted or unsubstituted heteroaryl, substituted or unsubstituted heteroarylalkyl, substituted or unsubstituted cycloalkyl, and substituted or unsubstituted heterocycloalkyl;
    wherein $NR_{7C}R_{8C}$ optionally forms a substituted or unsubstituted mono or bicyclic ring having one to four heteroatoms selected from N, O and S; and
    wherein $R_{7C}$ and $R_{8C}$ may form a 4, 5, 6 or 7-member cyclic ring system;
    wherein said substitutions are selected from hydrogen, hydroxyl, sulfhydryl, alkoxy, thioalkoxy, alkyl and halogen;

$R_{2C}$ is selected from hydrogen and alkyl group;

$R_{3C}$ is hydrogen or alkyl;

$R_{4C}$ is selected from aklyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include nitrogen, oxygen or sulfur as a heteroatom;
    wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}$, $CONR_{7C}R_{8C}$, $NR_{7C}R_{8C}$, $NR_{7C}COR_{8C}$, $NR_{7C}SO_2R_{8C}$, $NR_{7C}CONR_{8C}R_{9C}$; and
    wherein $R_{7C}$, $R_{8C}$ and $R_{9C}$ are as defined above;

$R_{5C}$ and $R_{6C}$ are independently selected from hydrogen, alkyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include nitrogen, oxygen or sulfur as a heteroatom;
    wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}C$, $CONR_{7C}R_{8C}$, $NR_{7C}R_{2C}$, $NR_{7C}COR_{8C}$, $NR_{7C}SO_2R_{8C}$, $NR_{7C}CONR_{8C}R_{9C}$; and
    wherein $R_{7C}$, $R_{8C}$ and $R_{9C}$ are as defined above;

$L_{1C}$ is —(C—$R_{10C}R_{11C})_{nC}$— wherein $R_{10C}$ and $R_{11C}$ are independently selected from hydrogen and alkyl and nC is 0, 1, 2, or 3;

$L_{2C}$ is selected from the group consisting of —(C—$R_{10C}R_{11C})_n$—, —$CON(R_{7C})$—, —$SO_2N(R_{7C})$—, —$NR_{7C}CON(R_{8C})$—, and —$OCON(R_{7C})$;

$R_{1C}$ and $R_{2C}$ are connected to make a substituted or unsubstituted cycloalkyl and substituted or unsubstituted heterocycloalkyl wherein the heteroatom is nitrogen, oxygen or sulfur;
    wherein said substitutions are selected from hydrogen, hydroxyl, sulfhydryl, alkoxy, thioalkoxy, alkyl, halogen, CN, $CF_3$, $NO_2$, $COOR_7$, $NC(O)OR_7$, $CONR_7R_8$, $NR_7R_8$, $NR_7COR_8$, $NR_7SO_2R_8$, $NR_7CONR_8R_9$; provided $R_{2C}$ cannot be hydrogen when $L_{1C}$=0 and $R_{1C}$ is a phenyl ring substituted with hydrogen and methyl group, $L_{2C}$-$R_{4C}$ is hydrogen;

$R_{1D}$ is selected from substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include nitrogen, oxygen or sulfur as a heteroatom;
    wherein said substitutions are selected from hydrogen, hydroxyl, sulfhydryl, alkoxy, thioalkoxy, alkyl, halogen, CN, $CF_3$, $NO_2$, $COOR_{7D}$, $NC(O)OR_{7D}$, $CONR_{7D}R_{8D}$, $NR_{7D}R_{8D}$, $NR_{7D}COR_{8D}$, $NR_{7D}SO_2R_{8D}$, $NR_{9D}CONR_{7D}R_{8D}$;
    wherein $R_{7D}$, $R_{8D}$ and $R_{9D}$ are as each independently selected from hydrogen, alkyl, heteroalkyl, substituted or unsubstituted aryl, substituted or unsubstituted arylalkyl, substituted or unsubstituted heteroaryl, substituted or unsubstituted heteroarylalkyl, substituted or unsubstituted cycloalkyl, and substituted or unsubstituted heterocycloalkyl;
    wherein $NR_{7D}R_{8D}$ optionally form a substituted or unsubstituted mono or bicyclic ring having one to four heteroatoms selected from N, O and S; and
    wherein $R_{7D}$ and $R_{8D}$ may form a 4, 5, 6 or 7-member cyclic ring;
    wherein said substitutions are selected from hydrogen, hydroxyl, sulfhydryl, alkoxy, thioalkoxy, alkyl and halogen;

$R_{2D}$ is selected from hydrogen and substituted or unsubstituted alkyl group, $COR_{7D}$, $CONR_{7D}R_{8D}$, $SO_2R_{7D}$; provided $R_{2D}$ cannot be hydrogen when $R_{1D}$ is a phenyl ring.

$R_{3D}$ is selected from hydrogen and alkyl group, heteroalkyl; substituted or unsubstituted aryl and substituted or unsubstituted heteroaryl,
    wherein said substitutions are selected from hydrogen, hydroxyl, sulfhydryl, alkoxy, thioalkoxy, alkyl, halogen, CN, $CF_3$, $NO_2$, $COOR_{7D}$, $NC(O)OR_{7D}$, $CONR_{7D}R_{8D}$, $NR_{7D}R_{8D}$, $NR_{7D}COR_{8D}$, $NR_{7D}SO_2R_{8D}$, $NR_{7D}CONR_{8D}R_{9D}$; and
    wherein $R_{7D}$, $R_{8D}$ and $R_{9D}$ are as defined above;

$R_{4D}$ is selected from aklyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include nitrogen, oxygen or sulfur as a heteroatom;
    wherein said substitutions are selected from hydrogen, hydroxyl, sulfhydryl, alkoxy, thioalkoxy, alkyl, halogen, CN, $CF_3$, $NO_2$, $COOR_{7D}$, $NC(O)OR_{7D}$, $CONR_{7D}R_{8D}$, $NR_{7D}R_{8D}$, $NR_{7D}COR_{8D}$, $NR_{7D}SO_2R_{8D}$, $NR_{7D}CONR_{8D}R_{9D}$; and
    wherein $R_{7D}$, $R_{8D}$ and $R_{9D}$ are as defined above;

$R_{5D}$ and $R_{6D}$ are selected from hydrogen, alkyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include nitrogen, oxygen or sulfur as a heteroatom;
    wherein said substitutions are selected from hydrogen, hydroxyl, sulfhydryl, alkoxy, thioalkoxy, alkyl, halogen, CN, CF$_3$, NO$_2$, COOR$_{7D}$, NC(O)OR$_{7D}$, CONR$_{7D}$R$_{8D}$, NR$_{7D}$R$_{BD}$, NR$_{7D}$COR$_{8D}$, NR$_{7D}$SO$_2$R$_{BD}$, NR$_{7D}$CONR$_{8D}$R$_{9D}$; and wherein R$_{7D}$, R$_{8D}$ and R$_{9D}$ are as defined above; and X$_D$ is selected from the group consisting of CH$_2$, C(O)N (R$_{7D}$)—, O, N—R$_{7D}$, and S, where in R$_{7D}$ is defined as above.

According to another aspect, compounds of Formula 1A are provided

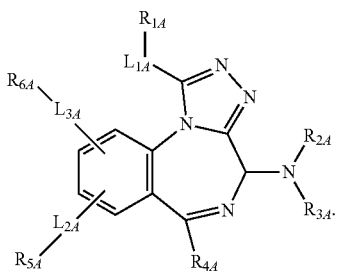

Formula 1A

According to one embodiment, R$_{1A}$ is selected from substituted or unsubstituted aryl, or substituted or unsubstituted heteroaryl. According to such an embodiment, R$_{3A}$ may be hydrogen. According to one embodiment, R$_{4A}$ is selected from substituted or unsubstituted aryl, or substituted or unsubstituted heteroaryl. According to one embodiment, R$_{6A}$ and R$_{5A}$ are independently selected from hydrogen, substituted or unsubstituted aryl, and substituted or unsubstituted heteroaryl. According to one embodiment, R$_{10A}$ and R$_{11A}$ are independently selected from hydrogen and methyl and n is 1 or 2. According to one embodiment, L$_{2A}$ is selected from the group consisting of alkyl, —CONR$_{7A}$R$_{8A}$, and —SO$_2$NR$_{7A}$R$_{8A}$.

According to an alternative embodiment, R$_{2A}$ is NC(O)OR$_{7A}$. According to one embodiment, R$_{3A}$ is hydrogen. According to one embodiment, R$_{4A}$ is selected from substituted or unsubstituted aryl, or substituted or unsubstituted heteroaryl. According to one embodiment, R$_{5A}$ and R$_{6A}$ are independently selected from substituted or unsubstituted aryl, or substituted or unsubstituted heteroaryl. According to one embodiment, L$_{1A}$ is —(C—R$_{10A}$R$_{11A}$)$_{nA}$— wherein R$_{10A}$ and R$_{11A}$ are independently selected from hydrogen and methyl and nA is 1 or 2. According to one embodiment, L$_{2A}$ is selected from alkyl, CONR$_{7A}$R$_{8A}$, and SO$_2$NR$_{7A}$R$_{8A}$. According to one embodiment, R$_{1A}$ is selected from substituted or unsubstituted aryl and substituted or unsubstituted heteroaryl; R$_{2A}$ and R$_{3A}$ are hydrogen; R$_{4A}$ is selected from substituted or unsubstituted aryl and substituted or unsubstituted heteroaryl; R$_{6A}$ and R$_{5A}$ is selected from substituted or unsubstituted aryl and substituted or unsubstituted heteroaryl; L$_{1A}$ is —(C—R$_{10A}$R$_{11A}$)$_{nA}$— wherein R$_{10A}$ and R$_{11A}$ are independently selected from hydrogen and methyl and nA is 1 or 2; and L$_{2A}$ is selected from the group consisting of alkyl, —CONR$_7$R$_{8A}$, and —SO$_2$NR$_7$R$_{8A}$. According to one embodiment, R$_{6A}$ and R$_{5A}$ are independently selected from hydrogen

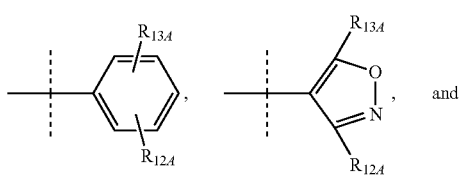

and

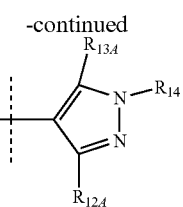

wherein R$_{12A}$ and R$_{13A}$ are independently selected from hydrogen, hydroxyl, sulfhydryl, alkoxy, thioalkoxy, alkyl and halogen.

According to another aspect, compounds having the structure of Formula 1B are provided

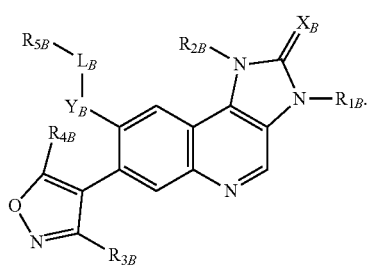

Formula 1B

According to one embodiment, R$_{1B}$ is selected from substituted or unsubstituted aryl, or substituted or unsubstituted heteroaryl. According to one embodiment, R$_{2B}$ is selected from hydrogen, substituted or unsubstituted alkyl group and substituted or unsubstituted heterocycloalkyl, wherein the heterocycloalkyl includes nitrogen, oxygen or sulfur as a heteroatom. According to one embodiment, R$_{1B}$ is selected from substituted or unsubstituted aryl, or substituted or unsubstituted heteroaryl; R$_{2B}$ is selected from hydrogen, substituted or unsubstituted alkyl group, or substituted or unsubstituted heterocycloalkyl, wherein the heterocycloalkyl or heteroaryl includes nitrogen, oxygen or sulfur as a heteroatom.

According to another aspect, compounds having the structure of Formula 1C are provided

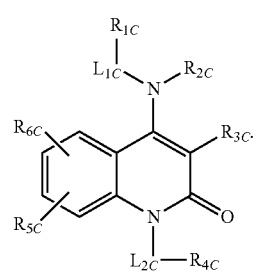

Formula 1C

According to one embodiment, wherein R$_{1C}$ is selected from substituted or unsubstituted aryl, or substituted or unsubstituted heteroaryl. According to such an embodiment, R$_{3C}$ is hydrogen. According to one embodiment, R$_{4C}$ is selected from substituted or unsubstituted aryl, or substituted or unsubstituted heteroaryl. According to one embodiment, R$_{6C}$ and R$_{5C}$ are independently selected from hydrogen, substituted or unsubstituted aryl, and substituted or unsubstituted heteroaryl. According to one embodiment, L$_{1C}$ is —(C—$R_{10C}R_{11C})_{nC}$— wherein $R_{10C}$ and $R_{11C}$ are independently selected from hydrogen and methyl and nC is 1 or 2. According to one embodiment, $L_{2C}$ is selected from alkyl, $CONR_{7C}R_{8C}$, and $SO_2NR_{7C}R_{8C}$.

According to an alternative embodiment, $R_{2C}$ is hydrogen. According to one embodiment, $R_{3C}$ is hydrogen. According to one embodiment, $R_{4C}$ is selected from substituted or unsubstituted aryl, or substituted or unsubstituted heteroaryl. According to one embodiment, $R_{5C}$ and $R_{6C}$ are independently selected from substituted or unsubstituted aryl, or substituted or unsubstituted heteroaryl. According to one embodiment, $L_{1C}$ is —(C—$R_{10C}R_{11C})_n$— wherein $R_{10C}$ and $R_{11C}$ are independently selected from hydrogen and methyl and n is 1 or 2. According to one embodiment, $L_{2C}$ is selected from the group consisting of alkyl, —$CONR_{7C}R_{8C}$, and $SO_2NR_{7C}R_{8C}$. According to one embodiment, $R_{3C}$ is hydrogen. According to one embodiment, $R_{1C}$ is selected from substituted or unsubstituted aryl, or substituted or unsubstituted heteroaryl; $R_{2C}$ and $R_{3C}$ are hydrogen; $R_{4C}$ is selected from substituted or unsubstituted aryl, or substituted or unsubstituted heteroaryl; $R_{6C}$ and $R_{5C}$ is selected from substituted or unsubstituted aryl, or substituted or unsubstituted heteroaryl; $L_{1C}$ is —(C—$R_{10C}R_{11C})_{nC}$— wherein $R_{10C}$ and $R_{11C}$ are independently selected from hydrogen and methyl and nC is 1 or 2; and $L_{2C}$ is selected from the group consisting of alkyl, —$CONR_{7C}R_{8C}$, and —$SO_2NR_{7C}R_{8C}$. According to one embodiment, $R_{6C}$ and $R_{5C}$ is independently selected from hydrogen

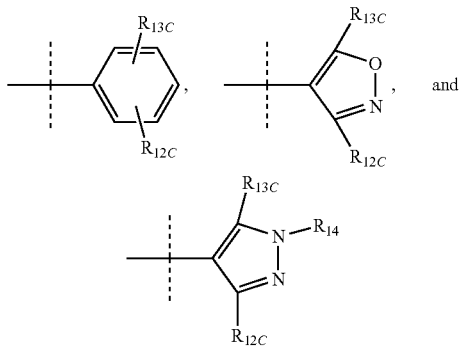

wherein $R_{12C}$ and $R_{13C}$ are independently selected from hydrogen, hydroxyl, sulfhydryl, alkoxy, thioalkoxy, alkyl and halogen.

According to another aspect, compounds of Formula 1D are provided

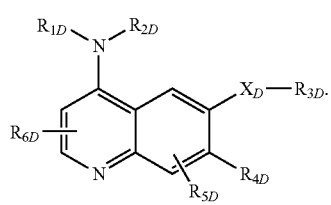

Formula 1D

According to one embodiment, $R_{1D}$ is selected from substituted or unsubstituted aryl, or substituted or unsubstituted heteroaryl. According to one embodiment, $R_{2D}$ is —$COR_{7D}$. According to one embodiment, $R_{3D}$ is substituted or unsubstituted alkyl. According to one embodiment, $R_{4D}$ is substituted or unsubstituted heteroaryl. According to one embodiment, $R_{6D}$ and $R_{5D}$ are hydrogen.

According to an alternative embodiment, $R_{2D}$ is selected from —$COR_{7D}$, —$CONR_{7D}R_{8D}$, and —$SO_2R_{7D}$. According to one embodiment, $R_{3D}$ is substituted or unsubstituted alkyl group, or substituted or unsubstituted heteroalkyl. According to one embodiment, $R_{4D}$ is selected from substituted or unsubstituted aryl, or substituted or unsubstituted heteroaryl. According to one embodiment, $R_{5D}$ and $R_{6D}$ are independently selected from hydrogen, and alkyl. According to one embodiment, $X_D$ is selected from —C(O)N($R_{7D}$)—, —O and —N—$R_{7D}$. According to one embodiment, $R_{1D}$ is selected from substituted or unsubstituted aryl, or substituted or unsubstituted heteroaryl, $R_{2D}$ is —$COR_{7D}$, $R_{3D}$ is substituted or unsubstituted alkyl, $R_{4D}$ is selected from substituted or unsubstituted aryl, or substituted or unsubstituted heteroaryl, $R_{6D}$ and $R_{5D}$ are hydrogen. According to one embodiment, $R_{4D}$ is selected from

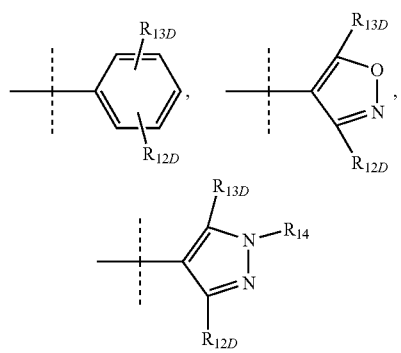

wherein $R_{12D}$ and $R_{13D}$ are independently selected from hydrogen, hydroxyl, sulfhydryl, alkoxy, thioalkoxy, alkyl and halogen.

According to another aspect, the present invention includes pharmaceutical compositions comprising a compound of the present invention or a pharmaceutically acceptable salt thereof. The pharmaceutical compositions of the present invention can be used for treating or preventing a wide variety of conditions or disorders, particularly those disorders mediated by acetylated proteins involved in the regulation of gene expression.

According to another aspect, the present invention includes methods for treating, preventing, delaying the onset of, or slowing the progression of disorders mediated by acetylated proteins involved in the regulation of gene expression, in mammals in need of such treatment. The methods involve administering to a subject a therapeutically effective amount of a compound as provided herein, including a salt thereof, or a pharmaceutical composition that includes such compounds.

DETAILED DESCRIPTION OF THE INVENTION

The scope of the present invention includes all combinations of aspects and embodiments.

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well. Thus, for example, $C_{1-6}$ alkyl represents a straight or branched chain hydrocarbon containing one to six carbon atoms.

As used herein the term "alkyl" refers to a straight or branched chain hydrocarbon, which may be optionally substituted, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used herein, the term "alkene" refers to an unsaturated hydrocarbon that includes one or more carbon-carbon double bonds. The term "lower alkene" refers to an alkene that includes from five to twenty carbon atoms, such as from two to ten carbon atoms, while the term "upper alkene" refers to an alkene that includes more than twenty carbon atoms, such as from twenty-one to one hundred carbon atoms. The term "substituted alkene" refers to an alkene that has one or more of its hydrogen atoms replaced by one or more substituent groups, such as halogen.

As used herein, the term "alkyne" refers to an unsaturated hydrocarbon that includes one or more carbon-carbon triple bonds. The term "lower alkyne" refers to an alkyne that includes from five to twenty carbon atoms, such as from two to ten carbon atoms, while the term "upper alkyne" refers to an alkyne that includes more than twenty carbon atoms, such as from twenty-one to one hundred carbon atoms. The term "substituted alkyne" refers to an alkyne that has one or more of its hydrogen atoms replaced by one or more substituent groups, such as halogen.

As used herein, the term "cycloalkyl" refers to a fully saturated optionally substituted monocyclic, bicyclic, or bridged hydrocarbon ring, with multiple degrees of substitution being allowed. Preferably, the ring is three to twelve-membered, more preferably, from five- to six-membered. Exemplary "cycloalkyl" groups as used herein include, but are not limited to, cyclopropyl, cyclobutyl, cyclopentyl, cyclohexyl, and cycloheptyl.

As used herein, the term "alkoxy" refers to a group —$OR^a$, where $R^a$ is "alkyl" as defined herein.

As used herein, the term "heterocycloalkyl" or "heterocycle" or "heterocyclyl" refers to an optionally substituted mono- or polycyclic ring system, optionally containing one or more degrees of unsaturation, and also containing one or more heteroatoms, which may be optionally substituted, with multiple degrees of substitution being allowed. Exemplary heteroatoms include nitrogen, oxygen, or sulfur atoms, including N-oxides, sulfur oxides, and dioxides. Preferably, the ring is three to twelve-membered, preferably five or six-membered and is either fully saturated or has one or more degrees of unsaturation. Such rings may be optionally fused to one or more of another heterocyclic ring(s) or cycloalkyl ring(s). Examples of "heterocyclic" groups as used herein include, but are not limited to, tetrahydrofuran, pyran, tetrahydropyran, 1,4-dioxane, 1,3-dioxane, piperidine, pyrrolidine, morpholine, tetrahydrothiopyran, and tetrahydrothiophene.

As used herein, the term "aryl" refers to a single benzene ring or fused benzene ring system which may be optionally substituted, with multiple degrees of substitution being allowed.

Examples of "aryl" groups as used include, but are not limited to, phenyl, 2-naphthyl, 1-naphthyl, anthracene, and phenanthrene. Preferable aryl rings have five- to ten-members. The term "aryl" also includes a fused benzene ring system, namely where a cyclic hydrocarbon or heterocycle (e.g., a cyclohexane or dioxane ring) or heteroaryl (e.g., pyridine) is fused with an aromatic ring (aryl, such as a benzene ring).

As used herein, the term "heteroaryl" refers to a monocyclic five to seven membered aromatic ring, a fused bicyclic aromatic ring system comprising two of such aromatic rings, which may be optionally substituted, with multiple degrees of substitution being allowed, or to a fused bicyclic ring system namely where a cycloalkyl or heterocycle (e.g., a cyclohexane or dioxane ring) is fused with a heteroaryl ring. Preferably, heteroaryl rings contain five- to ten-members. These heteroaryl rings contain one or more nitrogen, sulfur, and/or oxygen atoms. In certain embodiments, the heteroaryl rings contain one to three nitrogen, one to three oxygen, and one or two sulfur atoms. N-oxides, sulfur oxides, and dioxides are permissible heteroatom substitutions. Examples of "heteroaryl" groups as used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinoxaline, benzofuran, benzoxazole, benzothiophene, indole, indazole, benzimidazole, imidazopyridine, pyrazolopyridine, and pyrazolopyrimidine.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$.

As used herein, the term "sulfhydryl" refers to refers to a —SH group.

As used herein, the term "carboxyamido" refers to —NH—C(O)—W, wherein W is hydrogen or an unsubstituted or substituted alkyl, alkene, alkyne, cycloalkyl, aryl, or heterocycle group.

As used herein, the term "amine" is given its ordinary meaning and includes primary, secondary and tertiary amines.

As used herein, the term "amido" refers to a group of the formula —C(O)$NR^{15}R^{16}$, wherein $R^{15}$ and $R^{16}$ are alkyl, cycloalkyl or heterocycle, or $R^{15}$ and $R^{16}$ can form cycloalkyl or heterocycle. As used herein, the term "sulfamido" refers to the group —$SO_2$—$NR^{15}R^{16}$.

As used herein, the term "pharmaceutically acceptable" refers to carrier(s), diluent(s), excipient(s) or salt forms of the compounds of the present invention that are compatible with the other ingredients of the formulation and not deleterious to the recipient of the pharmaceutical composition.

As used herein, the term "pharmaceutical composition" refers to a compound of the present invention optionally admixed with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutic amount", and "effective dose" refer to an amount of the compound of the present invention sufficient to elicit the desired pharmacological or therapeutic effects, thus resulting in an effective treatment of a disorder. Treatment of a disorder may be manifested by delaying or preventing the onset or progression of the disorder, as well as the onset or progression of symptoms associated with the disorder. Treatment of a disorder may also be manifested by a decrease or elimination of symptoms, reversal of the progression of the disorder, as well as any other contribution to the well being of the patient. The effective dose can vary, depending upon factors such as the condition of the patient, the severity of the symptoms of the disorder, and the manner in which the pharmaceutical composition is administered. Effective doses may be administered as a single dose, or as one or more doses that may be administered over a 24 hours period.

According to one embodiment, the compound is at least one compound selected from Formula I, Formula 1A, Formula 1B, Formula 1C or Formula 1D as provided herein, including those compounds set forth in Tables 1-6 and 10.

According to one embodiment, the compound is at least one compound selected from:
6-chloro-3-cinnamoyl-4-phenylquinolin-2(1H)-one;
6-chloro-3-(3-(2-chloro-6-fluorophenyl)acryloyl)-4-phenylquinolin-2(1H)-one;
6-chloro-3-(3-(2,4-dichlorophenyl)acryloyl)-4-phenylquinolin-2(1H)-one;
6-chloro-4-phenyl-3-(3-o-tolylacryloyl)quinolin-2(1H)-one;
6-chloro-3-(3-(2-methoxyphenyl)acryloyl)-4-phenylquinolin-2(1H)-one;
6-chloro-3-(3-(3,4-dimethoxyphenyl)acryloyl)-4-phenylquinolin-2(1H)-one;
6-chloro-4-phenyl-3-(3-(thiophen-2-yl)acryloyl)quinolin-2(1H)-one;
6-chloro-3-(3-(4-(dimethylamino)phenyl)acryloyl)-4-phenylquinolin-2(1H)-one;
6-bromo-3-(3-(2,3-dihydrobenzo[b][1,4]dioxin-6-yl)acryloyl)-4-phenylquinolin-2(1H)-one;
6-bromo-3-(3-(2,5-dimethoxyphenyl)acryloyl)-4-phenylquinolin-2(1H)-one;
6-chloro-3-cinnamoyl-4-(pyridin-4-yl)quinolin-2(1H)-one;
6-chloro-4-(pyridin-3-yl)-3-(3-o-tolylacryloyl)quinolin-2(1H)-one;
6-chloro-N-(2-methylbenzyl)-2-oxo-4-phenyl-1,2-dihydroquinoline-3-carboxamide;
6-chloro-3-cinnamoyl-4-phenyl-1,8-naphthyridin-2(1H)-one;
6-chloro-3-(3-(2-chloro-6-fluorophenyl)acryloyl)-4-(pyridin-4-yl)quinolin-2(1H)-one;
6-chloro-3-(3-(3-fluoro-5-methylpyridin-4-yl)acryloyl)-4-(pyridin-3-yl)quinolin-2(1H)-one;
6-chloro-3-cinnamoyl-N-(3-methoxyphenyl)-2-oxo-1,2-dihydroquinoline-4-sulfonamide;
6-chloro-3-cinnamoyl-2-oxo-N-(pyridin-3-yl)-1,2-dihydroquinoline-4-sulfonamide;
6-chloro-3-(3-(2-chloro-6-fluorophenyl)but-2-enoyl)-4-phenylquinolin-2(1H)-one;
3-cinnamoyl-6-(3,5-dimethylisoxazol-4-yl)-4-(pyridin-3-yl)quinolin-2(1H)-one;
6-chloro-3-(2-methyloxazol-4-yl)-4-(piperidin-1-yl)quinolin-2(1H)-one;
6-chloro-3-(2-methyloxazol-4-yl)-4-(pyrrolidin-1-yl)quinolin-2(1H)-one;
6-chloro-3-(2-methyloxazol-4-yl)-4-morpholinoquinolin-2(1H)-one;
5-(2-chlorovinyl)-4-(4-ethylpiperazin-1-yl)-3-(2-methyloxazol-4-yl)-6-vinylpyridin-2(1H)-one;
6-chloro-3-(2-methyloxazol-4-yl)-4-(1H-pyrrol-1-yl)quinolin-2(1H)-one;
6-chloro-3-(2-methyloxazol-4-yl)-4-(1H-pyrazol-1-yl)quinolin-2(1H)-one;
6-chloro-3-(3,5-dimethylisoxazol-4-yl)-4-(pyrrolidin-1-yl)quinolin-2(1H)-one;
6-chloro-3-(3,5-dimethylisoxazol-4-yl)-4-(piperidin-1-yl)quinolin-2(1H)-one;
6-chloro-3-(3,5-dimethylisoxazol-4-yl)-4-morpholinoquinolin-2(1H)-one;
6-chloro-3-(3,5-dimethylisoxazol-4-yl)-4-(4-methylpiperazin-1-yl)quinolin-2(1H)-one;
6-chloro-3-(3,5-dimethylisoxazol-4-yl)-4-(pyridin-4-yl)quinolin-2(1H)-one;
6-chloro-3-(3,5-dimethylisoxazol-4-yl)-4-(pyridin-3-yl)quinolin-2(1H)-one;
6-chloro-3-(3,5-dimethylisoxazol-4-yl)-4-(pyridin-2-yl)quinolin-2(1H)-one;
6-chloro-3-(3,5-dimethylisoxazol-4-yl)-4-(1H-pyrrol-1-yl)quinolin-2(1H)-one;
6-chloro-3-(3,5-dimethylisoxazol-4-yl)-4-(furan-3-yl)quinolin-2(1H)-one;
6-chloro-3-(3,5-dimethylisoxazol-4-yl)-4-(isoxazol-4-yl)quinolin-2(1H)-one;
6-chloro-3-(isoxazol-4-yl)-4-(pyridin-4-yl)quinolin-2(1H)-one;
6-chloro-3-(1H-pyrazol-4-yl)-4-(pyridin-4-yl)quinolin-2(1H)-one;
6-chloro-3-(furan-3-yl)-4-(pyridin-4-yl)quinolin-2(1H)-one;
6-chloro-4-(pyridin-4-yl)-3-(thiophen-3-yl)quinolin-2(1H)-one;
6-chloro-3-(1H-imidazol-4-yl)-4-(pyridin-4-yl)quinolin-2(1H)-one;
6-(3,5-dimethylisoxazol-4-yl)-3-(morpholinosulfonyl)-4-(pyridin-3-yl)quinolin-2(1H)-one;
6-(3,5-dimethylisoxazol-4-yl)-3-(4-methylpiperazin-1-ylsulfonyl)-4-(pyridin-3-yl)quinolin-2(1H)-one;
N-(3-cinnamoyl-2-oxo-4-(pyridin-3-yl)-1,2-dihydroquinolin-6-yl)-5-methylisoxazole-3-carboxamide;
6-(3,5-dimethylisoxazol-4-yl)-3-(morpholinosulfonyl)quinolin-2(1H)-one;
6-(3,5-dimethylisoxazol-4-yl)-3-(4-methylpiperazin-1-ylsulfonyl)quinolin-2(1H)-one;
4-(6-(3,5-dimethylisoxazol-4-yl)-2-oxo-1,2-dihydroquinolin-3-yl)-N-ethyl-N-methylbenzamide;
6-(3,5-dimethylisoxazol-4-yl)-3-(2-fluoro-5-(morpholine-4-carbonyl)phenyl)quinolin-2(1H)-one;
N-cyclopentyl-3-(6-(3,5-dimethylisoxazol-4-yl)-2-oxo-1,2-dihydroquinolin-3-yl)benzenesulfonamide;
3-(6-(3,5-dimethylisoxazol-4-yl)-2-oxo-1,2-dihydroquinolin-3-yl)-N,N-dimethylbenzenesulfonamide;
3-(6-(3,5-dimethylisoxazol-4-yl)-2-oxo-1,2-dihydroquinolin-3-yl)-N-(1-methylpyrrolidin-3-yl)benzenesulfonamide;
3-(1H-benzo[d]imidazole-2-carbonyl)-6-(3,5-dimethylisoxazol-4-yl)quinolin-2(1H)-one;
5-(3,5-dimethylisoxazol-4-yl)-3-(2-(pyridin-3-yl)ethylidene)indolin-2-one;
6-(3,5-dimethylisoxazol-4-yl)-1-(pyridin-3-ylmethyl)-1H-benzo[d]imidazol-2(3H)-one;
6-(3-chloroisoxazol-5-yl)-3-(morpholinosulfonyl)-4-(pyridin-3-yl)quinolin-2(1H)-one;
3-(3,5-dimethylisoxazol-4-yl)-6-(morpholinosulfonyl)-4-(pyridin-3-yl)quinolin-2(1H)-one;
6-(3-chloroisoxazol-5-yl)-3-cinnamoyl-4-phenylquinolin-2(1H)-one;
(E)-methyl 5-(3-cinnamoyl-2-oxo-4-(pyridin-3-yl)-1,2-dihydroquinolin-6-yl)-2-methyloxazole-4-carboxylate;

6-(3-chloroisoxazol-5-yl)-3-cinnamoyl-4-(pyridin-3-yl)quinolin-2(1H)-one;
3-cinnamoyl-6-(3,5-dimethylisoxazol-4-yl)-4-(phenylamino)quinolin-2(1H)-one;
3-cinnamoyl-6-(3,5-dimethylisoxazol-4-yl)-4-(pyridin-3-ylamino)quinolin-2(1H)-one;
N-(3-benzoyl-2-oxo-1,2-dihydroquinolin-5-yl)-2-methoxybenzenesulfonamide;
N-(3-cinnamoyl-2-oxo-1,2-dihydroquinolin-5-yl)pyridine-3-sulfonamide;
N-(3-benzoyl-2-oxo-1,2-dihydroquinolin-5-yl)pyridine-3-sulfonamide;
N-(3-cinnamoyl-2-oxo-1,2-dihydroquinolin-5-yl)-2-methoxybenzenesulfonamide;
6-(3,5-dimethylisoxazol-4-yl)-3-(morpholine-4-carbonyl)-4-(pyridin-3-yl)quinolin-2(1H)-one;
6-chloro-3-(3-chloroisoxazol-5-yl)quinolin-2(1H)-one;
N-(6-chloro-2-oxo-1,2-dihydroquinolin-3-yl)-5-methylisoxazole-3-carboxamide;
6-(3,5-dimethylisoxazol-4-yl)-3-(morpholine-4-carbonyl)quinolin-2(1H)-one;
6-chloro-4-(4-(2-fluorophenyl)piperazin-1-yl)-3-(2-methyloxazol-4-yl)quinolin-2(1H)-one;
6-chloro-4-(4-(3-fluorophenyl)piperazin-1-yl)-3-(2-methyloxazol-4-yl)quinolin-2(1H)-one;
6-chloro-3-(2-methyloxazol-4-yl)-4-(4-(pyridin-2-yl)piperazin-1-yl)quinolin-2(1H)-one;
6-chloro-3-(2-methyloxazol-4-yl)-4-(4-phenethylpiperazin-1-yl)quinolin-2(1H)-one;
3-bromo-6-chloro-4-hydroxy-1-(4-methoxybenzyl)quinolin-2(1H)-one;
6-chloro-1H-benzo[d][1,3]oxazine-2,4-dione;
1-benzyl-6-chloro-1H-benzo[d][1,3]oxazine-2,4-dione;
6-chloro-1-(4-methoxybenzyl)-1H-benzo[d][1,3]oxazine-2,4-dione;
1-benzyl-6-chloro-3-(3,5-dimethylisoxazol-4-yl)-2-oxo-1,2-dihydroquinolin-4-yl trifluoromethanesulfonate;
3-acetyl-6-bromo-4-phenylquinolin-2(1H)-one;
6-bromo-3-cinnamoyl-4-phenylquinolin-2(1H)-one;
6-chloro-4-hydroxy-1-(4-methoxybenzyl)-3-(2-methyloxazol-4-yl)quinolin-2(1H)-one;
6-chloro-1-(4-methoxybenzyl)-3-(2-methyloxazol-4-yl)-2-oxo-1,2-dihydroquinolin-4-yl 4-methylbenzenesulfonate;
-chloro-1-(4-methoxybenzyl)-3-(2-methyloxazol-4-yl)-2-oxo-1,2-dihydroquinolin-4-yl benzenesulfonate;
6-chloro-1-(4-methoxybenzyl)-3-(2-methyloxazol-4-yl)-2-oxo-1,2-dihydroquinolin-4-yl 4-fluorobenzenesulfonate;
6-chloro-1-(4-methoxybenzyl)-3-(2-methyloxazol-4-yl)-2-oxo-1,2-dihydroquinolin-4-yl 4-chlorobenzenesulfonate;
6-chloro-1-(4-methoxybenzyl)-3-(2-methyloxazol-4-yl)-2-oxo-1,2-dihydroquinolin-4-yl naphthalene-2-sulfonate;
6-chloro-1-(4-methoxybenzyl)-3-(2-methyloxazol-4-yl)-2-oxo-1,2-dihydroquinolin-4-yl quinoline-8-sulfonate;
6-chloro-1-(4-methoxybenzyl)-3-(2-methyloxazol-4-yl)-2-oxo-1,2-dihydroquinolin-4-yl biphenyl-4-sulfonate;
N-(4-(2-chlorovinyl)-6-(3,5-dimethylisoxazol-4-yl)-5-hydroxyhexa-1,5-dien-3-yl)-N-(hepta-2,4,6-trienyl)formamide;
N1,N3-bis(4-bromophenyl)malonamide;
N1,N3-bis(4-(3,5-dimethylisoxazol-4-yl)phenyl)malonamide;
6-(3,5-dimethylisoxazol-4-yl)-4-hydroxyquinolin-2(1H)-one;
4-chloro-6-(3,5-dimethylisoxazol-4-yl)quinolin-2(1H)-one;
4-(benzylamino)-6-(3,5-dimethylisoxazol-4-yl)quinolin-2(1H)-one;
4-(2-chlorobenzylamino)-6-(3,5-dimethylisoxazol-4-yl)quinolin-2(1H)-one;
6-(3,5-dimethylisoxazol-4-yl)-4-morpholinoquinolin-2(1H)-one;
6-(3,5-dimethylisoxazol-4-yl)-4-(piperidin-1-yl)quinolin-2(1H)-one;
4-(benzylamino)-1-(benzylsulfonyl)-6-(3,5-dimethylisoxazol-4-yl)quinolin-2(1H)-one;
and salts thereof.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms. The salts of the present invention can be pharmaceutically acceptable salts which includes non-toxic salts of the compounds set forth herein.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Although it is possible to administer the compound of the present invention in the form of a bulk active chemical, it is preferred to administer the compound in the form of a pharmaceutical composition or formulation. Thus, pharmaceutical compositions are provided that include one or more compounds of Formula I and/or pharmaceutically acceptable salts thereof and one or more pharmaceutically acceptable carriers, diluents, or excipients. Another aspect of the invention provides a process for the preparation of a pharmaceutical composition including admixing one or more compounds of Formula I and/or pharmaceutically acceptable salts thereof with one or more pharmaceutically acceptable carriers, diluents or excipients.

The manner in which the compounds set forth herein may be administered can vary. According to one embodiment, the compounds can be administered orally. Preferred pharmaceutical compositions may be formulated for oral administration in the form of tablets, capsules, caplets, syrups, solutions, and suspensions. Such oral formulations can be provided in modified release dosage forms such as time-release tablet and capsule formulations. Pharmaceutical compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

Pharmaceutical compositions may also be administered using other means, for example, rectal administration. Formulations useful for rectal administration, such as suppositories, are well known to those of skill in the art. The compounds can also be administered by inhalation, for example, in the form of an aerosol; topically, such as, in lotion form; transdermally, such as, using a transdermal patch (for example, by using technology that is commercially available from Novartis and Alza Corporation); by powder injection; or by buccal, sublingual, or intranasal absorption. Pharmaceutical compositions may be formulated in unit dose form, or in multiple or subunit doses.

The administration of the pharmaceutical compositions described herein can be intermittent, or at a gradual, continuous, constant or controlled rate. The pharmaceutical compositions may be administered to a warm-blooded animal, for example, a mammal such as a human being. In addition, the time of day and the number of times per day that the pharmaceutical composition is administered can vary.

The compounds as provided herein may also be used for the preparation of a medicament for the treatment or prevention of a disease or condition mediated by inhibiting bromodomain-containing proteins from binding acetylated proteins.

Methods for treating, preventing, delaying the onset of, or slowing the progression of disorders mediated by acetylated proteins involved in the regulation of gene expression, in mammals in need of such treatment are also provided. The methods involve administering to a subject a therapeutically effective amount of a compound as provided herein, including a salt thereof, or a pharmaceutical composition that includes such compounds.

According to one embodiment, the methods include the administration of at least one compound provided in Tables 1-6 and 10. According to another embodiment, the methods include the administration of at least one of the following compounds:

6-bromo-4-phenyl-3-(6-phenyl-2-thioxo-1,2-dihydropyrimidin-4-yl)quinolin-2(1H)-one;
6-chloro-4-phenyl-3-(6-phenyl-2-thioxo-1,2-dihydropyrimidin-4-yl)quinolin-2(1H)-one;
6-chloro-3-(6-(pyridin-4-yl)-2-thioxo-1,2-dihydropyrimidin-4-yl)quinolin-2(1H)-one;
6-chloro-3-(6-phenyl-2-thioxo-1,2-dihydropyrimidin-4-yl)-4-(pyridin-3-yl)quinolin-2(1H)-one;
6-chloro-3,4-di(pyridin-4-yl)quinolin-2(1H)-one;
6-chloro-3-(pyridin-3-yl)-4-(pyridin-4-yl)quinolin-2(1H)-one;
6-chloro-3-(pyridin-2-yl)-4-(pyridin-4-yl)quinolin-2(1H)-one;
6-chloro-3-(5-(4,4-dimethyl-4,5-dihydrooxazol-2-yl)pyridin-3-yl)quinolin-2(1H)-one;
2,5-dimethoxy-N-((2-methoxynaphthalen-1-yl)methyl)aniline;
N-(6-bromo-2-oxo-4-phenyl-1,2-dihydroquinolin-3-yl)propionamide;
N-(6-bromo-2-oxo-4-phenyl-1,2-dihydroquinolin-3-yl)acetamide;
N-(6-bromo-2-oxo-4-phenyl-1,2-dihydroquinolin-3-yl)benzamide;
3-(1H-benzo[d]imidazol-2-ylthio)-6-chloro-4-phenylquinolin-2(1H)-one;
3-(4H-1,2,4-triazol-3-ylthio)-6-chloro-4-phenylquinolin-2(1H)-one;
6-chloro-4-phenyl-3-(tosylmethyl)quinolin-2(1H)-one;
3-(4-allyl-5-(thiophen-2-yl)-4H-1,2,4-triazol-3-ylthio)-6-chloro-4-phenylquinolin-2(1H)-one;
6-chloro-3-(4-(4-methoxyphenyl)-6-oxo-1,6-dihydropyrimidin-2-ylthio)-4-phenylquinolin-2(1H)-one;
4-phenyl-3-(pyridin-2-ylthio)quinolin-2(1H)-one;
3-(4-amino-6-oxo-1,6-dihydropyrimidin-2-ylthio)-6-chloro-4-phenylquinolin-2(1H)-one;
4-(2-oxo-4-phenyl-1,2-dihydroquinolin-3-yl)-2H-benzo[b][1,4]oxazin-3(4H)-one;
3-(4-ethyl-5-(morpholinomethyl)-4H-1,2,4-triazol-3-ylthio)-4-phenylquinolin-2(1H)-one;
6-chloro-4-phenylquinolin-2(1H)-one;
6-bromo-3-(5-(4-methoxyphenyl)-4,5-dihydroisoxazol-3-yl)-4-phenylquinolin-2(1H)-one;
6-chloro-3-(5-methoxy-1H-benzo[d]imidazol-2-ylthio)-4-phenylquinolin-2(1H)-one;
N-(6-bromo-2-oxo-4-phenyl-1,2-dihydroquinolin-3-yl)-2-chlorobenzamide;
N-(6-bromo-2-oxo-4-phenyl-1,2-dihydroquinolin-3-yl)-3-chlorobenzamide;
N-(6-bromo-2-oxo-4-phenyl-1,2-dihydroquinolin-3-yl)benzenesulfonamide;
N-(6-bromo-2-oxo-4-phenyl-1,2-dihydroquinolin-3-yl)-4-methylbenzenesulfonamide;
N-(6-bromo-2-oxo-4-phenyl-1,2-dihydroquinolin-3-yl)-3-methoxypropanamide;
4-methyl-N-(6-methyl-2-oxo-4-phenyl-1,2-dihydroquinolin-3-yl)benzenesulfonamide;
N-(((6-bromo-2-oxo-4-phenyl-1,2-dihydroquinolin-3-yl)methyl)-4-methylbenzenesulfonamide;
6-chloro-3-(1-(methylsulfonyl)-5-phenyl-4,5-dihydro-1H-pyrazol-3-yl)-4-phenylquinolin-2(1H)-one;
6-chloro-3-(6-oxo-4-propyl-1,6-dihydropyrimidin-2-ylthio)-4-phenylquinolin-2(1H)-one;
6-chloro-3-(5-methoxy-1H-benzo[d]imidazol-2-ylthio)-4-phenylquinolin-2(1H)-one;
3-(5-benzyl-6-methyl-4-oxo-4,5-dihydropyrimidin-2-ylthio)-6-chloro-4-phenylquinolin-2(1H)-one;
ethyl 2-(6-bromo-2-oxo-4-phenyl-1,2-dihydroquinolin-3-yl)acetate;
4-methyl-N-((6-methyl-2-oxo-4-phenyl-1,2-dihydroquinolin-3-yl)methyl)benzenesulfonamide;
6-chloro-4-phenyl-3-(phenylsulfonyl)quinolin-2(1H)-one;
N-(6-bromo-2-oxo-4-phenyl-1,2-dihydroquinolin-3-yl)-2-(diethylamino)acetamide;
2-(6-methyl-2-oxo-4-phenyl-1,2-dihydroquinolin-3-yl)acetic acid;
6-chloro-2-oxo-4-phenyl-1,2-dihydroquinolin-3-yl morpholine-4-carbodithioate;

6-chloro-2-oxo-4-phenyl-1,2-dihydroquinolin-3-yl diethylcarbamodithioate;
6-chloro-3-(1-methyl-1H-imidazol-2-ylthio)-4-phenylquinolin-2(1H)-one;
3-(benzo[d]thiazol-2-ylthio)-7-chloro-4-phenylquinolin-2(1H)-one;
3-(5-amino-1,3,4-thiadiazol-2-ylthio)-7-chloro-4-phenylquinolin-2(1H)-one;
7-chloro-3-(3-(methylthio)-1,2,4-thiadiazol-5-ylthio)-4-phenylquinolin-2(1H)-one;
1-(6-chloro-2-oxo-4-phenyl-1,2-dihydroquinolin-3-yl)-N-(3-(diethylamino)propyl)piperidine-3-carboxamide;
3-(6-chloro-2-oxo-4-phenyl-1,2-dihydroquinolin-3-yl)-N-methyl-5-phenyl-4,5-dihydro-1H-pyrazole-1-carbothioamide;
3-acetyl-6-bromo-4-phenylquinolin-2(1H)-one;
6-chloro-3-(5-methyl-1,3,4-thiadiazol-2-ylthio)-4-phenylquinolin-2(1H)-one;
6-chloro-4-phenyl-3-(4-propoxypyrimidin-2-ylthio)quinolin-2(1H)-one;
3-(4-amino-5-p-tolyl-4H-1,2,4-triazol-3-ylthio)-6-chloro-4-phenylquinolin-2(1H)-one;
3-(4-amino-6-oxo-1,6-dihydropyrimidin-2-ylthio)-6-chloro-4-phenylquinolin-2(1H)-one;
6-chloro-3-(1-methyl-1H-tetrazol-5-ylthio)-4-phenylquinolin-2(1H)-one;
1-(6-chloro-2-oxo-4-phenyl-1,2-dihydroquinolin-3-yl)quinoxalin-2(1H)-one;
3-(4-amino-6-oxo-1,6-dihydropyrimidin-2-ylthio)-4-phenylquinolin-2(1H)-one;
5-(2-methoxybenzyl)-5-methyl-3-(2-oxo-4-phenyl-1,2-dihydroquinolin-3-yl)imidazolidine-2,4-dione;
6-bromo-4-phenyl-3-(2,2,2-trifluoroacetyl)quinolin-2(1H)-one;
4-phenyl-3-(quinazolin-4-yloxy)quinolin-2(1H)-one;
3-(4-methyl-5-(trifluoromethyl)-4H-1,2,4-triazol-3-ylthio)-4-phenylquinolin-2(1H)-one;
3-(3-fluorophenoxy)-4-phenylquinolin-2(1H)-one;
3-(5-(4-fluorophenyl)-2H-tetrazol-2-yl)-4-phenylquinolin-2(1H)-one;
2-(6-(4-chlorophenyl)-8-methoxy-1-methyl-4H-benzo[f][1,2,4]triazolo[4,3-a][1,4]diazepin-4-yl)-N-ethylacetamide;
tert-butyl 2-(4-(4-chlorophenyl)-2,3,9-trimethyl-6H-thieno[3,2-f][1,2,4]triazolo[4,3-a][1,4]diazepin-6-yl)acetate;
2-methoxy-N-(3-methyl-2-oxo-1,2,3,4-tetrahydroquinazolin-6-yl)benzenesulfonamide.
N1,N3-bis(4-bromophenyl)malonamide;
N1,N3-bis(4-(3,5-dimethylisoxazol-4-yl)phenyl)malonamide;
6-(3,5-dimethylisoxazol-4-yl)-4-hydroxyquinolin-2(1H)-one;
4-chloro-6-(3,5-dimethylisoxazol-4-yl)quinolin-2(1H)-one;
4-(benzylamino)-6-(3,5-dimethylisoxazol-4-yl)quinolin-2(1H)-one;
4-(2-chlorobenzylamino)-6-(3,5-dimethylisoxazol-4-yl)quinolin-2(1H)-one;
6-(3,5-dimethylisoxazol-4-yl)-4-morpholinoquinolin-2(1H)-one;
6-(3,5-dimethylisoxazol-4-yl)-4-(piperidin-1-yl)quinolin-2(1H)-one; or
4-(benzylamino)-1-(benzylsulfonyl)-6-(3,5-dimethylisoxazol-4-yl)quinolin-2(1H)-one.

The compounds as provided herein may be used in the treatment of a variety of disorders and conditions and, as such, may be used in combination with a variety of other suitable therapeutic agents useful in the treatment or prophylaxis of those disorders or conditions. Thus, one embodiment of the present invention includes the administration of the compound of the present invention in combination with other therapeutic compounds. Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the present invention with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second. Such sequential administration may be close in time or remote in time.

Another aspect of the present invention includes combination therapy comprising administering to the subject a therapeutically or prophylactically effective amount of the compound of the present invention and one or more other therapy including chemotherapy, radiation therapy, gene therapy, or immunotherapy.

The compounds of the present invention can be used for the prevention or treatment of various conditions or disorders mediated by inhibiting bromodomain-containing proteins from binding acetylated proteins. The compounds and their pharmaceutical compositions are particularly useful in the treatment or prevention of various types of cancer, inflammation, obesity, metabolic, cardiovascular, neurodegenerative, psychiatric and infectious diseases. According to one embodiment, the compounds and their pharmaceutical compositions are particularly useful in the treatment or prevention of systemic or tissue inflammation, inflammatory responses to infection or hypoxia, cellular activation and proliferation, lipid metabolism, fibrosis and viral infections. According to one embodiment, the compounds and their pharmaceutical compositions are particularly useful in the treatment or prevention of a variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs. According to one embodiment, the compounds and their pharmaceutical compositions are particularly useful in the treatment or prevention of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs. According to one embodiment, the compounds and their pharmaceutical compositions are particularly useful in the treatment or prevention of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. According to one embodiment, the compounds and their pharmaceutical compositions are particularly useful in the treatment or prevention of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastrointestinal or peripheral limb embolism. According to one embodiment, the compounds and their pharmaceutical compositions are particularly useful in the treatment or prevention of disorders of lipid metabolism via the regulation of APO-A1 such as hypercholesterolemia, atherosclerosis and Alzheimer's disease. According to one embodiment, the compounds and their pharmaceutical compositions are particularly useful in the treatment or prevention of fibrotic conditions such as idiopathic pulmonary fibrosis, renal fibrosis, post-operative stricture, keloid formation, scleroderma and cardiac fibrosis. According to one embodiment, the compounds and their pharmaceutical compositions are particularly useful in the treatment or prevention of viral infections such as herpes virus, human papilloma virus, adenovirus and poxvirus and other DNA viruses. According to one embodiment, the compounds and their pharmaceutical compositions are particularly useful in the treatment or prevention of diseases associated with systemic inflammatory response syndrome include sepsis, burns, pancreatitis, major trauma, haemorrhage and ischaemia. According to one embodiment, the compounds and their pharmaceutical compositions are particularly useful in the treatment or prevention of SIRS, the onset of shock, multi-organ dysfunction syndrome, which includes the onset of acute lung injury, ARDS, acute renal, hepatic, cardiac and gastrointestinal injury and mortality. According to one embodiment, the compounds and their pharmaceutical compositions are particularly useful in the treatment or prevention of sepsis, sepsis syndrome, septic shock and endotoxaemia, acute or chronic pancreatitis, herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus and for the treatment of Human papilloma virus infections of skin or cervical epithelia. According to one embodiment, the compounds and their pharmaceutical compositions are particularly useful in the treatment or prevention of various forms of cancer, leukemias and lymphomas including acute myeloid luekiemia, Burkitt's lymphoma, multiple myeloma, T-cell lymphoblastic leukemia and other hemotological cancers that involve translocations of mixed-lineage leukemia gene (MLL); solid tumors such as hepatocellular carcinoma, glioblastoma, neuroblastoma, NUT midline carcinoma, sarcoma, breast, colorectal, lung, pancreatic and prostate cancer; osteoarthritis and rheumatoid arthritis; Alzheimer's disease; and HIV infection.

The present invention also provides a method for the synthesis of compounds useful as intermediates in the preparation of compounds of the present invention along with methods for their preparation. The compounds can be prepared according to the methods described below using readily available starting materials and reagents. In these reactions, variants may be employed which are themselves known to those of ordinary skill in this art but are not described in detail here. Those skilled in the art of organic synthesis will appreciate that there exist multiple means of producing compounds of the present invention. Illustrative synthetic methods, including those directed to specific, selected compounds noted in Tables 1, 2, 3, 4, 5, and 6 are set forth herein.

TABLE 1

| Compound | Structure |
|---|---|
| 1. | 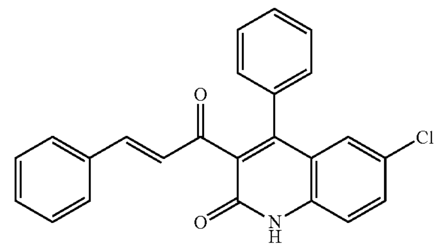 [SMILES: O=C(/C=C/c1ccccc1)c1c(-c2ccccc2)c2cc(Cl)ccc2[nH]c1=O] |
| 2. | 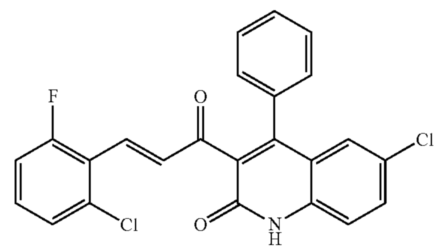 [SMILES: O=C(/C=C/c1c(F)cccc1Cl)c1c(-c2ccccc2)c2cc(Cl)ccc2[nH]c1=O] |
| 3. | 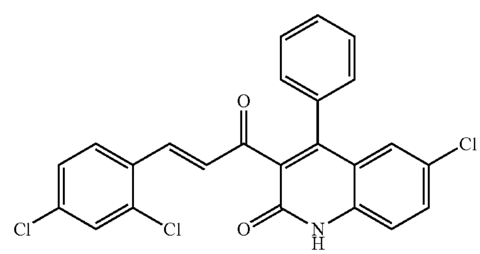 [SMILES: O=C(/C=C/c1ccc(Cl)cc1Cl)c1c(-c2ccccc2)c2cc(Cl)ccc2[nH]c1=O] |
| 4. | 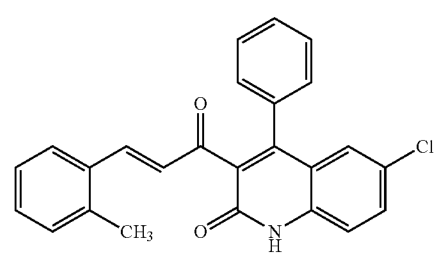 [SMILES: Cc1ccccc1/C=C/C(=O)c1c(-c2ccccc2)c2cc(Cl)ccc2[nH]c1=O] |
| 5. | 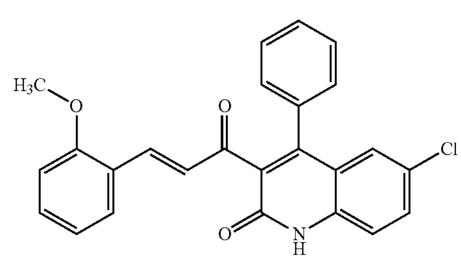 [SMILES: COc1ccccc1/C=C/C(=O)c1c(-c2ccccc2)c2cc(Cl)ccc2[nH]c1=O] |

TABLE 1-continued

| Compound | Structure |
|---|---|
| 6. | (structure) |
| 7. | (structure) |
| 8. | (structure) |
| 9. | (structure) |
| 10. | (structure) |
| 11. | (structure) |
| 12. | (structure) |
| 13. | (structure) |
| 14. | (structure) |
| 15. | (structure) |
| 16. | (structure) |
| 17. | (structure) |

TABLE 1-continued

| Compound | Structure |
|---|---|
| 18. | (structure) |
| 19. | (structure) |
| 20. | (structure) |
| 21. | (structure) |
| 22. | (structure) |
| 23. | (structure) |
| 24. | (structure) |
| 25. | (structure) |
| 26. | (structure) |
| 27. | (structure) |
| 28. | (structure) |
| 29. | (structure) |

TABLE 1-continued

| Compound | Structure |
|---|---|
| 30. | 3-(3,5-dimethylisoxazol-4-yl)-6-chloro-4-(4-methylpiperazin-1-yl)quinolin-2(1H)-one |
| 31. | 3-(3,5-dimethylisoxazol-4-yl)-6-chloro-4-(pyridin-4-yl)quinolin-2(1H)-one |
| 32. | 3-(3,5-dimethylisoxazol-4-yl)-6-chloro-4-(pyridin-3-yl)quinolin-2(1H)-one |
| 33. | 3-(3,5-dimethylisoxazol-4-yl)-6-chloro-4-(pyridin-2-yl)quinolin-2(1H)-one |
| 34. | 3-(3,5-dimethylisoxazol-4-yl)-6-chloro-4-(1H-pyrrol-1-yl)quinolin-2(1H)-one |
| 35. | 3-(3,5-dimethylisoxazol-4-yl)-6-chloro-4-(furan-3-yl)quinolin-2(1H)-one |
| 36. | 3-(5-methylisoxazol-4-yl)-6-chloro-4-(isoxazol-4-yl)quinolin-2(1H)-one |
| 37. | 3-(isoxazol-4-yl)-6-chloro-4-(pyridin-4-yl)quinolin-2(1H)-one |
| 38. | 3-(1H-pyrazol-4-yl)-6-chloro-4-(pyridin-4-yl)quinolin-2(1H)-one |
| 39. | 3-(furan-3-yl)-6-chloro-4-(pyridin-4-yl)quinolin-2(1H)-one |
| 40. | 3-(thiophen-3-yl)-6-chloro-4-(pyridin-4-yl)quinolin-2(1H)-one |
| 41. | 3-(1H-imidazol-4-yl)-6-chloro-4-(pyridin-4-yl)quinolin-2(1H)-one |

TABLE 1-continued

| Compound | Structure |
|---|---|
| 42. | 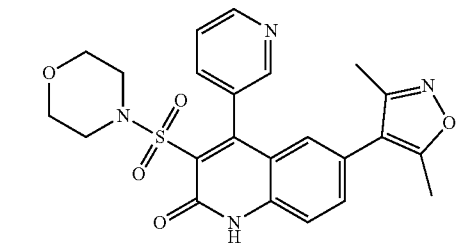 [SMILES: Cc1noc(C)c1-c1ccc2[nH]c(=O)c(S(=O)(=O)N3CCOCC3)c(-c3cccnc3)c2c1] |
| 43. | 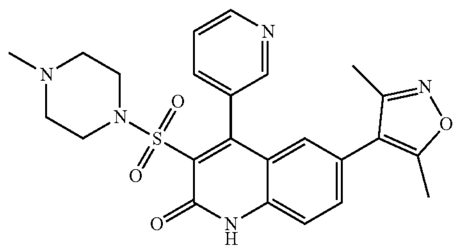 [SMILES: Cc1noc(C)c1-c1ccc2[nH]c(=O)c(S(=O)(=O)N3CCN(C)CC3)c(-c3cccnc3)c2c1] |
| 44. | 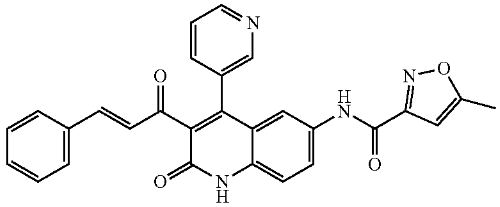 [SMILES: Cc1cc(C(=O)Nc2ccc3[nH]c(=O)c(C(=O)/C=C/c4ccccc4)c(-c4cccnc4)c3c2)no1] |
| 45. | 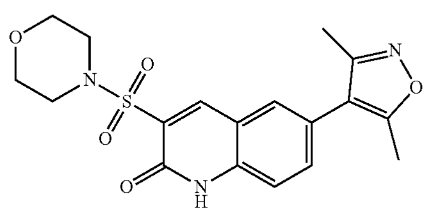 [SMILES: Cc1noc(C)c1-c1ccc2[nH]c(=O)c(S(=O)(=O)N3CCOCC3)cc2c1] |
| 46. | 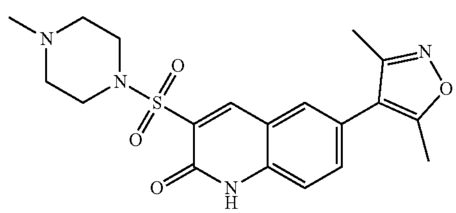 [SMILES: Cc1noc(C)c1-c1ccc2[nH]c(=O)c(S(=O)(=O)N3CCN(C)CC3)cc2c1] |
| 47. | 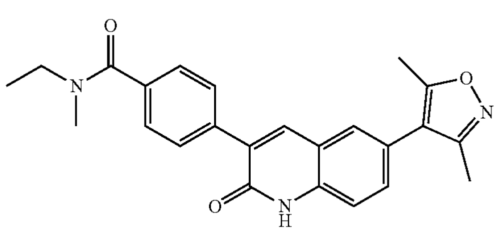 [SMILES: CCN(C)C(=O)c1ccc(-c2cc3cc(-c4c(C)noc4C)ccc3[nH]c2=O)cc1] |
| 48. | 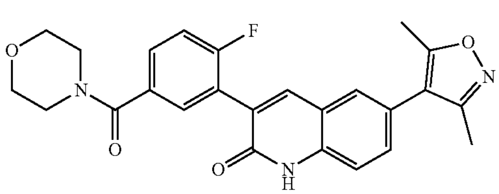 [SMILES: Cc1noc(C)c1-c1ccc2[nH]c(=O)c(-c3cc(C(=O)N4CCOCC4)ccc3F)cc2c1] |
| 49. | |
| 50. | |
| 51. | |
| 52. | |
| 53. | |
| 54. | |
| 55. | |

TABLE 1-continued
| Compound | Structure |
|---|---|
| 56. | 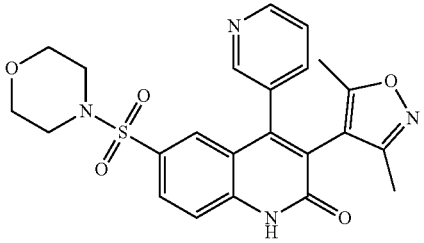 [SMILES: Cc1noc(C)c1-c1c(-c2cccnc2)c2cc(S(=O)(=O)N3CCOCC3)ccc2[nH]c1=O] |
| 57. | 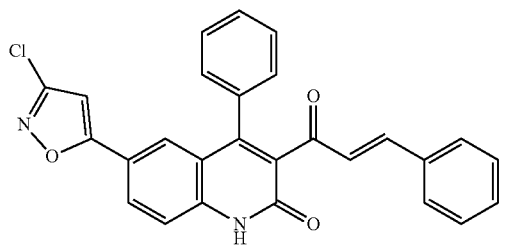 |
| 58. | 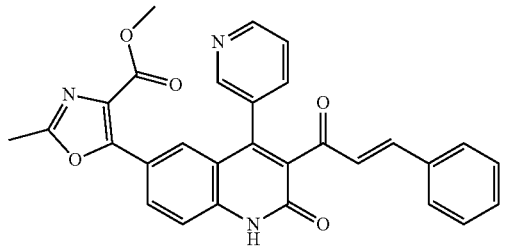 |
| 59. | 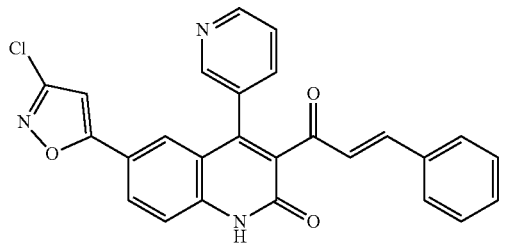 [SMILES: O=C(/C=C/c1ccccc1)c1c(-c2ccccc2)c2cc(-c3cc(Cl)no3)ccc2[nH]c1=O] |
| 60. | 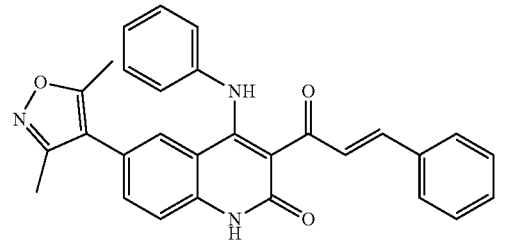 [SMILES: Cc1noc(C)c1-c1ccc2[nH]c(=O)c(C(=O)/C=C/c3ccccc3)c(Nc3ccccc3)c2c1] |
| 61. | 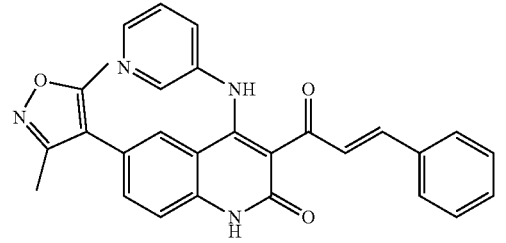 |
TABLE 1-continued
| Compound | Structure |
|---|---|
| 62. | 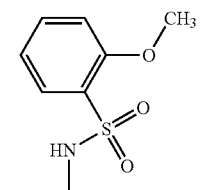 |
| 63. | 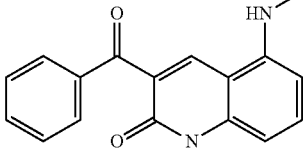 |
| 64. | 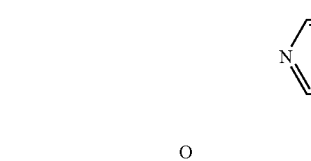 |
| 65. | 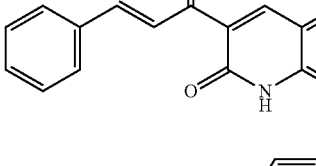 |
| 66. | 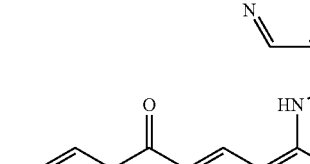 |

TABLE 1-continued
| Compound | Structure |
|---|---|
| 67. | 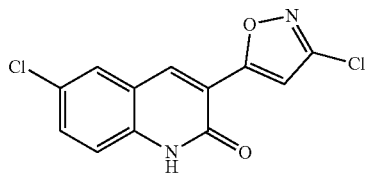 [SMILES: O=c1[nH]c2ccc(Cl)cc2cc1-c1cc(Cl)no1] |
| 68. | 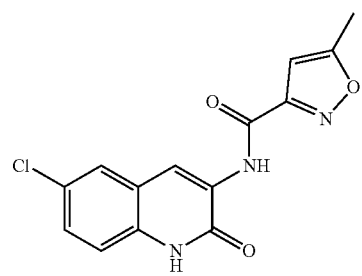 [SMILES: Cc1cc(C(=O)Nc2cc3cc(Cl)ccc3[nH]c2=O)no1] |
| 69. | 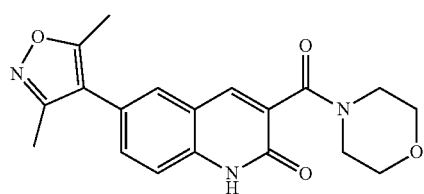 [SMILES: Cc1noc(C)c1-c1ccc2[nH]c(=O)c(C(=O)N3CCOCC3)cc2c1] |
| 70. | 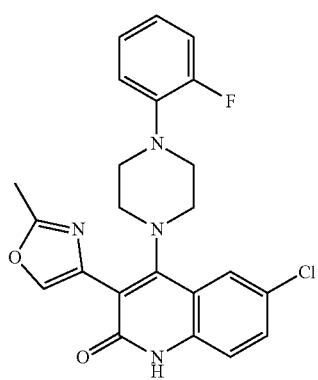 [SMILES: Cc1nc(-c2c(N3CCN(c4ccccc4F)CC3)c3cc(Cl)ccc3[nH]c2=O)co1] |
| 71. | 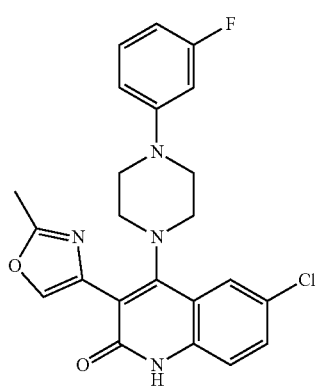 [SMILES: Cc1nc(-c2c(N3CCN(c4cccc(F)c4)CC3)c3cc(Cl)ccc3[nH]c2=O)co1] |
| 72. | 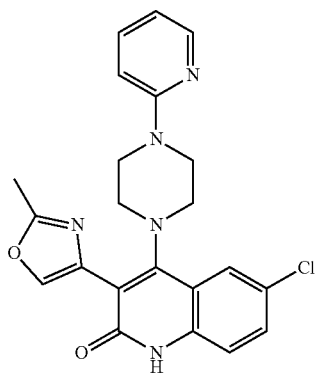 [SMILES: Cc1nc(-c2c(N3CCN(c4ccccn4)CC3)c3cc(Cl)ccc3[nH]c2=O)co1] |
| 73. | 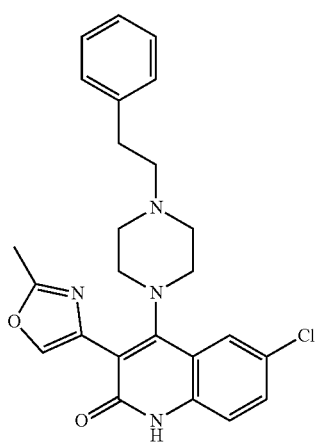 [SMILES: Cc1nc(-c2c(N3CCN(CCc4ccccc4)CC3)c3cc(Cl)ccc3[nH]c2=O)co1] |
| 74. | 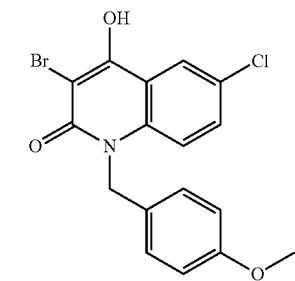 [SMILES: COc1ccc(Cn2c(=O)c(Br)c(O)c3cc(Cl)ccc32)cc1] |
| 75. | 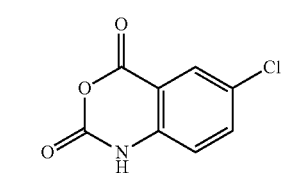 [SMILES: O=c1[nH]c2ccc(Cl)cc2c(=O)o1] |
| 76. | 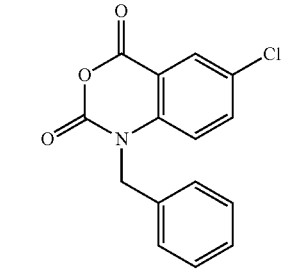 [SMILES: O=c1oc(=O)n(Cc2ccccc2)c2ccc(Cl)cc12] |

TABLE 1-continued
| Compound | Structure |
|---|---|
| 77. | 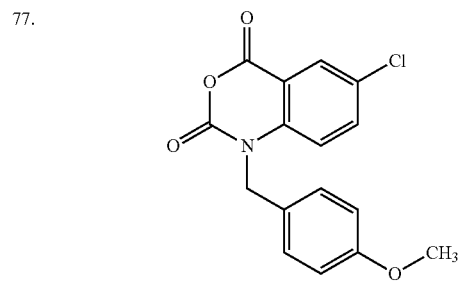 |
| 78. | 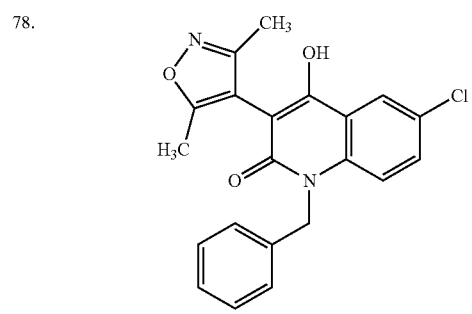 |
| 79. | 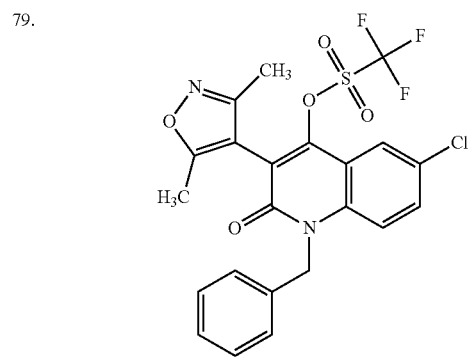 |
| 80. | 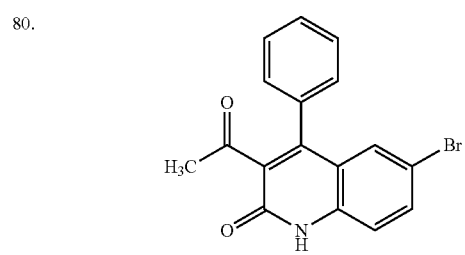 |
| 81. | 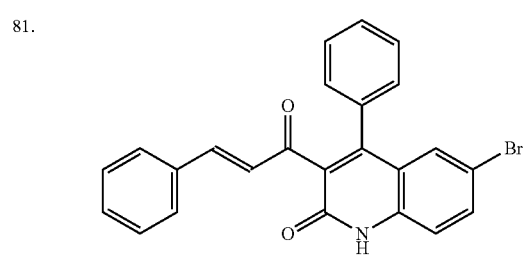 |
| 82. | 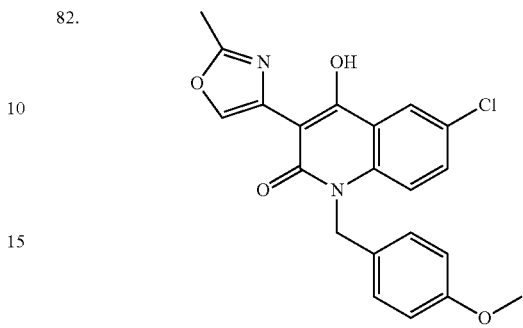 |
| 83. | 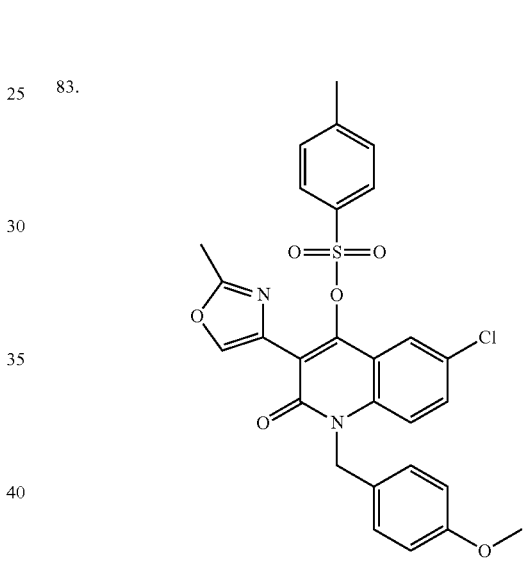 |
| 84. | 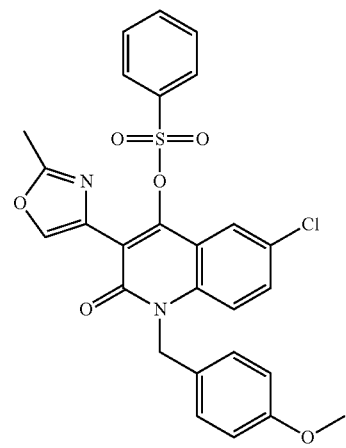 |

TABLE 1-continued
| Compound | Structure |
|---|---|
| 85. | 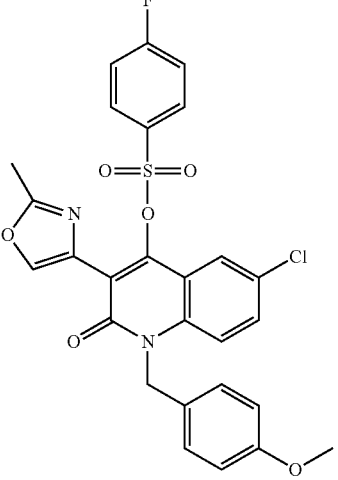 [SMILES: COc1ccc(Cn2c(=O)c(-c3coc(C)n3)c(OS(=O)(=O)c3ccc(C)cc3)c3cc(Cl)ccc32)cc1] |
| 86. | 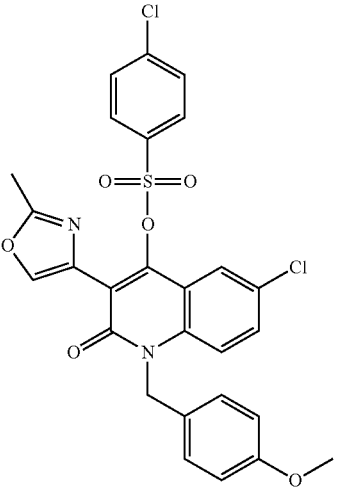 [SMILES: COc1ccc(Cn2c(=O)c(-c3coc(C)n3)c(OS(=O)(=O)c3ccc(Cl)cc3)c3cc(Cl)ccc32)cc1] |
| 87. | 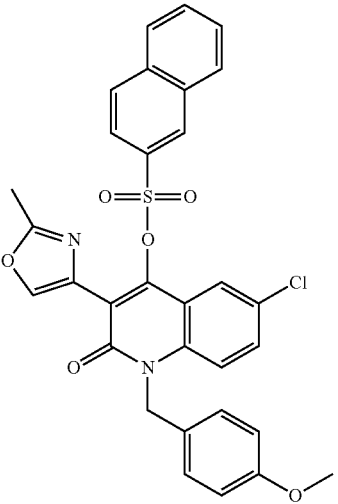 [SMILES: COc1ccc(Cn2c(=O)c(-c3coc(C)n3)c(OS(=O)(=O)c3ccc4ccccc4c3)c3cc(Cl)ccc32)cc1] |
| 88. | 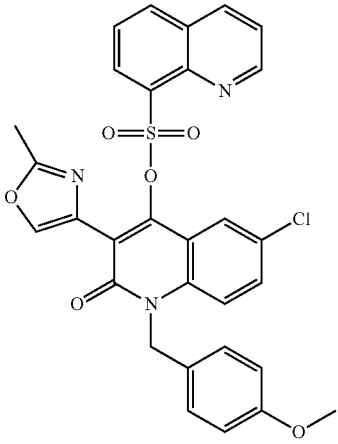 [SMILES: COc1ccc(Cn2c(=O)c(-c3coc(C)n3)c(OS(=O)(=O)c3cccc4cccnc34)c3cc(Cl)ccc32)cc1] |
| 89. | 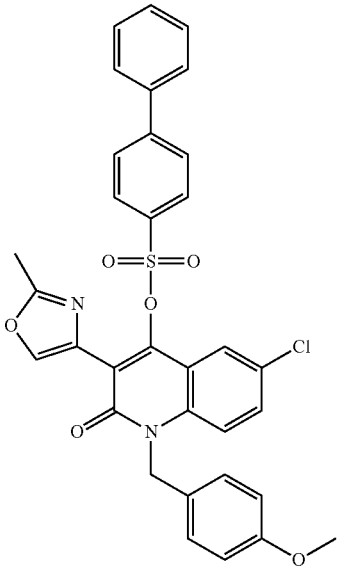 [SMILES: COc1ccc(Cn2c(=O)c(-c3coc(C)n3)c(OS(=O)(=O)c3ccc(-c4ccccc4)cc3)c3cc(Cl)ccc32)cc1] |
| 90. | 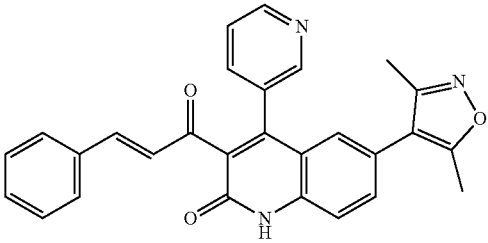 [SMILES: Cc1noc(C)c1-c1ccc2[nH]c(=O)c(C(=O)/C=C/c3ccccc3)c(-c3cccnc3)c2c1] |
| 91. | 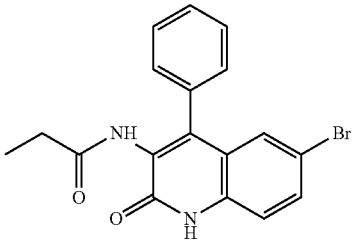 [SMILES: CCC(=O)Nc1c(-c2ccccc2)c2cc(Br)ccc2[nH]c1=O] |

TABLE 1-continued

| Compound | Structure |
|---|---|
| 92. | (structure) |
| 93. | (structure) |
| 94. | (structure) |
| 95. | (structure) |
| 96. | (structure) |
| 97. | (structure) |
| 98. | (structure) |
| 99. | (structure) |
| 100. | (structure) |
| 101. | (structure) |
| 102. | (structure) |
| 103. | (structure) |

TABLE 1-continued
| Compound | Structure |
|---|---|
| 104. | 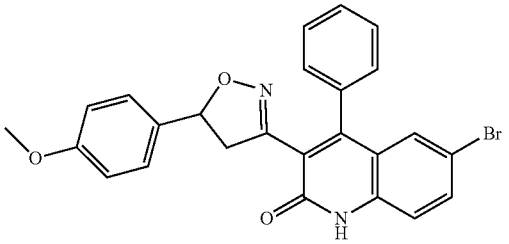 [SMILES: COc1ccc(C2CC(c3c(-c4ccccc4)c4cc(Br)ccc4[nH]c3=O)=NO2)cc1] |
| 105. | 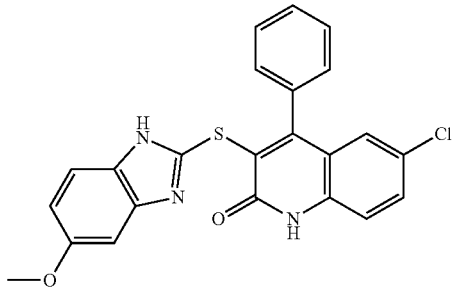 [SMILES: COc1ccc2[nH]c(Sc3c(-c4ccccc4)c4cc(Cl)ccc4[nH]c3=O)nc2c1] |
| 106. | 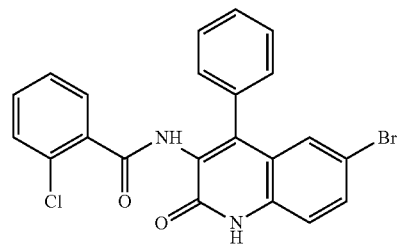 [SMILES: O=C(Nc1c(-c2ccccc2)c2cc(Br)ccc2[nH]c1=O)c1ccccc1Cl] |
| 107. | 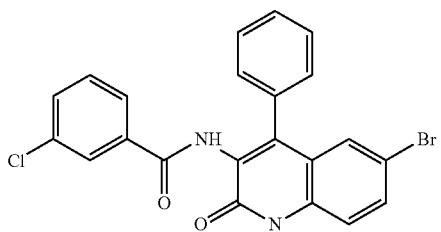 |
| 108. | 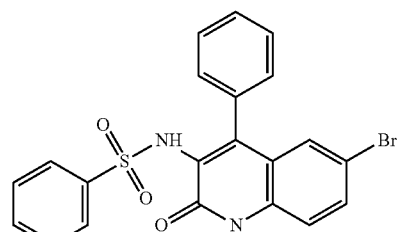 |
| 109. | 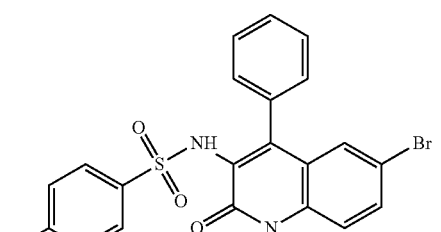 |
| 110. | 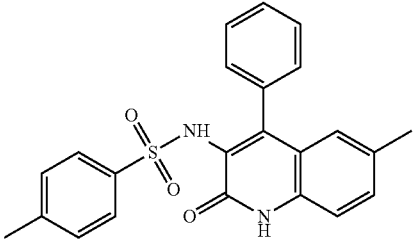 |
| 111. | 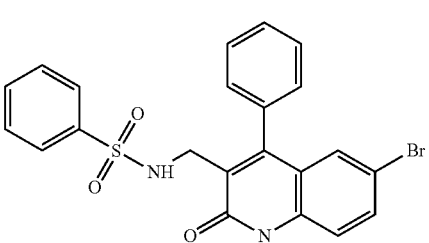 |
| 112. | 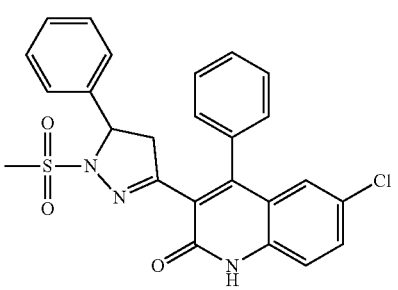 [SMILES: CS(=O)(=O)N1N=C(c2c(-c3ccccc3)c3cc(Cl)ccc3[nH]c2=O)CC1c1ccccc1] |
| 113. | 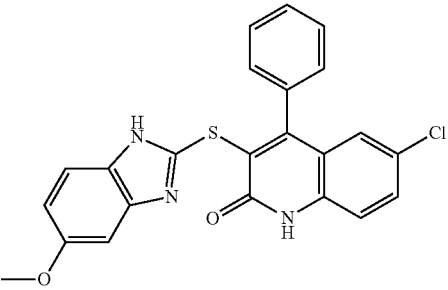 [SMILES: COc1ccc2[nH]c(Sc3c(-c4ccccc4)c4cc(Cl)ccc4[nH]c3=O)nc2c1] |
| 114. | |

TABLE 1-continued
| Compound | Structure |
|---|---|
| 115. | 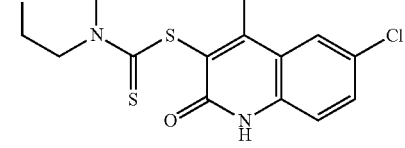 |
| 116. | |
| 117. | |
| 118. | |
| 119. | |
| 120. | |ـ
| Compound | Structure |
|---|---|
| 121. | 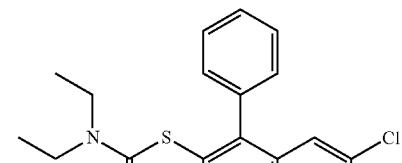 |
| 122. | |
| 123. | |
| 124. | |
| 125. | |
| 126. | |

TABLE 1-continued
| Compound | Structure |
|---|---|
| 127. | 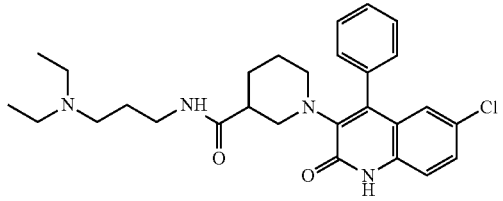 [SMILES: CCN(CC)CCCNC(=O)C1CCCN(c2c(-c3ccccc3)c3cc(Cl)ccc3[nH]c2=O)C1] |
| 128. | 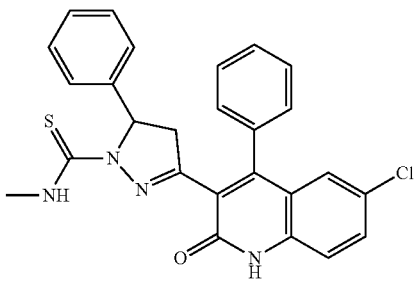 [SMILES: CNC(=S)N1N=C(c2c(-c3ccccc3)c3cc(Cl)ccc3[nH]c2=O)CC1c1ccccc1] |
| 129. | 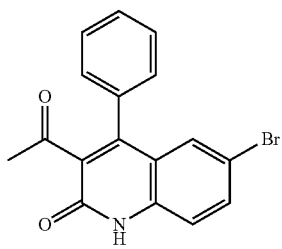 [SMILES: CC(=O)c1c(-c2ccccc2)c2cc(Br)ccc2[nH]c1=O] |
| 130. | 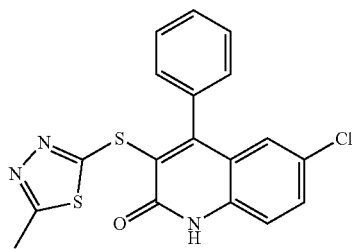 [SMILES: Cc1nnc(Sc2c(-c3ccccc3)c3cc(Cl)ccc3[nH]c2=O)s1] |
| 131. | 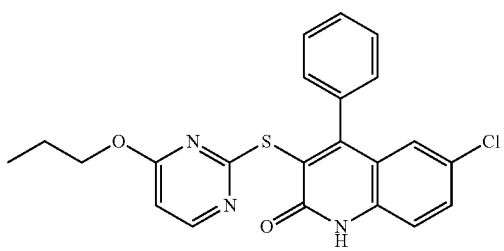 [SMILES: CCCOc1ccnc(Sc2c(-c3ccccc3)c3cc(Cl)ccc3[nH]c2=O)n1] |
| 132. | 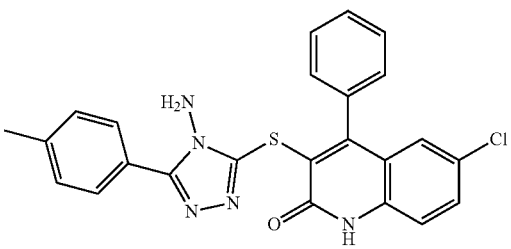 [SMILES: Cc1ccc(-c2nnc(Sc3c(-c4ccccc4)c4cc(Cl)ccc4[nH]c3=O)n2N)cc1] |
| 133. | 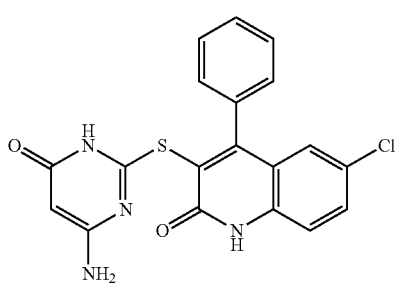 [SMILES: Nc1cc(=O)[nH]c(Sc2c(-c3ccccc3)c3cc(Cl)ccc3[nH]c2=O)n1] |
| 134. | 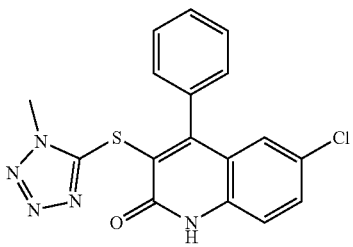 [SMILES: Cn1nnnc1Sc1c(-c2ccccc2)c2cc(Cl)ccc2[nH]c1=O] |
| 135. | 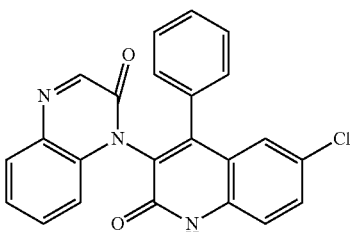 |
| 136. | 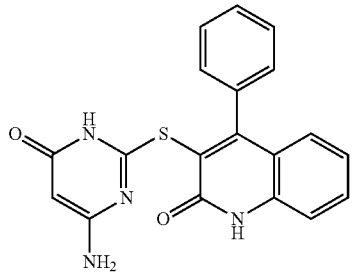 [SMILES: Nc1cc(=O)[nH]c(Sc2c(-c3ccccc3)c3ccccc3[nH]c2=O)n1] |

TABLE 1-continued
| Compound | Structure |
|---|---|
| 137. | 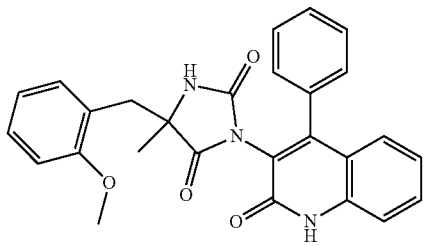 [SMILES: COc1ccccc1CC1(C)NC(=O)N(c2c(-c3ccccc3)c3ccccc3[nH]c2=O)C1=O] |
| 138. | 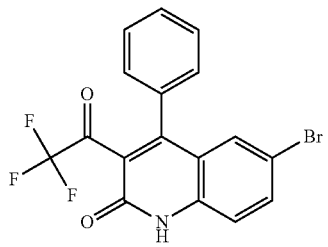 [SMILES: O=C(c1c(-c2ccccc2)c2cc(Br)ccc2[nH]c1=O)C(F)(F)F] |
| 139. | 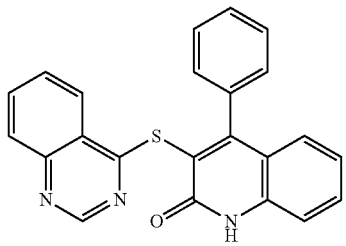 [SMILES: O=c1[nH]c2ccccc2c(-c2ccccc2)c1Sc1ncnc2ccccc12] |
| 140. | 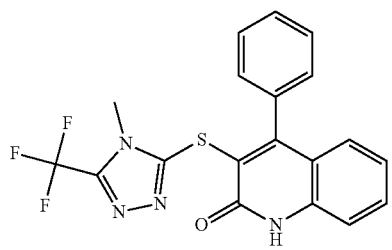 [SMILES: Cn1c(Sc2c(-c3ccccc3)c3ccccc3[nH]c2=O)nnc1C(F)(F)F] |
| 141. | 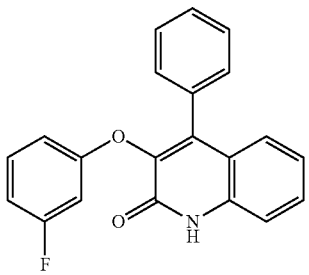 [SMILES: O=c1[nH]c2ccccc2c(-c2ccccc2)c1Oc1cccc(F)c1] |
| 142. | 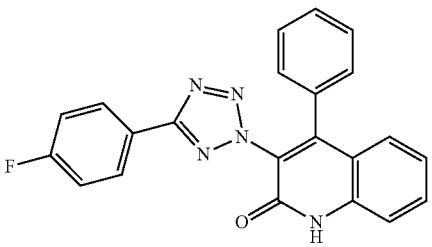 [SMILES: O=c1[nH]c2ccccc2c(-c2ccccc2)c1-n1nnc(-c2ccc(F)cc2)n1] |
| 143. | 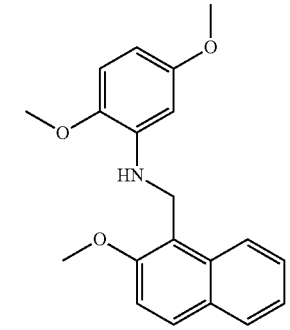 [SMILES: COc1ccc(OC)c(NCc2c(OC)ccc3ccccc23)c1] |
| 144. | 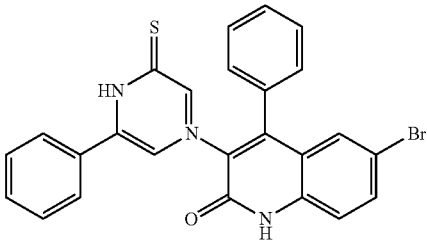 |
| 145. | 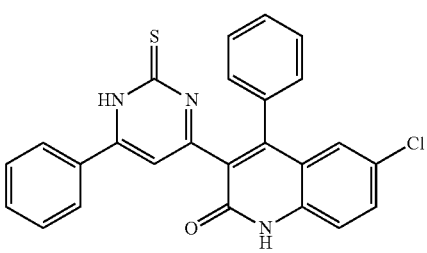 [SMILES: O=c1[nH]c2ccc(Cl)cc2c(-c2ccccc2)c1-c1cc(-c2ccccc2)[nH]c(=S)n1] |

TABLE 2

Compounds of Formula 1A

Formula 1A

| $R_{1A}$ | $R_{2A}$ | $R_{3A}$ | $R_{4A}$ | $R_{5A}$ | $R_{6A}$ | $L_{1A}$ | Position, $L_{2A}$ | $L_{3A}$ |
|---|---|---|---|---|---|---|---|---|
| 3,5-dimethylisoxazol-4-yl | H | —NHC(O)OCH₂Ph | Ph | —OH | H | —CH₂— | 3, —CH₂CH₂— | — |
| 3,5-dimethylisoxazol-4-yl | H | —NHC(O)OCH₂Ph | Ph | —OMe | H | —CH₂— | 3, —CH₂CH₂— | — |
| 3,5-dimethylisoxazol-4-yl | H | —NHC(O)OCH₂Ph | Ph | —OH | H | —CH₂CH₂— | 3, —CH₂CH₂— | — |
| 3,5-dimethylisoxazol-4-yl | H | —NHC(O)OCH₂Ph | Ph | —OMe | H | —CH₂CH₂— | 3, —CH₂CH₂— | — |
| 3,5-dimethylisoxazol-4-yl | H | —NHC(O)OEt | Ph | —OH | H | —CH₂— | 3, —CH₂CH₂— | — |
| 3,5-dimethylisoxazol-4-yl | H | —NHC(O)OEt | Ph | —OMe | H | —CH₂— | 3, —CH₂CH₂— | — |
| 3,5-dimethylisoxazol-4-yl | H | —NHC(O)OEt | Ph | —OH | H | —CH₂CH₂— | 3, —CH₂CH₂— | — |
| 3,5-dimethylisoxazol-4-yl | H | —NHC(O)OEt | Ph | —OMe | H | —CH₂CH₂— | 3, —CH₂CH₂— | — |

TABLE 2-continued

Compounds of Formula 1A

Formula 1A

| R$_{1A}$ | R$_{2A}$ | R$_{3A}$ | R$_{4A}$ | R$_{5A}$ | R$_{6A}$ | L$_{1A}$ | Position, L$_{2A}$ | L$_{3A}$ |
|---|---|---|---|---|---|---|---|---|
| 3,5-dimethylisoxazol-4-yl | H | —NHC(O)NHEt | Ph | —OH | H | —CH$_2$— | 3, —CH$_2$CH$_2$— | — |
| 3,5-dimethylisoxazol-4-yl | H | —NHC(O)NHEt | Ph | —OMe | H | —CH$_2$— | 3, —CH$_2$CH$_2$— | — |
| 3,5-dimethylisoxazol-4-yl | H | —NHC(O)NHEt | Ph | —OH | H | —CH$_2$CH$_2$— | 3, —CH$_2$CH$_2$— | — |
| 3,5-dimethylisoxazol-4-yl | H | —NHC(O)NHEt | Ph | —OMe | H | —CH$_2$CH$_2$— | 3, —CH$_2$CH$_2$— | — |
| 3,5-dimethylisoxazol-4-yl | H | —NHC(O)NHEt | Ph | —OH | H | —CH$_2$— | 3, —CH$_2$CH$_2$— | — |
| 3,5-dimethylisoxazol-4-yl | H | —NHC(O)NHEt | Ph | —OMe | H | —CH$_2$— | 3, —CH$_2$CH$_2$— | — |
| 3,5-dimethylisoxazol-4-yl | H | —NHC(O)NHEt | Ph | —OH | H | —CH$_2$CH$_2$— | 3, —CH$_2$CH$_2$— | — |
| 3,5-dimethylisoxazol-4-yl | H | —NHC(O)NHEt | Ph | —OMe | H | —CH$_2$CH$_2$— | 3, —CH$_2$CH$_2$— | — |

TABLE 2-continued
Compounds of Formula 1A
Formula 1A
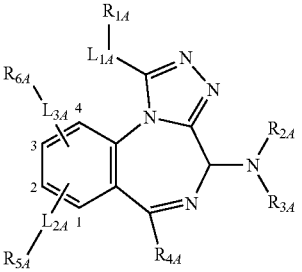
| R1A | R2A | R3A | R4A | R5A | R6A | L1A | Position, L2A | L3A |
|---|---|---|---|---|---|---|---|---|
| 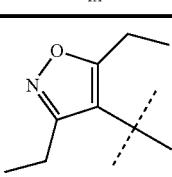 | H | 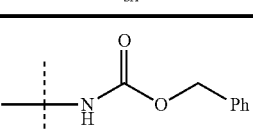 | Ph | —OH | H | —CH2— | 3, —CH2CH2— | — |
| 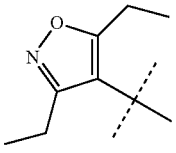 | H | 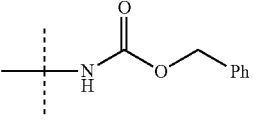 | Ph | —OMe | H | —CH2— | 3, —CH2CH2— | — |
| 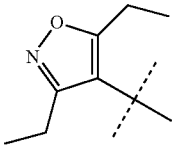 | H | 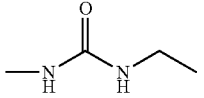 | Ph | —OH | H | —CH2CH2— | 3, —CH2CH2— | — |
| 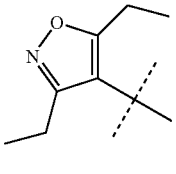 | H | 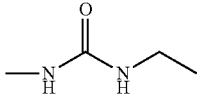 | Ph | —OMe | H | —CH2CH2— | 3, —CH2CH2— | — |
| 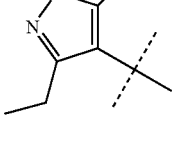 | H | 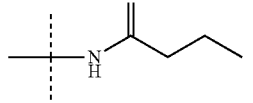 | Ph | —OH | H | —CH2— | 3, —CH2CH2— | — |
| 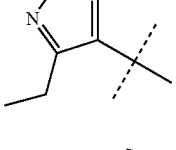 | H | 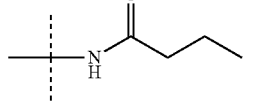 | Ph | —OMe | H | —CH2— | 3, —CH2CH2— | — |
| 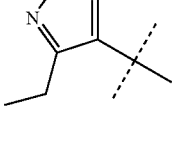 | H | 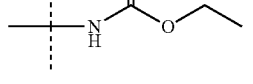 | Ph | —OH | H | —CH2CH2— | 3, —CH2CH2— | — |

TABLE 2-continued

Compounds of Formula 1A

Formula 1A

| R$_{1A}$ | R$_{2A}$ | R$_{3A}$ | R$_{4A}$ | R$_{5A}$ | R$_{6A}$ | L$_{1A}$ | Position, L$_{2A}$ | L$_{3A}$ |
|---|---|---|---|---|---|---|---|---|
| 3,5-diethylisoxazol-4-yl | H | ethyl carbamate | Ph | —OMe | H | —CH$_2$CH$_2$— | 3, —CH$_2$CH$_2$— | — |
| 3,5-dimethylisoxazol-4-yl | H | benzyl carbamate | Ph | —NHCOCH$_3$ | H | —CH$_2$— | 3, —CH$_2$CH$_2$— | CH$_2$ |
| 3,5-diethylisoxazol-4-yl | H | benzyl carbamate | Ph | —NHCOCH$_3$ | H | —CH$_2$— | 3, —CH$_2$CH$_2$— | CH$_2$ |
| 3,5-dimethylisoxazol-4-yl | H | ethyl urea | Ph | —NHCOCH$_3$ | H | —CH$_2$CH$_2$— | 3, —CH$_2$CH$_2$— | CH$_2$ |
| 3,5-diethylisoxazol-4-yl | H | ethyl urea | Ph | —NHCOCH$_3$ | H | —CH$_2$CH$_2$— | 3, —CH$_2$CH$_2$— | CH$_2$ |
| 3,5-dimethylisoxazol-4-yl | H | butyramide | Ph | —NHCOCH$_3$ | H | —CH$_2$— | 3, —CH$_2$CH$_2$— | CH$_2$ |
| 3,5-diethylisoxazol-4-yl | H | butyramide | Ph | —NHCOCH$_3$ | H | —CH$_2$— | 3, —CH$_2$CH$_2$— | CH$_2$ |
| 3,5-dimethylisoxazol-4-yl | H | ethyl carbamate | Ph | —NHCOCH$_3$ | H | —CH$_2$CH$_2$— | 3, —CH$_2$CH$_2$— | CH$_2$ |

TABLE 2-continued

Compounds of Formula 1A

Formula 1A

| $R_{1A}$ | $R_{2A}$ | $R_{3A}$ | $R_{4A}$ | $R_{5A}$ | $R_{6A}$ | $L_{1A}$ | Position, $L_{2A}$ | $L_{3A}$ |
|---|---|---|---|---|---|---|---|---|
| 3,5-diethylisoxazol-4-yl | H | ethyl carbamate (—NHC(O)OEt) | Ph | —NHCOCH$_3$ | H | —CH$_2$CH$_2$— | 3, —CH$_2$CH$_2$— | CH$_2$ |
| Ph | H | butanamide (—NHC(O)CH$_2$CH$_2$CH$_3$) | Ph | —NHCOCH$_3$ | H | —CH$_2$— | 3, —CH$_2$CH$_2$— | CH$_2$ |
| Ph | H | butanamide (—NHC(O)CH$_2$CH$_2$CH$_3$) | Ph | —NHCOCH$_3$ | H | —CH$_2$— | 3, —CH$_2$CH$_2$— | CH$_2$ |
| Ph | H | ethyl carbamate (—NHC(O)OEt) | Ph | —NHCOCH$_3$ | H | —CH$_2$CH$_2$— | 3, —CH$_2$CH$_2$— | CH$_2$ |
| Ph | H | ethyl carbamate (—NHC(O)OEt) | Ph | —NHCOCH$_3$ | H | —CH$_2$CH$_2$— | 3, —CH$_2$CH$_2$— | CH$_2$ |

TABLE 3

Formula 1B

| $R_{1B}$ | $R_{2B}$ | $R_{3B}$ | $R_{4B}$ | $R_{5B}$ | $X_B$ | $Y_B$ | $L_B$ |
|---|---|---|---|---|---|---|---|
| H | 1-(pyridin-2-yl)ethyl | —CH$_3$ | —CH$_3$ | —OH | =O | —O— | —CH$_2$CH$_2$— |

TABLE 3-continued

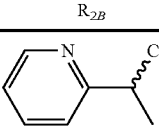

Formula 1B

| $R_{1B}$ | $R_{2B}$ | $R_{3B}$ | $R_{4B}$ | $R_{5B}$ | $X_B$ | $Y_B$ | $L_B$ |
|---|---|---|---|---|---|---|---|
| H | 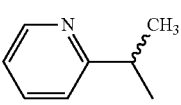 | —CH₃ | —CH₃ | —CONH₂ | =O | —O— | —CH₂— |
| H | 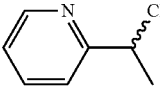 | —CH₃ | —CH₃ | —OH | =O | —N(CH)₃— | —CH₂CH₂— |
| H | 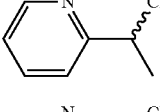 | —CH₃ | —CH₃ | —CONH₂ | =O | —N(CH)₃— | —CH₂— |
| H | 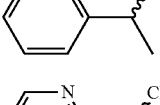 | —CH₃ | —CH₃ | —OH | =O | —N(CH₃)CO— | —CH₂CH₂— |
| H | 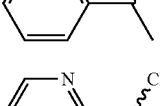 | —CH₃ | —CH₃ | —CONH₂ | =O | —N(CH₃)CO— | —CH₂— |
| H | 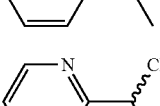 | —CH₃ | —CH₃ | —OCH₃ | =O | —N(CH₃)CO— | —CH₂CH₂— |
| H | 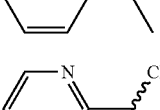 | —CH₃ | —CH₃ | —CON(CH₃)— | =O | —N(CH₃)CO— | —CH₂— |
| —CH₂CH₂OH | 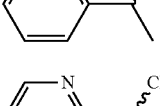 | —CH₃ | —CH₃ | —OH | =O | —O— | —CH₂CH₂— |
| —CH₂CH₂OCH₃ | 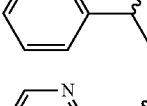 | —CH₃ | —CH₃ | —CONH₂ | =O | —O— | —CH₂— |
| —CH₂CONH₂ | 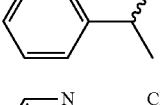 | —CH₃ | —CH₃ | —OH | =O | —N(CH)₃— | —CH₂CH₂— |
| —CH₂CH₂OH | 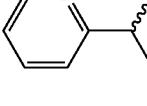 | —CH₃ | —CH₃ | —CONH₂ | =O | —N(CH)₃— | —CH₂— |
| —CH₂CH₂OCH₃ |  | —CH₃ | —CH₃ | —OH | =O | —N(CH₃)CO— | —CH₂CH₂— |

TABLE 3-continued

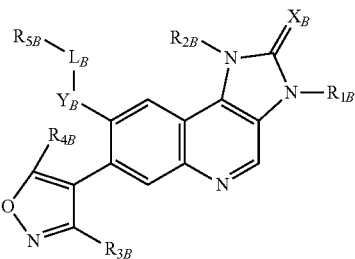

Formula 1B

| $R_{1B}$ | $R_{2B}$ | $R_{3B}$ | $R_{4B}$ | $R_{5B}$ | $X_B$ | $Y_B$ | $L_B$ |
|---|---|---|---|---|---|---|---|
| —CH$_2$CONH$_2$ | 2-pyridyl-CH(CH$_3$)– | —CH$_3$ | —CH$_3$ | —CONH$_2$ | =O | —N(CH$_3$)CO— | —CH$_2$— |
| —CH$_2$CH$_2$OH | 2-pyridyl-CH(CH$_3$)– | —CH$_3$ | —CH$_3$ | —OCH$_3$ | =O | —N(CH$_3$)CO— | —CH$_2$CH$_2$— |
| —CH$_2$CONH$_2$ | 2-pyridyl-CH(CH$_3$)– | —CH$_3$ | —CH$_3$ | —CON(CH$_3$)— | =O | —N(CH$_3$)CO— | —CH$_2$— |
| H | 2-(OCF$_3$)phenyl-C(CH$_3$)$_2$– | —CH$_3$ | —CH$_3$ | —OH | =O | —O— | —CH$_2$CH$_2$— |
| H | 2-(OCF$_3$)phenyl-C(CH$_3$)$_2$– | —CH$_3$ | —CH$_3$ | —CONH$_2$ | =O | —O— | —CH$_2$— |
| H | 2-(OCF$_3$)phenyl-C(CH$_3$)$_2$– | —CH$_3$ | —CH$_3$ | —OH | =O | —N(CH)$_3$— | —CH$_2$CH$_2$— |
| H | 2-(OCF$_3$)phenyl-C(CH$_3$)$_2$– | —CH$_3$ | —CH$_3$ | —CONH$_2$ | =O | —N(CH)$_3$— | —CH$_2$— |

TABLE 3-continued
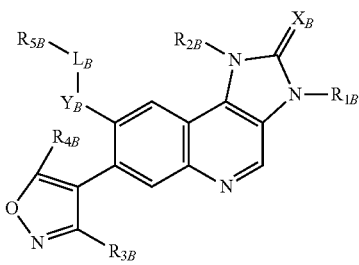
Formula 1B
| $R_{1B}$ | $R_{2B}$ | $R_{3B}$ | $R_{4B}$ | $R_{5B}$ | $X_B$ | $Y_B$ | $L_B$ |
|---|---|---|---|---|---|---|---|
| H | 2-(OCF₃)phenyl | —CH₃ | —CH₃ | —OH | =O | —N(CH₃)CO— | —CH₂CH₂— |
| H | 2-(OCF₃)phenyl | —CH₃ | —CH₃ | —CONH₂ | =O | —N(CH₃)CO— | —CH₂— |
| H | 2-(OCF₃)phenyl | —CH₃ | —CH₃ | —OCH₃ | =O | —N(CH₃)CO— | —CH₂CH₂— |
| H | 2-(OCF₃)phenyl | —CH₃ | —CH₃ | —CON(CH₃)— | =O | —N(CH₃)CO— | —CH₂— |
| —CH₂CH₂OH | 2-(OCF₃)phenyl | —CH₃ | —CH₃ | —OH | =O | —O— | —CH₂CH₂— |

TABLE 4
Formula 1C
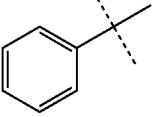
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 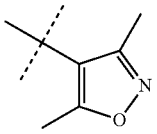 | H | H | H | H | 3, 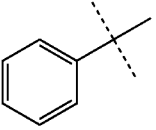 | —CH$_2$— | bond |
| 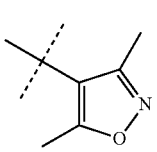 | CH$_3$ | H | H | H | 3, 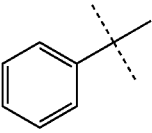 | —CH$_2$— | bond |
| 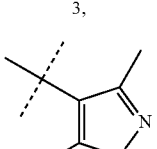 | H | H | H | 2, CH$_3$ | 3, 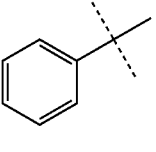 | —CH$_2$— | bond |
| 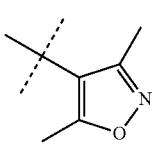 | CH$_3$ | H | H | 2, CH$_3$ | 3, 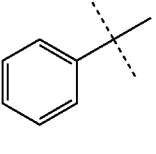 | —CH$_2$— | bond |
| 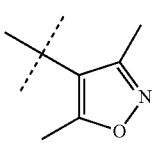 | H | H | H | H | 3, 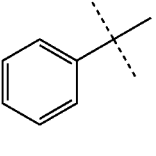 | —CH$_2$— | —CH$_2$— |
| 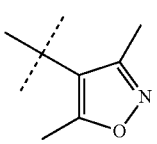 | CH$_3$ | H | H | H | 3, 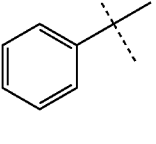 | —CH$_2$— | —CH$_2$— |
| 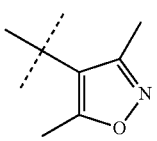 | H | H | H | 2, CH$_3$ | 3, | —CH$_2$— | —CH$_2$— |

TABLE 4-continued

Formula 1C

| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| phenyl | CH₃ | H | H | 2, CH₃ | 3, dimethylisoxazole | —CH₂— | —CH₂— |
| 2-Cl-phenyl | H | H | H | H | 3, dimethylisoxazole | —CH₂— | bond |
| 2-Cl-phenyl | CH₃ | H | H | H | 3, dimethylisoxazole | —CH₂— | bond |
| 2-Cl-phenyl | H | H | H | 2, CH₃ | 3, dimethylisoxazole | —CH₂— | bond |
| 2-Cl-phenyl | CH₃ | H | H | 2, CH₃ | 3, dimethylisoxazole | —CH₂— | bond |
| 2-Cl-phenyl | H | H | H | H | 3, dimethylisoxazole | —CH₂— | —CH₂— |

TABLE 4-continued
Formula 1C
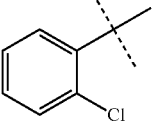
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 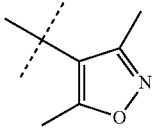 | CH$_3$ | H | H | H | 3, 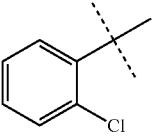 | —CH$_2$— | —CH$_2$— |
| 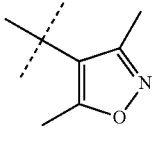 | H | H | H | 2, CH$_3$ | 3, 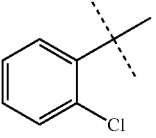 | —CH$_2$— | —CH$_2$— |
| 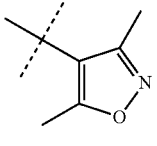 | CH$_3$ | H | H | 2, CH$_3$ | 3, 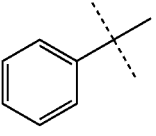 | —CH$_2$— | —CH$_2$— |
| 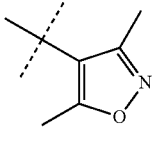 | H | H | H | H | 3, 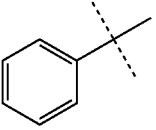 | —CH$_2$— | bond |
| 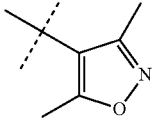 | CH$_3$ | CH$_3$ | H | H | 3, 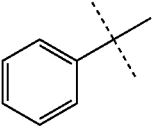 | —CH$_2$— | bond |
| 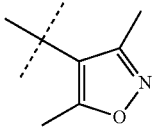 | H | CH$_3$ | H | 2, CH$_3$ | 3,  | —CH$_2$— | bond |

TABLE 4-continued
Formula 1C
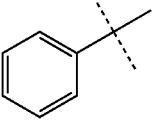
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 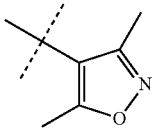 | CH₃ | CH₃ | H | 2, CH₃ | 3, 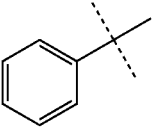 | —CH₂— | bond |
| 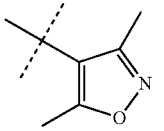 | H | CH₃ | H | H | 3, 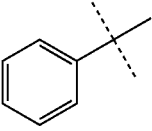 | —CH₂— | —CH₂— |
| 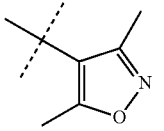 | CH₃ | CH₃ | H | H | 3, 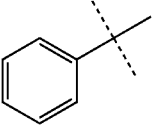 | —CH₂— | —CH₂— |
| 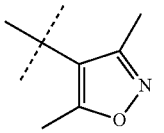 | H | CH₃ | H | 2, CH₃ | 3, 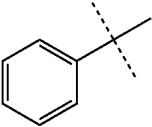 | —CH₂— | —CH₂— |
| 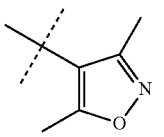 | CH₃ | CH₃ | H | 2, CH₃ | 3, 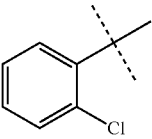 | —CH₂— | —CH₂— |
| 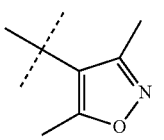 | H | CH₃ | H | H | 3,  | —CH₂— | bond |

TABLE 4-continued
Formula 1C
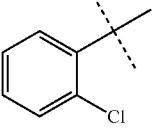
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 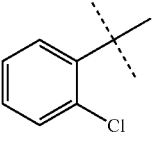 | CH₃ | CH₃ | H | H | 3, 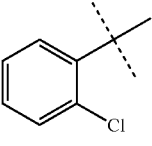 | —CH₂— | bond |
| 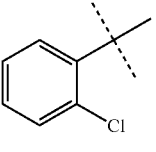 | H | CH₃ | H | 2, CH₃ | 3, 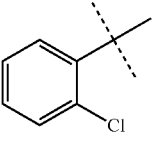 | —CH₂— | bond |
| 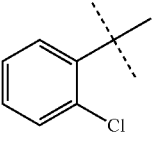 | CH₃ | CH₃ | H | 2, CH₃ | 3, | —CH₂— | bond |
| | H | CH₃ | H | H | 3, | —CH₂— | —CH₂— |
| | CH₃ | CH₃ | H | H | 3, | —CH₂— | —CH₂— |
| | H | CH₃ | H | 2, CH₃ | 3, | —CH₂— | —CH₂— |

TABLE 4-continued
Formula 1C
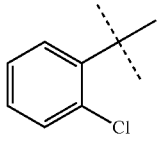
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 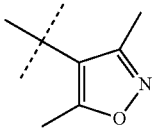 | CH₃ | CH₃ | H | 2, CH₃ | 3, 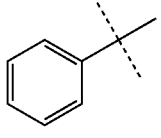 | —CH₂— | —CH₂— |
| 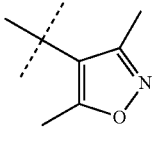 | H | H | H | 2, 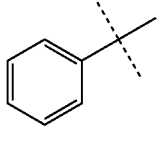 | 3, 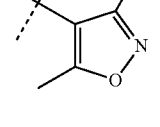 | —CH₂— | bond |
| 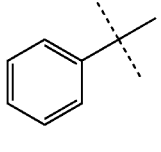 | CH₃ | H | H | 2, 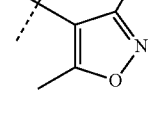 | 3, 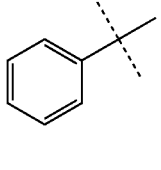 | —CH₂— | bond |
| 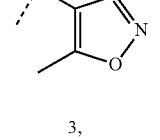 | H | H | H | 2, Ph | 3, 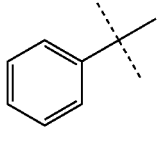 | —CH₂— | bond |
| 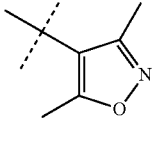 | CH₃ | H | H | 2, Ph | 3, | —CH₂— | bond |
| | H | H | H | 2, | 3, | —CH₂— | —CH₂— |

US 10,266,536 B2
TABLE 4-continued
Formula 1C
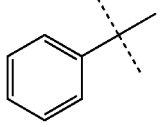
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 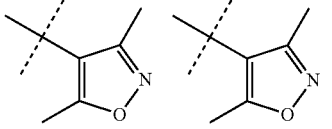 | CH₃ | H | H | 2, 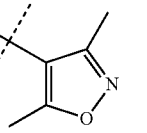 | 3, 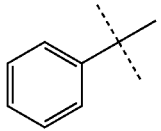 | —CH₂— | —CH₂— |
| 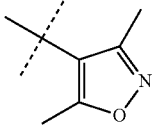 | H | H | H | 2, Ph | 3, 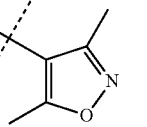 | —CH₂— | —CH₂— |
| 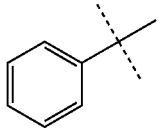 | CH₃ | H | H | 2, Ph | 3, 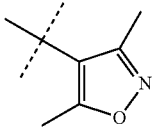 | —CH₂— | —CH₂— |
| 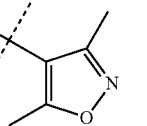 | H | H | H | 2, 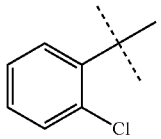 | 3, 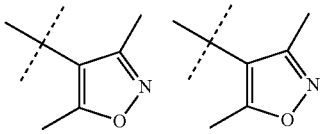 | —CH₂— | bond |
| 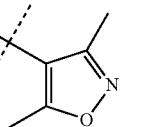 | CH₃ | H | H | 2, 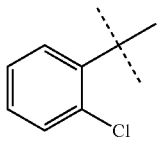 | 3, 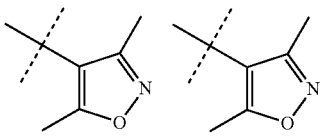 | —CH₂— | bond |
| 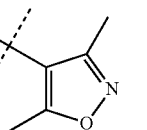 | H | H | H | 2, Ph | 3, 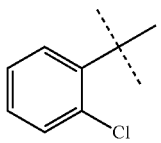 | —CH₂— | bond |

TABLE 4-continued
Formula 1C
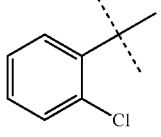
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 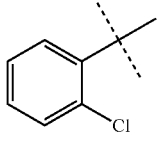 | CH$_3$ | H | H | 2, Ph | 3, 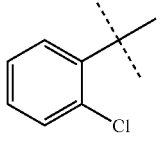 | —CH$_2$— | bond |
| 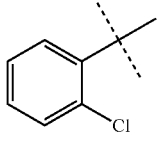 | H | H | H | 2, 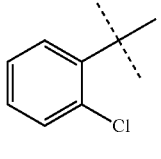 | 3, 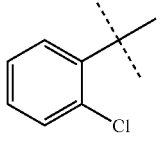 | —CH$_2$— | —CH$_2$— |
| 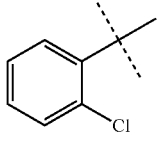 | CH$_3$ | H | H | 2, 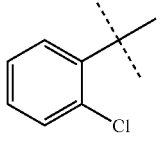 | 3, 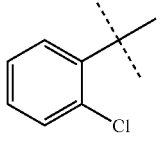 | —CH$_2$— | —CH$_2$— |
| 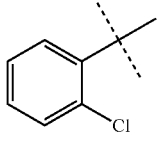 | H | H | H | 2, Ph | 3, 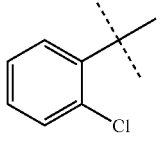 | —CH$_2$— | —CH$_2$— |
| 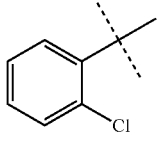 | CH$_3$ | H | H | 2, Ph | 3, 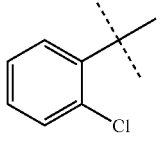 | —CH$_2$— | —CH$_2$— |
| 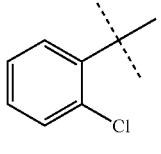 | H | H | H | 2, 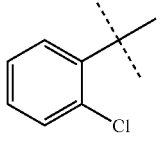 | 3, 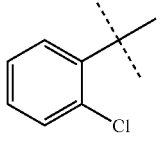 | —CH$_2$— | bond |

TABLE 4-continued
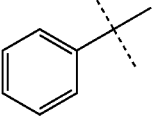
Formula 1C
| R$_{1C}$ | R$_{2C}$ | R$_{3C}$ | R$_{4C}$ | Position, R$_{5C}$ | Position, R$_{6C}$ | L$_{1C}$ | L$_{2C}$ |
|---|---|---|---|---|---|---|---|
| 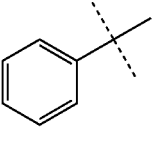 | CH$_3$ | CH$_3$ | H | 2, 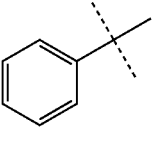 | 3, 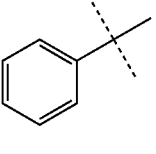 | —CH$_2$— | bond |
| 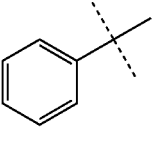 | H | CH$_3$ | H | 2, Ph | 3, 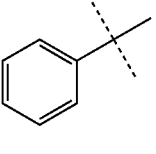 | —CH$_2$— | bond |
| 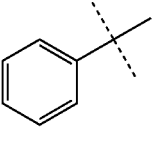 | CH$_3$ | CH$_3$ | H | 2, Ph | 3, 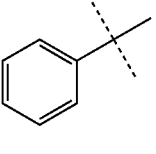 | —CH$_2$— | bond |
| 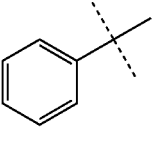 | H | CH$_3$ | H | 2, 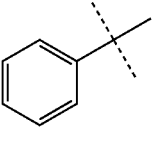 | 3, 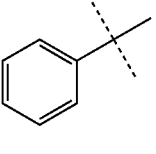 | —CH$_2$— | —CH$_2$— |
| 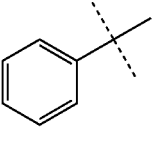 | CH$_3$ | CH$_3$ | H | 2, 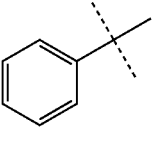 | 3, 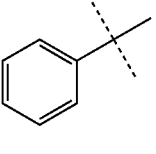 | —CH$_2$— | —CH$_2$— |
| 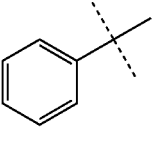 | H | CH$_3$ | H | 2, Ph | 3, 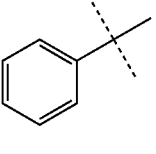 | —CH$_2$— | —CH$_2$— |

TABLE 4-continued
Formula 1C
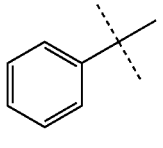
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 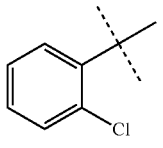 | CH₃ | CH₃ | H | 2, Ph | 3, 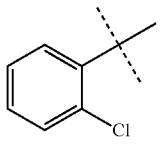 | —CH₂— | —CH₂— |
| 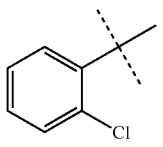 | H | CH₃ | H | 2, 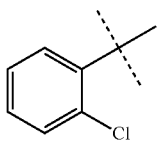 | 3, 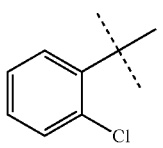 | —CH₂— | bond |
| (2-Cl-phenyl) | CH₃ | CH₃ | H | 2, (3,5-dimethylisoxazol-4-yl) | 3, (3,5-dimethylisoxazol-4-yl) | —CH₂— | bond |
| (2-Cl-phenyl) | H | CH₃ | H | 2, Ph | 3, (3,5-dimethylisoxazol-4-yl) | —CH₂— | bond |
| (2-Cl-phenyl) | CH₃ | CH₃ | H | 2, Ph | 3, (3,5-dimethylisoxazol-4-yl) | —CH₂— | bond |
| (2-Cl-phenyl) | H | CH₃ | H | 2, (3,5-dimethylisoxazol-4-yl) | 3, (3,5-dimethylisoxazol-4-yl) | —CH₂— | —CH₂— |

TABLE 4-continued
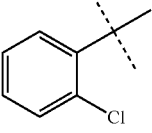
Formula 1C
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 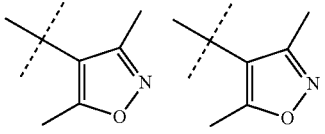 | CH$_3$ | CH$_3$ | H | 2, 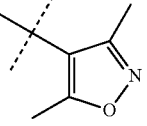 | 3, 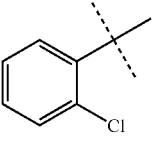 | —CH$_2$— | —CH$_2$— |
| 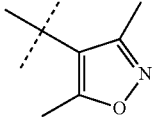 | H | CH$_3$ | H | 2, Ph | 3, 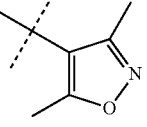 | —CH$_2$— | —CH$_2$— |
| 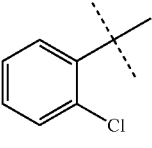 | CH$_3$ | CH$_3$ | H | 2, Ph | 3, 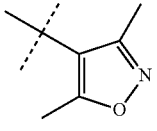 | —CH$_2$— | —CH$_2$— |
| 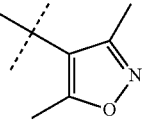 | H | H | Ph | H | 3, 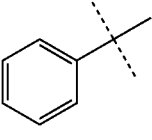 | —CH$_2$— | —CH$_2$— |
| 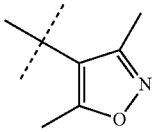 | CH$_3$ | H | Ph | H | 3, 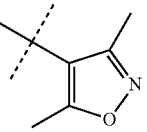 | —CH$_2$— | —CH$_2$— |
| 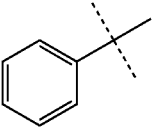 | H | H | Ph | 2, CH$_3$ | 3, 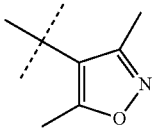 | —CH$_2$— | —CH$_2$— |

TABLE 4-continued
Formula 1C
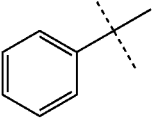
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 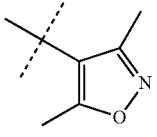 | CH₃ | H | Ph | 2, CH₃ | 3, 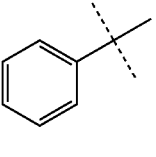 | —CH₂— | —CH₂— |
| 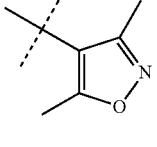 | H | H | Ph | H | 3, 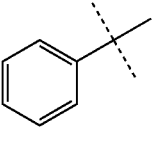 | —CH₂— | —CH₂— |
| 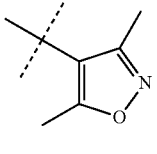 | CH₃ | H | Ph | H | 3, 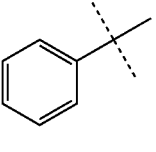 | —CH₂— | —CH₂— |
| 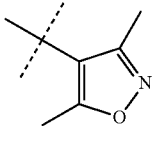 | H | H | Ph | 2, CH₃ | 3, 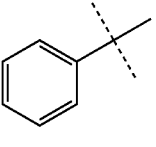 | —CH₂— | —CH₂— |
| 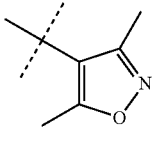 | CH₃ | H | Ph | 2, CH₃ | 3, 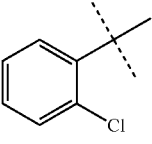 | —CH₂— | —CH₂— |
| 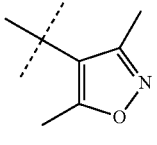 | H | H | Ph | H | 3,  | —CH₂— | —CH₂— |

TABLE 4-continued
Formula 1C
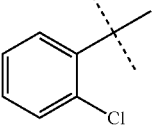
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 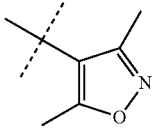 | CH₃ | H | Ph | H | 3, 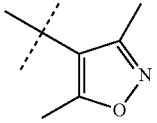 | —CH₂— | —CH₂— |
| 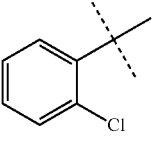 | H | H | Ph | 2, CH₃ | 3, 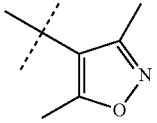 | —CH₂— | —CH₂— |
| 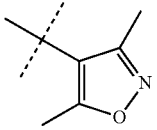 | CH₃ | H | Ph | 2, CH₃ | 3, 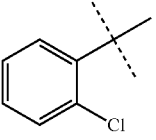 | —CH₂— | —CH₂— |
| 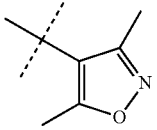 | H | H | Ph | H | 3, 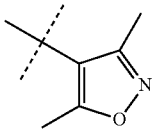 | —CH₂— | —CH₂— |
| 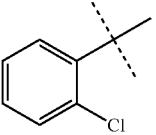 | CH₃ | H | Ph | H | 3, 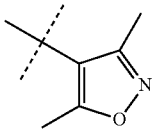 | —CH₂— | —CH₂— |
| 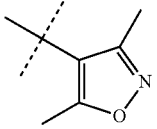 | H | H | Ph | 2, CH₃ | 3, 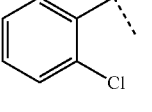 | —CH₂— | —CH₂— |

TABLE 4-continued
Formula 1C
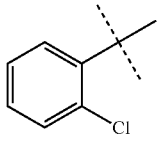
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 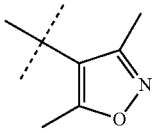 | CH$_3$ | H | Ph | 2, CH$_3$ | 3, 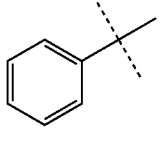 | —CH$_2$— | —CH$_2$— |
| 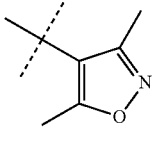 | H | H | Ph | H | 3, 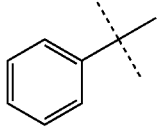 | —CH$_2$— | —CH$_2$— |
| 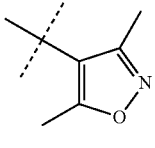 | CH$_3$ | CH$_3$ | Ph | H | 3, 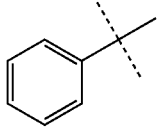 | —CH$_2$— | —CH$_2$— |
| 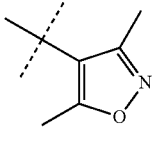 | H | CH$_3$ | Ph | 2, CH$_3$ | 3, 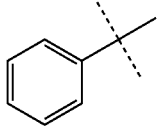 | —CH$_2$— | —CH$_2$— |
| 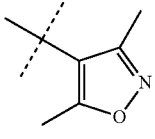 | CH$_3$ | CH$_3$ | Ph | 2, CH$_3$ | 3, 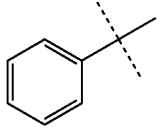 | —CH$_2$— | —CH$_2$— |
| 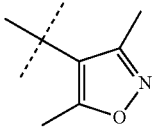 | H | CH$_3$ | Ph | H | 3, | —CH$_2$— | —CH$_2$— |

TABLE 4-continued
Formula 1C
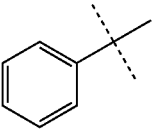
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 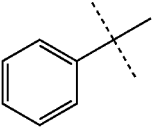 | CH₃ | CH₃ | Ph | H | 3, 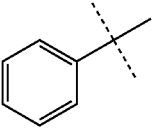 | —CH₂— | —CH₂— |
| 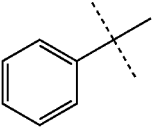 | H | CH₃ | Ph | 2, CH₃ | 3, 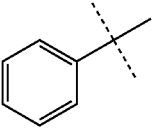 | —CH₂— | —CH₂— |
| 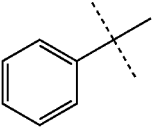 | CH₃ | CH₃ | Ph | 2, CH₃ | 3, 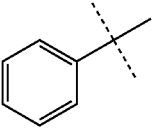 | —CH₂— | —CH₂— |
| 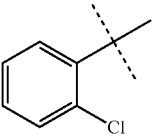 | H | CH₃ | Ph | H | 3, 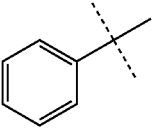 | —CH₂— | —CH₂— |
| 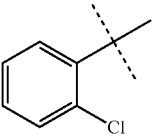 | CH₃ | CH₃ | Ph | H | 3, 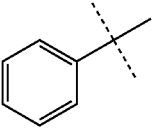 | —CH₂— | —CH₂— |
| 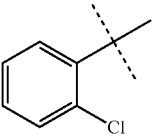 | H | CH₃ | Ph | 2, CH₃ | 3, 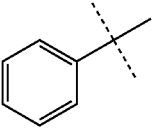 | —CH₂— | —CH₂— |

TABLE 4-continued

Formula 1C

| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 2-Cl-phenyl | CH₃ | CH₃ | Ph | 2, CH₃ | 3, 3,5-dimethylisoxazol-4-yl | —CH₂— | —CH₂— |
| 2-Cl-phenyl | H | CH₃ | Ph | H | 3, 3,5-dimethylisoxazol-4-yl | —CH₂— | —CH₂— |
| 2-Cl-phenyl | CH₃ | CH₃ | Ph | H | 3, 3,5-dimethylisoxazol-4-yl | —CH₂— | —CH₂— |
| 2-Cl-phenyl | H | CH₃ | Ph | 2, CH₃ | 3, 3,5-dimethylisoxazol-4-yl | —CH₂— | —CH₂— |
| 2-Cl-phenyl | CH₃ | CH₃ | Ph | 2, CH₃ | 3, 3,5-dimethylisoxazol-4-yl | —CH₂— | —CH₂— |
| pyridin-2-yl | H | H | Ph | 2, CH₃ | 3, 3,5-dimethylisoxazol-4-yl | —CH₂— | —CH₂— |
| pyridin-2-yl | CH₃ | H | Ph | 2, CH₃ | 3, 3,5-dimethylisoxazol-4-yl | —CH₂— | —CH₂— |

TABLE 4-continued
Formula 1C
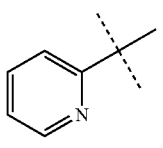
| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 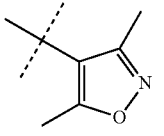 | H | H | H | H | 3, 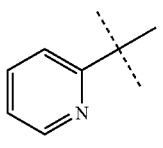 | —CH$_2$— | —CH$_2$— |
| 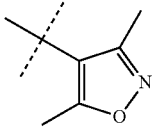 | CH$_3$ | H | H | H | 3, 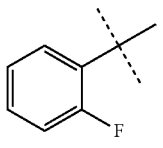 | —CH$_2$— | —CH$_2$— |
| 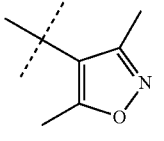 | H | H | H | H | 3, 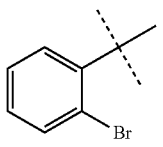 | —CH$_2$— | bond |
| 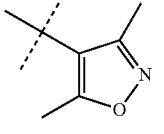 | H | H | H | H | 3, 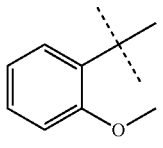 | —CH$_2$— | bond |
| 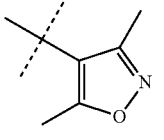 | H | H | H | H | 3, 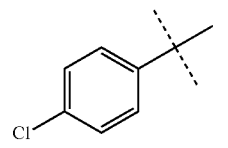 | —CH$_2$— | bond |
| 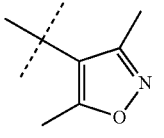 | H | H | H | H | 3, | —CH$_2$— | bond |

TABLE 5
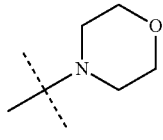
Formula 1C
| $R_{1C}$—$L_{1C}$—N—$R_{2C}$ | $R_{3C}$ | —$L_{2C}$—$R_{4C}$ | Position, $R_{5C}$ | Position, $R_{6C}$ |
|---|---|---|---|---|
| 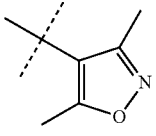 | H | H | H | 3, 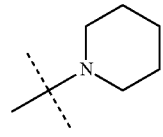 |
| 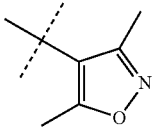 | H | H | H | 3, 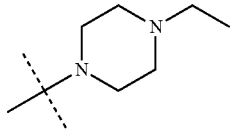 |
| 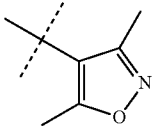 | H | H | H | 3, 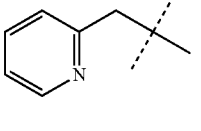 |
TABLE 6
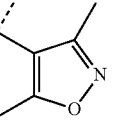
Formula 1D
| $R_{1D}$ | $R_{2D}$ | $R_{3D}$ | $R_{4D}$ | $R_{5D}$ | $R_{6D}$ | $X_D$ |
|---|---|---|---|---|---|---|
| 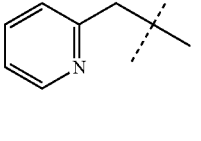 | —COCH$_3$ | —CH$_2$CH$_2$OH | 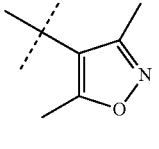 | H | H | —O— |
| 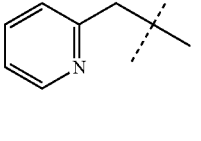 | —COCH$_3$ | —CH$_2$CH$_2$OCH$_3$ | 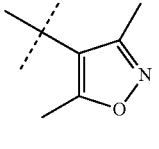 | H | H | —O— |

TABLE 6-continued

Formula 1D

| R{1D} | R{2D} | R{3D} | R{4D} | R{5D} | R{6D} | X{D} |
|---|---|---|---|---|---|---|
| 2-pyridylmethyl | —COCH₃ | —CH₂CONH₂ | 3,5-dimethylisoxazol-4-yl | H | H | —O— |
| 2-pyridylmethyl | —COCH₃ | —CH₂CONH | 3,5-dimethylisoxazol-4-yl | H | H | —O— |
| 4-pyridylmethyl | —COCH₃ | —CH₂CH₂OH | 3,5-dimethylisoxazol-4-yl | H | H | —O— |
| 4-pyridylmethyl | —COCH₃ | —CH₂CH₂OCH₃ | 3,5-dimethylisoxazol-4-yl | H | H | —O— |
| 4-pyridylmethyl | —COCH₃ | —CH₂CONH₂ | 3,5-dimethylisoxazol-4-yl | H | H | —O— |
| 4-pyridylmethyl | —COCH₃ | —CH₂CONH₂ | 3,5-dimethylisoxazol-4-yl | H | H | —O— |
| 2-pyridylmethyl | —COCH₃ | —CH₂CH₂OH | 3,5-diethylisoxazol-4-yl | H | H | —O— |
| 2-pyridylmethyl | —COCH₃ | —CH₂CH₂OCH₃ | 3,5-diethylisoxazol-4-yl | H | H | —O— |

TABLE 6-continued
Formula 1D
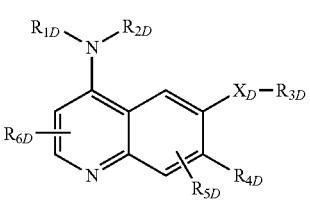
| R$_{1D}$ | R$_{2D}$ | R$_{3D}$ | R$_{4D}$ | R$_{5D}$ | R$_{6D}$ | X$_D$ |
|---|---|---|---|---|---|---|
| 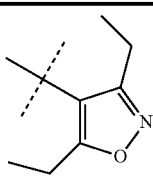 | —COCH$_3$ | —CH$_2$CONH$_2$ |  | H | H | —O— |
| 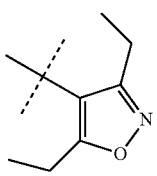 | —COCH$_3$ | —CH$_2$CONH$_2$ |  | H | H | —O— |
| 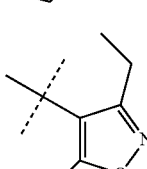 | —COCH$_3$ | —CH$_2$CH$_2$OH |  | H | H | —O— |
| 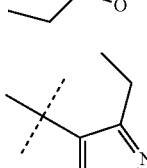 | —COCH$_3$ | —CH$_2$CH$_2$OCH$_3$ |  | H | H | —O— |
| 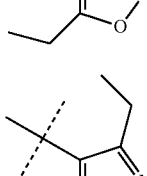 | —COCH$_3$ | —CH$_2$CONH$_2$ |  | H | H | —O— |
| 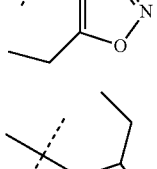 | —COCH$_3$ | —CH$_2$CONH$_2$ |  | H | H | —O— |
| 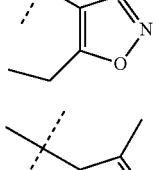 | —COCH$_3$ | —CH$_2$CH$_2$OH | 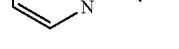 | H | H | —CH$_2$— |
| 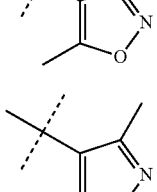 | —COCH$_3$ | —CH$_2$CH$_2$OCH$_3$ | (same isoxazole) | H | H | —CH$_2$— |

TABLE 6-continued

Formula 1D

| R₁D | R₂D | R₃D | R₄D | R₅D | R₆D | X_D |
|---|---|---|---|---|---|---|
| 2-pyridylmethyl | —COCH₃ | —CH₂CONH₂ | 3,5-dimethylisoxazol-4-yl | H | H | —CH₂— |
| 2-pyridylmethyl | —COCH₃ | —CH₂CONH₂ | 3,5-dimethylisoxazol-4-yl | H | H | —CH₂— |
| 4-pyridylmethyl | —COCH₃ | —CH₂CH₂OH | 3,5-dimethylisoxazol-4-yl | H | H | —NH— |
| 4-pyridylmethyl | —COCH₃ | —CH₂CH₂OCH₃ | 3,5-dimethylisoxazol-4-yl | H | H | —NH— |
| 4-pyridylmethyl | —COCH₃ | —CH₂CONH₂ | 3,5-dimethylisoxazol-4-yl | H | H | —NH— |
| 4-pyridylmethyl | —COCH₃ | —CH₂CONH₂ | 3,5-dimethylisoxazol-4-yl | H | H | —NH— |
| 2-pyridylmethyl | —COCH₃ | —CH₂CH₂OH | 3,5-diethylisoxazol-4-yl | H | H | —NH— |
| 2-pyridylmethyl | —COCH₃ | —CH₂CH₂OCH₃ | 3,5-diethylisoxazol-4-yl | H | H | —O— |

TABLE 6-continued

Formula 1D

| R$_{1D}$ | R$_{2D}$ | R$_{3D}$ | R$_{4D}$ | R$_{5D}$ | R$_{6D}$ | X$_D$ |
|---|---|---|---|---|---|---|
| 2-pyridylmethyl | —COCH$_3$ | —CH$_2$CONH$_2$ | 3,5-diethylisoxazol-4-yl | H | H | —O— |
| 2-pyridylmethyl | —COCH$_3$ | —CH$_2$CONH$_2$ | 3,5-diethylisoxazol-4-yl | H | H | —O— |
| 4-pyridylmethyl | —COCH$_3$ | —CH$_2$CH$_2$OH | 3,5-diethylisoxazol-4-yl | H | H | —O— |
| 4-pyridylmethyl | —COCH$_3$ | —CH$_2$CH$_2$OCH$_3$ | 3,5-diethylisoxazol-4-yl | H | H | —O— |
| 4-pyridylmethyl | —COCH$_3$ | —CH$_2$CONH$_2$ | 3,5-diethylisoxazol-4-yl | H | H | —O— |
| 4-pyridylmethyl | —COCH$_3$ | —CH$_2$CONH$_2$ | 3,5-diethylisoxazol-4-yl | H | H | —O— |
| 1-(2-pyridyl)ethyl | —COCH$_3$ | —CH$_2$CH$_2$OH | 3,5-dimethylisoxazol-4-yl | H | H | —O— |
| 1-(2-pyridyl)ethyl | —COCH$_3$ | —CH$_2$CH$_2$OCH$_3$ | 3,5-dimethylisoxazol-4-yl | H | H | —O— |

TABLE 6-continued
Formula 1D
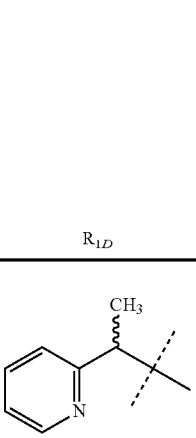
| R$_{1D}$ | R$_{2D}$ | R$_{3D}$ | R$_{4D}$ | R$_{5D}$ | R$_{6D}$ | X$_D$ |
|---|---|---|---|---|---|---|
| 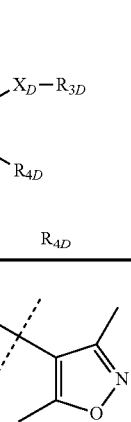 | —COCH$_3$ | —CH$_2$CONH$_2$ | 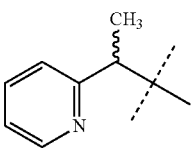 | H | H | —O— |
| 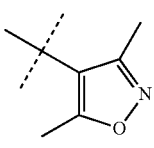 | —COCH$_3$ | —CH$_2$CONH$_2$ | 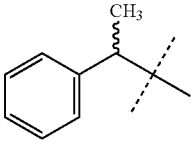 | H | H | —O— |
| 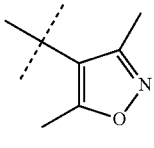 | —COCH$_3$ | —CH$_2$CH$_2$OH | 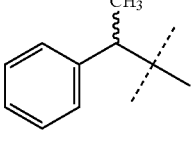 | H | H | —O— |
| 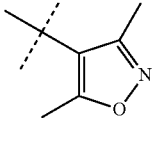 | —COCH$_3$ | —CH$_2$CH$_2$OCH$_3$ | 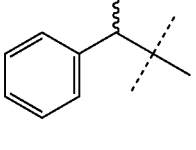 | H | H | —O— |
| 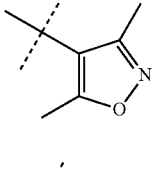 | —COCH$_3$ | —CH$_2$CONH$_2$ | 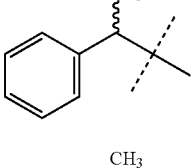 | H | H | —O— |
| 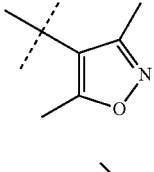 | —COCH$_3$ | —CH$_2$CONH$_2$ | 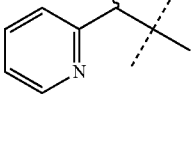 | H | H | —O— |
| 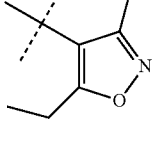 | —COCH$_3$ | —CH$_2$CH$_2$OH | 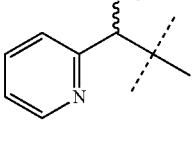 | H | H | —O— |
| 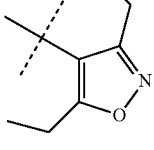 | —COCH$_3$ | —CH$_2$CH$_2$OCH$_3$ | | H | H | —O— |

TABLE 6-continued
Formula 1D
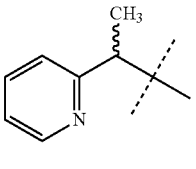
| R$_{1D}$ | R$_{2D}$ | R$_{3D}$ | R$_{4D}$ | R$_{5D}$ | R$_{6D}$ | X$_D$ |
|---|---|---|---|---|---|---|
| 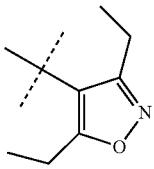 | —COCH$_3$ | —CH$_2$CONH$_2$ | 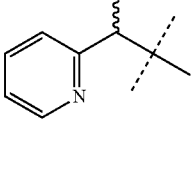 | H | H | —O— |
| 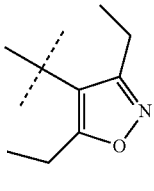 | —COCH$_3$ | —CH$_2$CONH$_2$ | 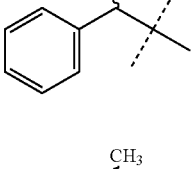 | H | H | —O— |
| 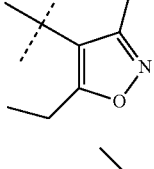 | —COCH$_3$ | —CH$_2$CH$_2$OH | 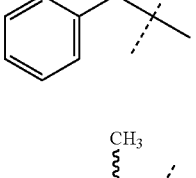 | H | H | —O— |
| 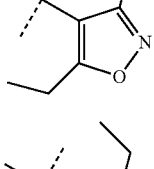 | —COCH$_3$ | —CH$_2$CH$_2$OCH$_3$ | 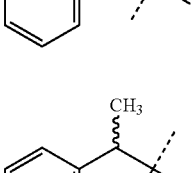 | H | H | —O— |
| 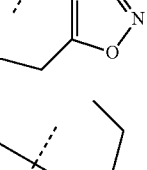 | —COCH$_3$ | —CH$_2$CONH$_2$ | 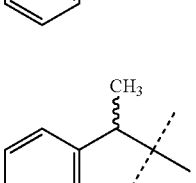 | H | H | —O— |
| 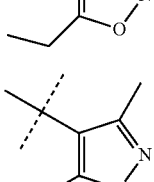 | —COCH$_3$ | —CH$_2$CONH$_2$ | 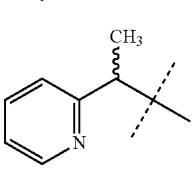 | H | H | —O— |
| 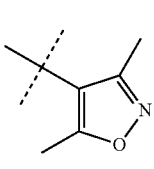 | —COCH$_3$ | —CH$_2$CH$_2$OH | 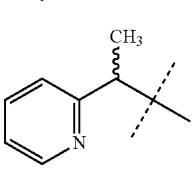 | H | H | —CH$_2$— |
| 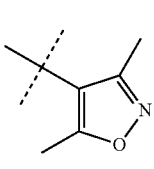 | —COCH$_3$ | —CH$_2$CH$_2$OCH$_3$ | | H | H | —CH$_2$— |

TABLE 6-continued

Formula 1D

| R$_{1D}$ | R$_{2D}$ | R$_{3D}$ | R$_{4D}$ | R$_{5D}$ | R$_{6D}$ | X$_D$ |
|---|---|---|---|---|---|---|
| CH₃, pyridin-2-yl ethyl | —COCH₃ | —CH₂CONH₂ | 3,5-dimethylisoxazol-4-yl | H | H | —CH₂— |
| CH₃, pyridin-2-yl ethyl | —COCH₃ | —CH₂CONH₂ | 3,5-dimethylisoxazol-4-yl | H | H | —CH₂— |
| CH₃, phenyl ethyl | —COCH₃ | —CH₂CH₂OH | 3,5-dimethylisoxazol-4-yl | H | H | —NH— |
| CH₃, phenyl ethyl | —COCH₃ | —CH₂CH₂OCH₃ | 3,5-dimethylisoxazol-4-yl | H | H | —NH— |
| CH₃, phenyl ethyl | —COCH₃ | —CH₂CONH₂ | 3,5-dimethylisoxazol-4-yl | H | H | —NH— |
| CH₃, phenyl ethyl | —COCH₃ | —CH₂CONH₂ | 3,5-dimethylisoxazol-4-yl | H | H | —NH— |
| CH₃, pyridin-2-yl ethyl | —COCH₃ | —CH₂CH₂OH | 3,5-diethylisoxazol-4-yl | H | H | —NH— |
| CH₃, pyridin-2-yl ethyl | —COCH₃ | —CH₂CH₂OCH₃ | 3,5-diethylisoxazol-4-yl | H | H | —O— |

TABLE 6-continued

Formula 1D

| R1D | R2D | R3D | R4D | R5D | R6D | XD |
|---|---|---|---|---|---|---|
| CH3, 2-pyridyl (racemic) | —COCH3 | —CH2CONH2 | 3,5-diethylisoxazol-4-yl | H | H | —O— |
| CH3, 2-pyridyl | —COCH3 | —CH2CONH2 | 3,5-diethylisoxazol-4-yl | H | H | —O— |
| CH3, phenyl | —COCH3 | —CH2CH2OH | 3,5-diethylisoxazol-4-yl | H | H | —O— |
| CH3, phenyl | —COCH3 | —CH2CH2OCH3 | 3,5-diethylisoxazol-4-yl | H | H | —O— |
| CH3, phenyl | —COCH3 | —CH2CONH2 | 3,5-diethylisoxazol-4-yl | H | H | —O— |
| CH3, phenyl | —COCH3 | —CH2CONH2 | 3,5-diethylisoxazol-4-yl | H | H | —O— |

Example 1 (Compounds 21-41 of Table 1)

Compounds 21-41 set forth in Table 1 may be prepared according the synthetic scheme set forth below. Those skilled in the art of organic synthesis will recognize that other substituents may be introduced to the three position (e.g., (—NH—R—R)) and four position according to the scheme.

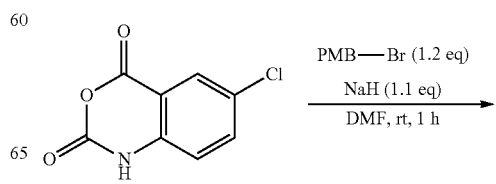

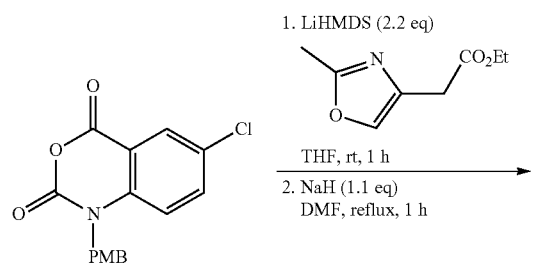
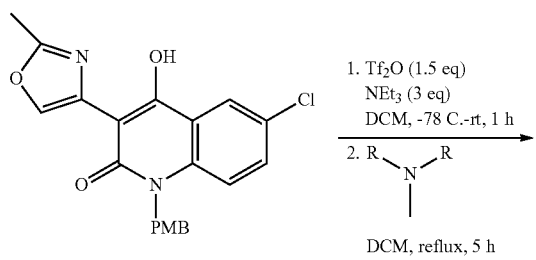
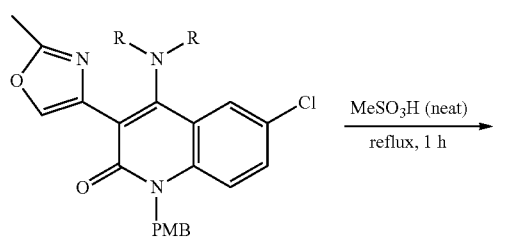
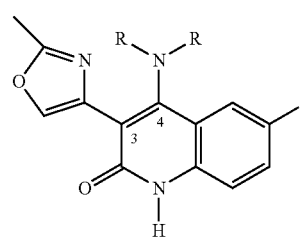
Example 2: Synthetic Scheme—Formula 1A
Compounds of Formula 1A may be prepared according to the synthetic scheme set forth below.
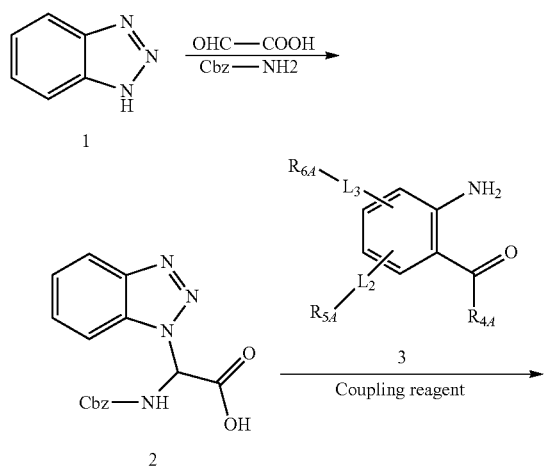
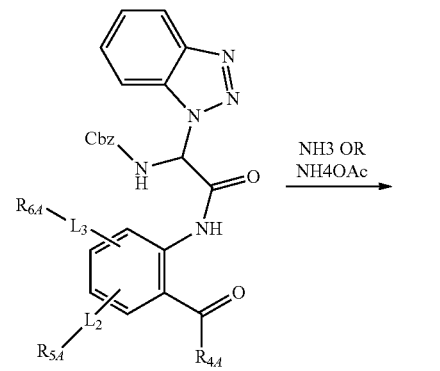
4
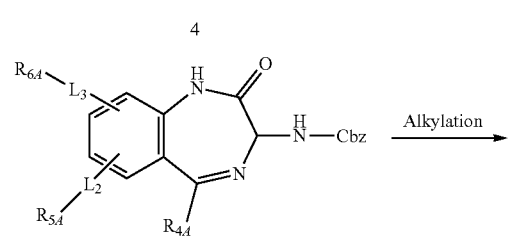
5
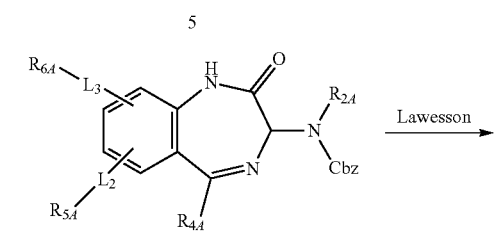
6
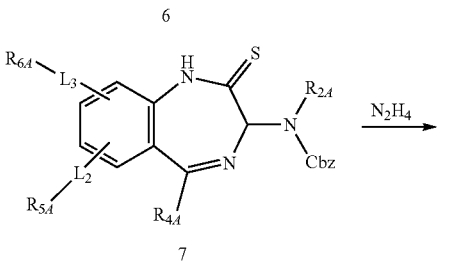
7
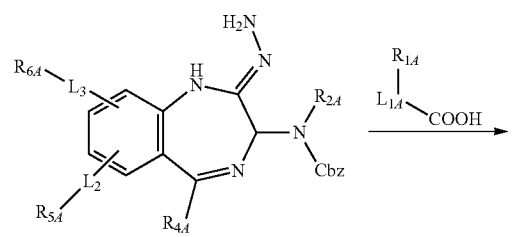
8
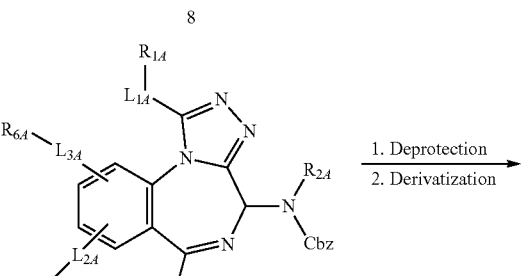
9

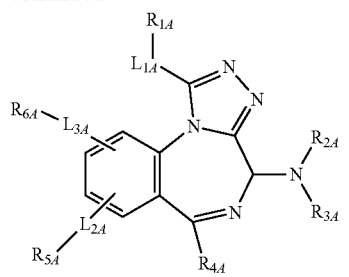

Formula 1A

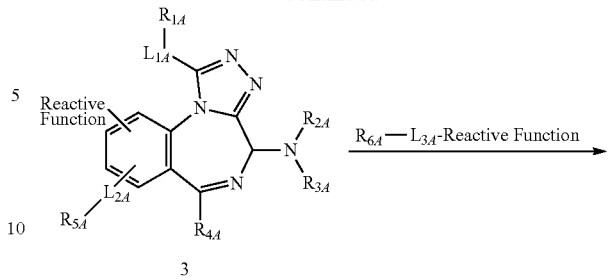

Benzotriazole 1 can be reacted with 2-oxoacetic acid and Cbz-NH2 to get compound 2 which can be coupled with an aniline derivative 3 in presence of a coupling reagent to obtain compound 4. Compound 5 can be obtained by treatment of compound 4 with ammonia or ammonia equivalent. An alkylation of compound 5 will provide compound 6 and subsequent treatment of compound 6 with Lawesson reagent can provide compound 7. Reaction of compound 7 with hydrazine can provide the hydrazine derivative 8 which can be treated with desired carboxylic acid to get the compound 9. Deprotection of the Cbz group followed by appropriate derivatization will provide the targeted compound of the Formula 1A.

Example 3—Synthetic Scheme

The targeted compound of Formula 1A can be prepared by reacting compounds 1, 3, 5, 7 with appropriate side chains having a reacting group as shown below.

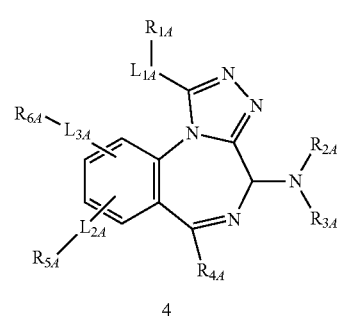

1

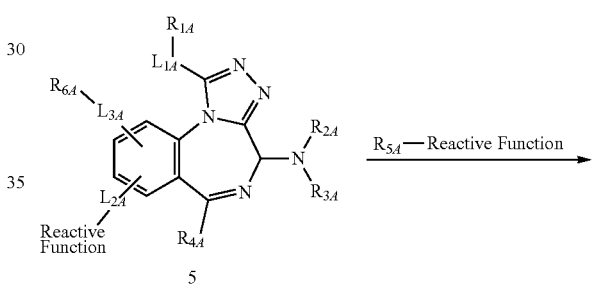

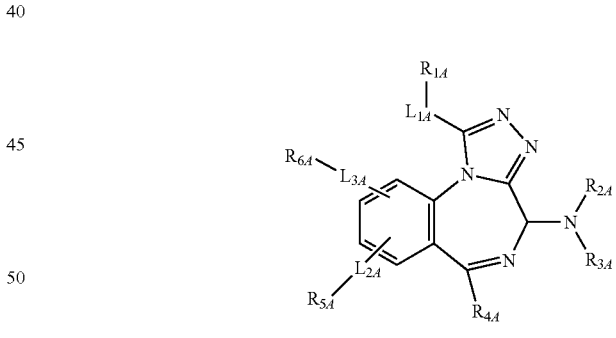

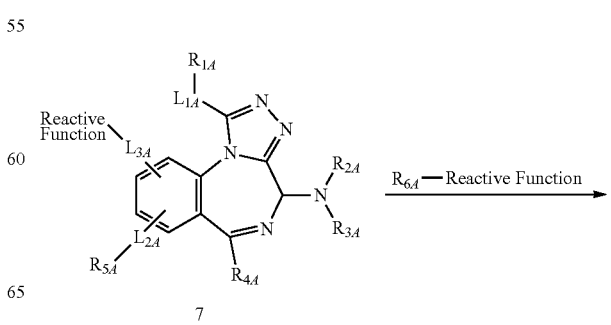

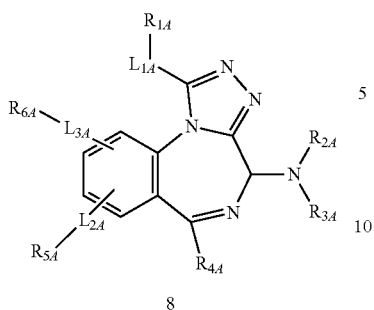

8

Example 4—Synthetic Scheme

The compound 1 can be prepared according to the scheme of Example 2. The treatment of compound 1 with 1,1,1-triethoxyethane will give compound 2 which can be further reacted with carbon monoxide using the palladium catalyst to obtain a carboxylic acid ester derivative 3. The coupling of compound 4 with 2-aminoethanol will provide desired compound 5 of Formula 1A.

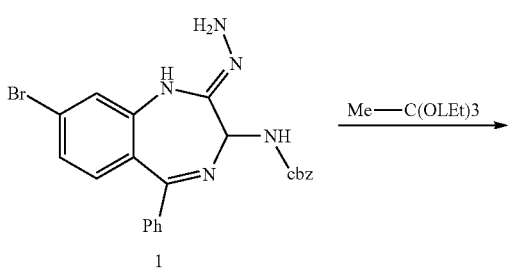

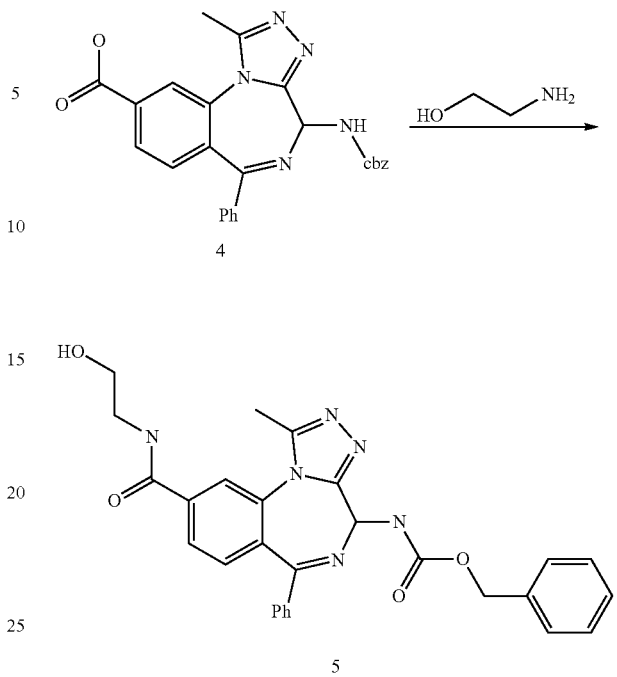

Example 5—Synthetic Scheme

Benzotriazole 1 can be reacted with 2-oxoacetic acid and Cbz-NH2 to get compound 2 which can be coupled with an aniline derivative 3 in presence of a coupling reagent 1-Ethyl-3-(3-dimethylaminopropyl)carbodiimide to obtain compound 4. Compound 5 can be obtained by treatment of compound 4 with ammonia in methanol or ammonia acetate. Treatment of compound 4 with Lawesson reagent can provide compound 5 and subsequent reaction of compound 7 with hydrazine can provide the hydrazine derivative 6 which can be treated with 2-(3,5-dimethylisoxazol-4-yl)acetic acid to get the compound 7. The cyclization of compound 7 in presence of mixture of acetic acid and acetic anhydride will provide compound 8 of Formula 1A.

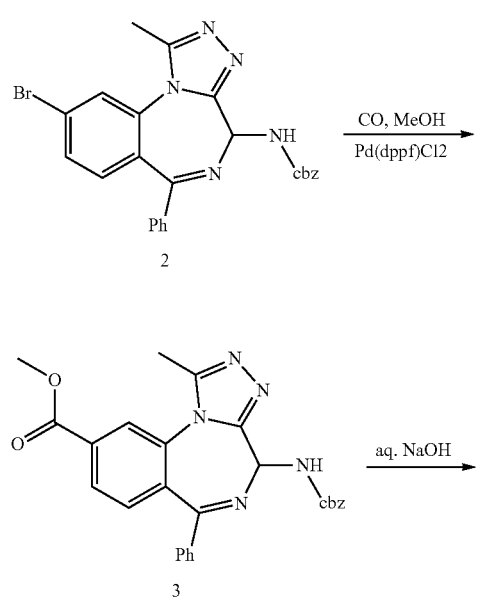

127

-continued

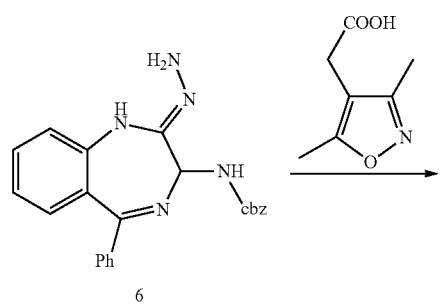

128

-continued

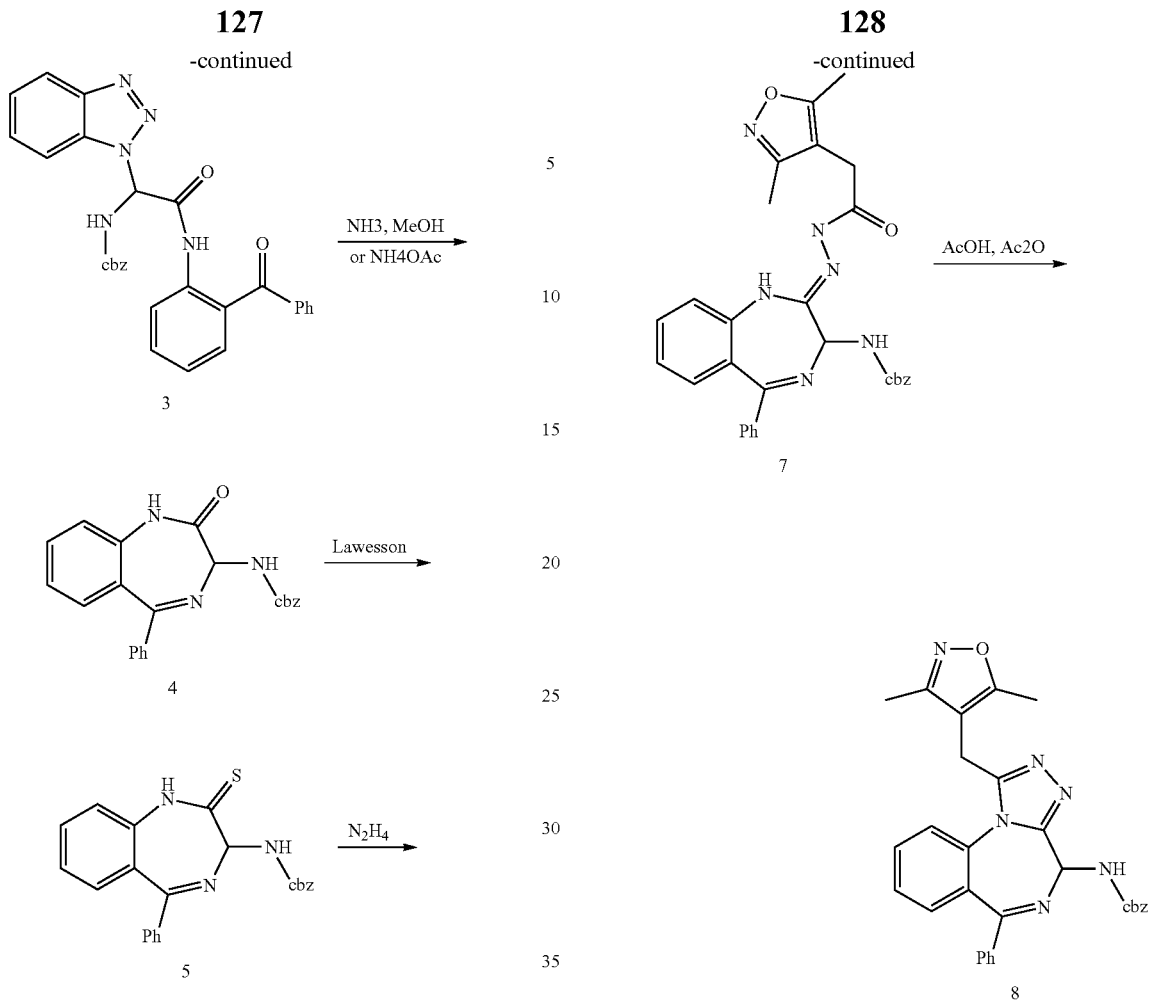

Example 6—Synthetic Scheme

The deprotection of the silyl protecting group using TBAF will provide the free phenolic derivative which then can be treated with 2-chloroacetamide in presence of triethylamine to provide compound 3 of the Formula 1A.

Additionally compound 2 also can be reacted with the (2-bromoethoxy)(tert-butyl)dimethylsilane in presence of triethylamine to get compound 5. The deprotection of the silyl protecting group will provide the desired compound 6 of Formula 1A.

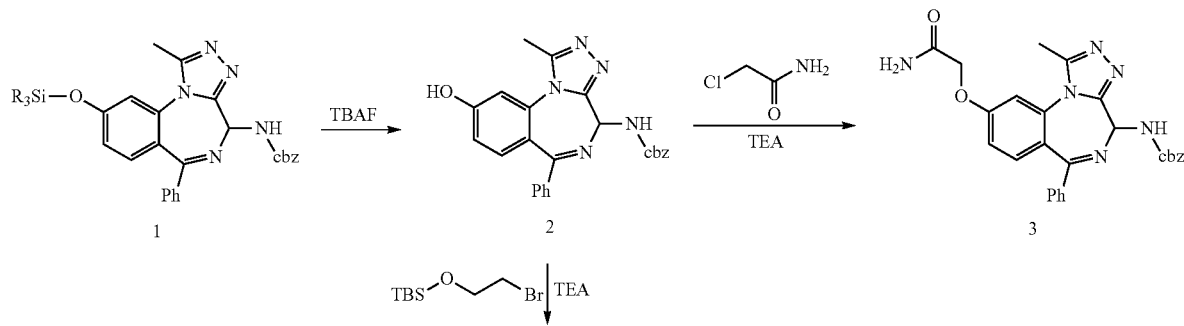

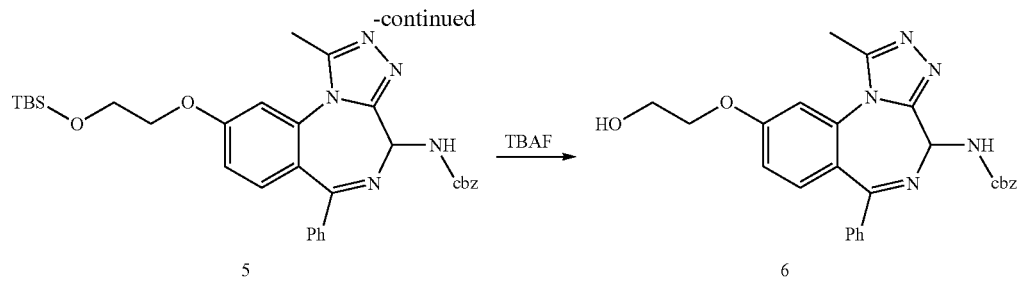

Example 7—Synthetic Scheme—Formula 1B

Compounds of Formula 1B may be prepared according to the synthetic scheme set forth below.

The substituted isoxazole boronic acid can be reacted with 3-iodo or 3-bromo aniline derivatives 2 using Suzuki coupling conditions to give the corresponding amino compounds. Compound 2 may be reacted with diethyl ethoxymethylenemalonate at appropriate temperature with heating conditions to get compound 4. Hydrolysis of compound 4 will provide compound 5 and subsequent decaboxylation will yield compound 6. The nitration of compound 6 will provide corresponding nitro derivative 7 that can be treated with POCl3 to get the chloro compound 8. The chloro compound then can be treated with appropriate amine to produce compound 9 and subsequent protection of the amine will provide compound 10. The alkylation of compound 10 with halide or reductive alkylation using aldehyde will provide compound 11. The deprotection of the protecting group on compound 10 and then cyclization using di-tert-butyl dicarbonate will produce desired compounds of Formula 1B.

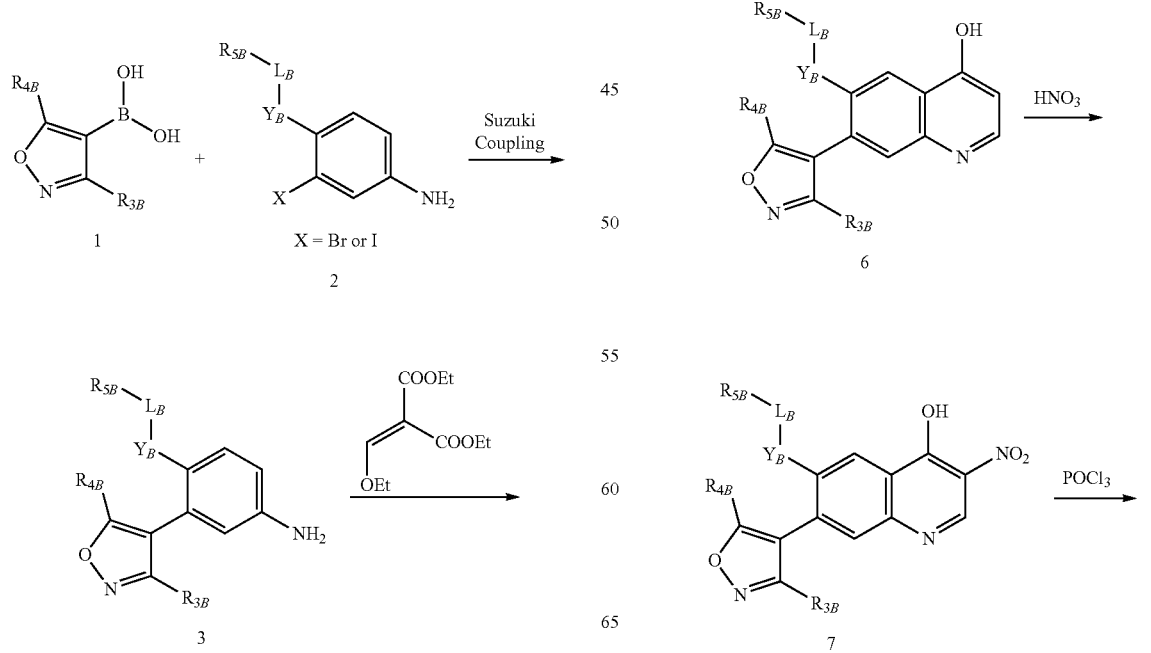

131

-continued

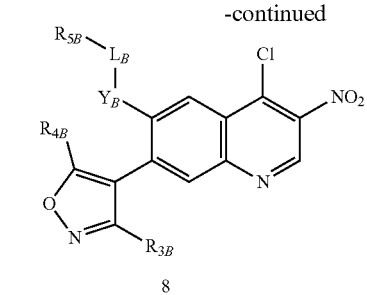
8

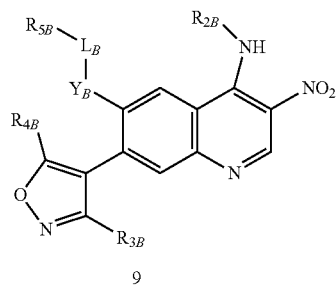
9

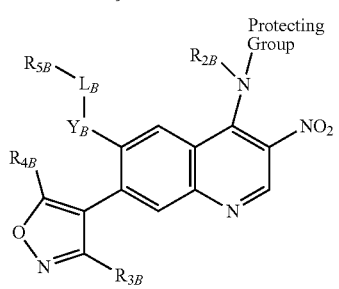
10

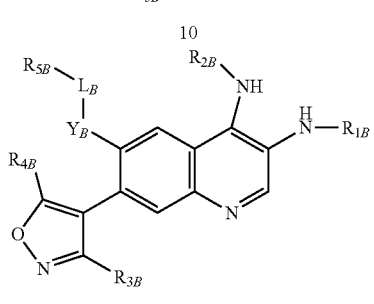
11

Greyhound
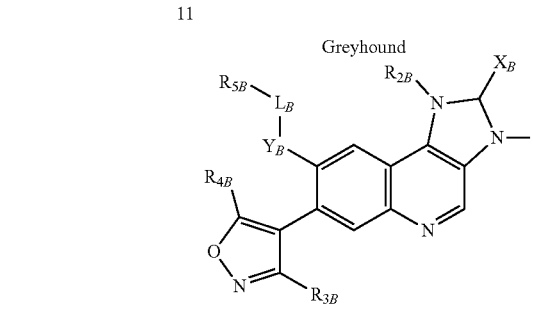
12

Formula 1B

Example 8—Synthetic Scheme

The deprotection of compound 1 will provide compound 2 which can be then reacted with an appropriate side chain with to yield desired compound 3 of Formula 1B.

132

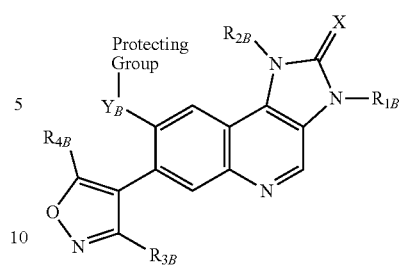
1

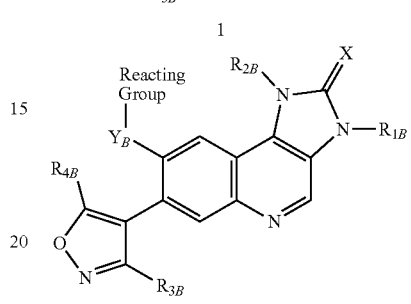
2

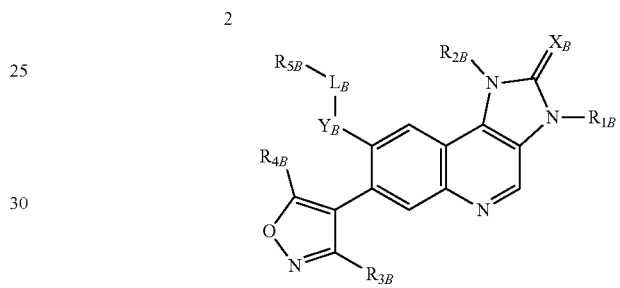
3

Example 9—Synthetic Scheme—Formula 1C

Compounds of Formula 1C may be prepared according to the synthetic scheme set forth below.

The reaction of 4-hydroxyquinolin-2(1H)-one derivative 1 with POCl3 will produce the corresponding dichloro compound 2 and subsequent treatment of compound 2 with aqueous HCl generate compound 3. The alkylation of compound 3 with an appropriate amine will produce the corresponding amino derivative 4 which can be further derivatized to yield compounds of Formula 1C.

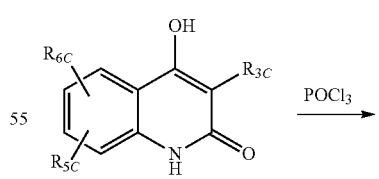
1

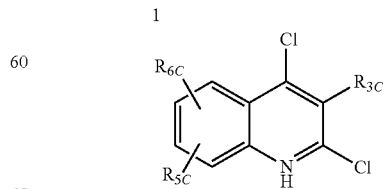
2

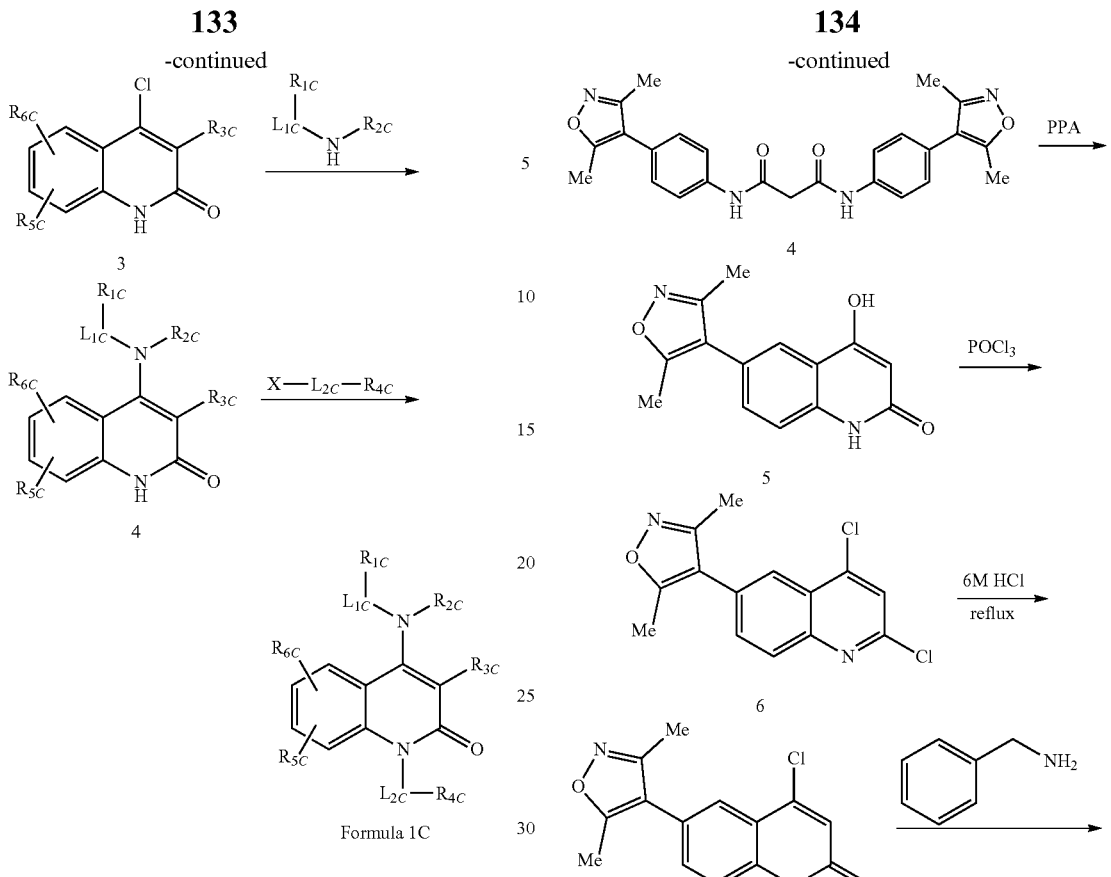

Example 10—Synthetic Scheme

The reaction of 4-bromoaniline with diethyl malonate under heating conditions will produce compound 3 which can be then treated with (3,5-dimethylisoxazol-4-yl)boronic acid under Suzuki reaction conditions to yield compound 4. The compound 4 can be cyclized to produce 6-(3,5-dimethylisoxazol-4-yl)-4-hydroxyquinolin-2(1H)-one by heating with polyphosphoric acid. Further reaction of 5 with POCl3 will yield the dichloro compound 6 and treatment of 6 with aqueous HCl will give compound 7. The reaction of compound 7 with benzylamine will provide the desired compound 8 of the Formula 1C.

Example 11—Synthetic Scheme—Formula 1D

Compounds of Formula 1D may be prepared according to the synthetic scheme set forth below.

The reduction of a substituted nitrobenzene derivative may give the corresponding amino compounds. Compound 2 may be then reacted with diethyl ethoxymethylenemalonate at appropriate temperature with heating conditions to get compound 3. Hydrolysis of compound 3 will provide compound 4 and subsequent decaboxylation will yield compound 5. The reaction of compound 7 with POCl3 may yield the cholro compound 6. The chloro compound then can be treated with appropriate amine to produce compound 7 and subsequent derivatization of 7 can produce compound 8. Deprotection of the compound 8 followed by an appropriate derivatization will provide compound 10 of Formula 1D.

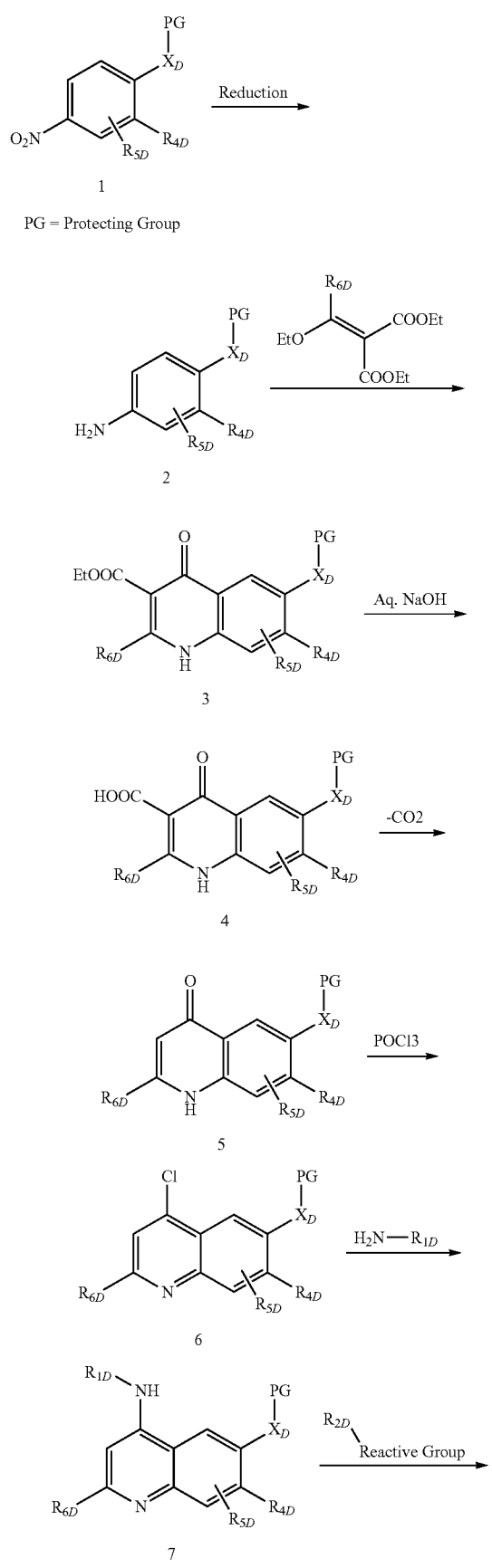
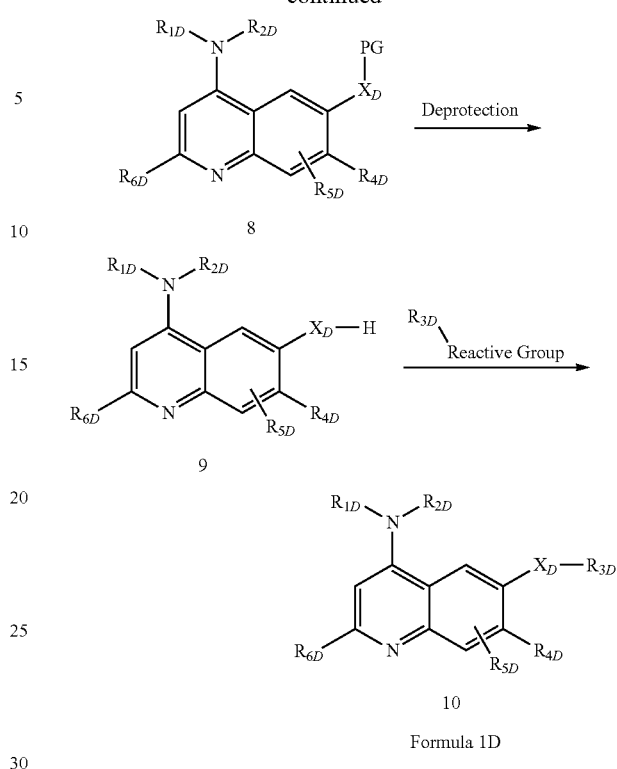

Example 12—Synthetic Scheme

2-Iodo-4-nitrophenol can be reacted with p-methoxybenzoyl chloride to produce PMB protected derivative 2 which than can be treated with (3,5-dimethylisoxazol-4-yl)boronic acid under Suzuki reaction conditions to yield compound 3. After reduction of nitro compound 3 to amino derivative 4, it can be treated with diethyl ethoxymethylenemalonate at appropriate temperature with heating conditions to get compound 5. Hydrolysis of the ester derivative 5 will provide compound 6 and subsequent decaboxylation will yield compound 7. The compound 7 can be treated with POCl3 to get the chloro compound 8. The chloro compound then can be treated with pyridin-2-ylmethanamine to produce compound 9 and subsequent acylation with acetyl chloride of the amine will provide compound 10. The deprotection of the protecting group of phenol of compound 10 will provide the phenolic compound 11 which can be further derivatized using appropriate alkyl halides to produce corresponding compounds 12 and 13 of Formula 1D.

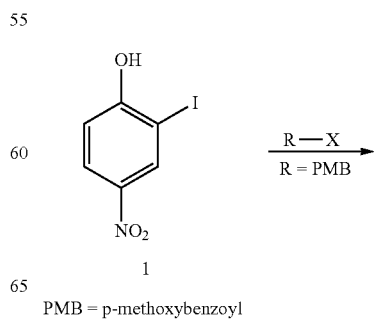

PMB = p-methoxybenzoyl

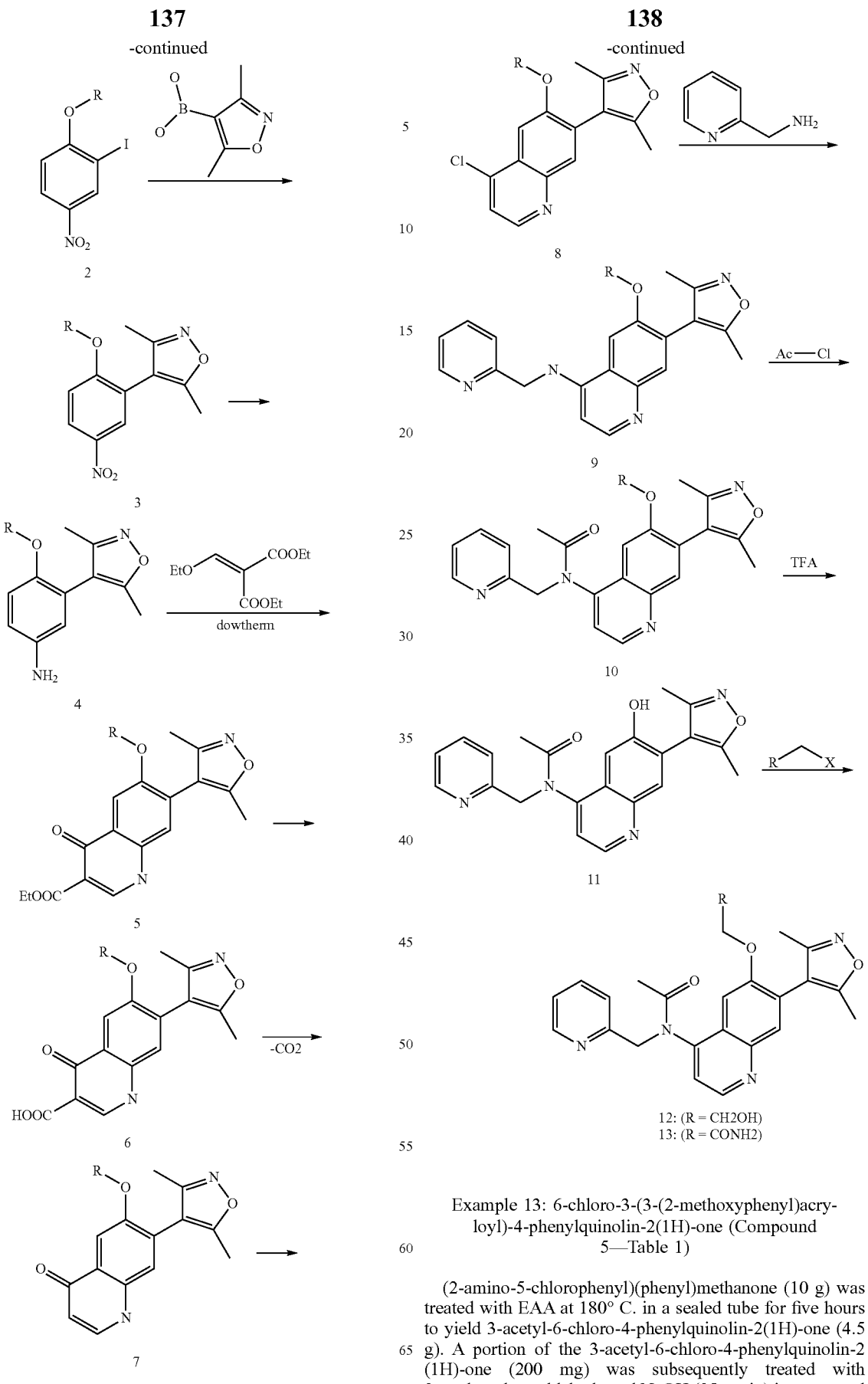
Example 13: 6-chloro-3-(3-(2-methoxyphenyl)acryloyl)-4-phenylquinolin-2(1H)-one (Compound 5—Table 1)
(2-amino-5-chlorophenyl)(phenyl)methanone (10 g) was treated with EAA at 180° C. in a sealed tube for five hours to yield 3-acetyl-6-chloro-4-phenylquinolin-2(1H)-one (4.5 g). A portion of the 3-acetyl-6-chloro-4-phenylquinolin-2 (1H)-one (200 mg) was subsequently treated with 2-methoxybenzaldehyde and NaOH (25 equiv) in water and ethanol at room temperature for 16 hours to yield 6-chloro-3-(3-(2-methoxyphenyl)acryloyl)-4-phenylquinolin-2(1H)-one (60 mg)(LCMS (m/z)=415.10).

Example 14: 6-chloro-3-(3-(3,4-dimethoxyphenyl) acryloyl)-4-phenylquinolin-2(1H)-one (Compound 6—Table 1)

3-acetyl-6-chloro-4-phenylquinolin-2(1H)-one (200 mg) (see Example 1) was treated with 3,4-dimethoxybenzaldehyde and NaOH in water and ethanol at room temperature for 16 hours to yield 6-chloro-3-(3-(3,4-dimethoxyphenyl) acryloyl)-4-phenylquinolin-2(1H)-one (55 mg) (LCMS (m/z)=445.11).

Example 15: 6-chloro-4-phenyl-3-(3-(thiophen-2-yl) acryloyl)quinolin-2(1H)-one (Compound 7—Table 1)

3-acetyl-6-chloro-4-phenylquinolin-2(1H)-one (200 mg) (see Example 1) was treated with thiophene-2-carbaldehyde and NaOH in water and ethanol at room temperature for 16 hours to yield 6-chloro-4-phenyl-3-(3-(thiophen-2-yl)acryloyl)quinolin-2(1H)-one (55 mg) (LCMS (m/z)=391.04).

Example 16: 6-chloro-3-(3-(4-(dimethylamino)phenyl)acryloyl)-4-phenylquinolin-2(1H)-one (Compound 8—Table 1)

3-acetyl-6-chloro-4-phenylquinolin-2(1H)-one (200 mg) was treated with 4-(dimethylamino) benzaldehyde and NaOH in water and ethanol at room temperature for 16 hours to yield 6-chloro-3-(3-(4-(dimethylamino)phenyl)acryloyl)-4-phenylquinolin-2(1H)-one (40 mg) (LCMS (m/z)=428.13).

Example 17: 6-bromo-3-(3-(2,3-dihydrobenzo[b][1,4]dioxin-6-yl)acryloyl)-4-phenylquinolin-2(1H)-one (Compound 9—Table 1)

(2-aminophenyl)(phenyl)methanone (500 mg) was reacted with KBr, ammonium molbedate, and sodium perborate in AcOH at 0° C. for 16 hours to yield (2-amino-5-bromophenyl)(phenyl)methanone (80 mg). A portion of the (2-amino-5-bromophenyl)(phenyl)methanone (200 mg) was treated with EAA at 180° C. in a sealed tube for 10 hours and subsequently washed to yield 3-acetyl-6-bromo-4-phenylquinolin-2(1H)-one (80 mg). A portion of the 3-acetyl-6-bromo-4-phenylquinolin-2(1H)-one (300 mg) was treated with 2,3-dihydrobenzo[b][1,4]dioxine-6-carbaldehyde and NaOH in water and ethanol at room temperature for 16 hours to yield 6-bromo-3-(3-(2,3-dihydrobenzo[b][1,4]dioxin-6-yl)acryloyl)-4-phenylquinolin-2(1H)-one (120 mg).

Example 18: 6-bromo-3-(3-(2,5-dimethoxyphenyl) acryloyl)-4-phenylquinolin-2(1H)-one (Compound 10—Table 1)

3-acetyl-6-bromo-4-phenylquinolin-2(1H)-one (200 mg) (see Example 5) was treated with 2,5-dimethoxybenzaldehyde and NaOH in water and ethanol at room temperature for 16 hours to yield 6-bromo-3-(3-(2,5-dimethoxyphenyl) acryloyl)-4-phenylquinolin-2(1H)-one (55 mg) (LCMS (m/z)=489.06).

Example 19: 6-chloro-3-cinnamoyl-4-(pyridin-4-yl) quinolin-2(1H)-one (Compound 11—Table 1)

4-chloroaniline (2 g) was treated with isonicotinonitrile in the presence of $BCl_3$ and $AlCl_3$ in DCM at 0° C. to 45° C. for 16 hours to yield (2-amino-5-chlorophenyl)(pyridin-4-yl)methanone (300 mg). A portion of the (2-amino-5-chlorophenyl)(pyridin-4-yl)methanone (200 mg) was treated with EAA at 180° C. in a sealed tube for 6 hours to yield 3-acetyl-6-chloro-4-(pyridin-4-yl)quinolin-2(1H)-one (60 mg). A portion of the 3-acetyl-6-chloro-4-(pyridin-4-yl)quinolin-2(1H)-one (200 mg) was treated with benzaldehyde and NaOH in water and ethanol at room temperature for 16 hours to yield 6-chloro-3-cinnamoyl-4-(pyridin-4-yl) quinolin-2(1H)-one (55 mg) (LCMS (m/z)=386.08).

Example 20: 6-chloro-4-(pyridin-3-yl)-3-(3-o-tolylacryloyl)quinolin-2(1H)-one (Compound 12—Table 1)

3-acetyl-6-chloro-4-(pyridin-4-yl)quinolin-2(1H)-one (200 mg)(see Example 7) was treated with 2-methylbenzaldehyde and NaOH in water and ethanol at room temperature for 16 hours to yield 6-chloro-4-(pyridin-3-yl)-3-(3-o-tolylacryloyl)quinolin-2(1H)-one (100 mg).

Example 21: 6-chloro-N-(2-methylbenzyl)-2-oxo-4-phenyl-1,2-dihydroquinoline-3-carboxamide (Compound 13—Table 1)

(2-amino-5-chlorophenyl)(phenyl)methanone (1 g) was treated with diethyl malonate and piperidine at 180° C. in a sealed tube for six hours to yield ethyl 6-chloro-2-oxo-4-phenyl-1,2-dihydroquinoline-3-carboxylate (400 mg). A portion of the obtained ethyl 6-chloro-2-oxo-4-phenyl-1,2-dihydroquinoline-3-carboxylate (380 mg) was treated with aqueous NaOH at room temperature for four hours. The resulting mixture was then heated to 100° C. for twelve hours to yield 6-chloro-2-oxo-4-phenyl-1,2-dihydroquinoline-3-carboxylic acid (200 mg). The obtained 6-chloro-2-oxo-4-phenyl-1,2-dihydroquinoline-3-carboxylic acid (200 mg) was reacted with $COCl_2$ in a $CCl_4$ reflux for three hours. The reaction mixture was concentrated and dissolved in acetone and added to a solution of o-tolylmethanamine and TEA in acetone at 0° C. and stirred at room temperature for three hours to yield 6-chloro-N-(2-methylbenzyl)-2-oxo-4-phenyl-1,2-dihydroquinoline-3-carboxamide (60 mg) (LCMS (m/z)=402.11).

Example 22: 6-chloro-3-cinnamoyl-4-phenyl-1,8-naphthyridin-2(1H)-one (Compound 14—Table 1)

5-chloropyridin-2-amine (20 g) was treated with pivaloyl chloride/TEA in DCM at 0° C. for two hours to yield N-(5-chloropyridin-2-yl)pivalamide (15 g). A portion of the obtained N-(5-chloropyridin-2-yl)pivalamide (10 g) was treated with t-butyl lithium, N-methoxy-N-methylbenzamide in THF at −78° C. for three hours. The reaction mixture was allowed to warm up to room temperature, stirred for three hours and crystallized to yield N-(3-benzoyl-5-chloropyridin-2-yl)pivalamide (4.5 g). The obtained N-(3-benzoyl-5-chloropyridin-2-yl)pivalamide (4.5 g) was reacted with 3N HCl in 1, 4 dioxane at reflux temperature for five hours to yield (2-amino-5-chloropyridin-3-yl)(phenyl) methanone (2.5 g). A portion of the (2-amino-5-chloropyridin-3-yl)(phenyl)methanone (2.0 g) was treated with EAA at 170° C. overnight to yield 3-acetyl-6-chloro-4-phenyl-1,8-naphthyridin-2(1H)-one (400 mg). A portion of the obtained 3-acetyl-6-chloro-4-phenyl-1,8-naphthyridin-2(1H)-one (350 mg) was reacted with benzaldehyde and aqueous NaOH in ethanol at room temperature for eight hours to yield 6-chloro-3-cinnamoyl-4-phenyl-1,8-naphthyridin-2(1H)-one (100 mg).

Example 23: 6-chloro-3-(3-(2-chloro-6-fluorophenyl)acryloyl)-4-(pyridin-4-yl)quinolin-2(1H)-one (Compound 15—Table 1)

3-acetyl-6-chloro-4-(pyridin-4-yl)quinolin-2(1H)-one (200 mg)(see Example 7) was treated with 3,4-dimethoxybenzaldehyde and NaOH in water and ethanol at room temperature for 16 hours to yield 6-chloro-3-(3-(2-chloro-6-fluorophenyl)acryloyl)-4-(pyridin-4-yl)quinolin-2(1H)-one (100 mg) (LCMS (m/z)=439.3).

Example 24: 6-chloro-3-(3-(3-fluoro-5-methylpyridin-4-yl)acryloyl)-4-(pyridin-3-yl)quinolin-2(1H)-one (Compound 16—Table 1)

3-fluoro-5-methylpyridine (1.6 g) was treated with freshly prepared LDA and methyl formate at −78° C. for five hours to yield 3-fluoro-5-methylisonicotinaldehyde (700 mg). 3-acetyl-6-chloro-4-(pyridin-3-yl)quinolin-2(1H)-one (250 mg) was reacted with 3-fluoro-5-methylisonicotinaldehyde (3 equivalents) in aqueous NaOH and ethanol at room temperature for 14 hours to yield 6-chloro-3-(3-(3-fluoro-5-methylpyridin-4-yl)acryloyl)-4-(pyridin-3-yl)quinolin-2(1H)-one (50 mg) (LCMS (m/z)=420.1).

Example 25: 6-chloro-3-(3-(2-chloro-6-fluorophenyl)but-2-enoyl)-4-phenylquinolin-2(1H)-one (Compound 19—Table 1)

(2-amino-5-chlorophenyl)(phenyl)methanone (2 g) was converted to 3-acetyl-6-chloro-4-phenylquinolin-2(1H)-one (800 mg) which, in turn, was converted to 6-chloro-3-(3-(2-chloro-6-fluorophenyl)but-2-enoyl)-4-phenylquinolin-2(1H)-one (225 mg).

Example 26: 3-cinnamoyl-6-(3,6-dimethylisoxazol-4-yl)-4-(pyridin-3-yl)quinolin-2(1H)-one (Compound 20—Table 1)

4-bromoaniline (40 mg) was treated with isonicotinonitrile in the presence of BCl$_3$/AlCl$_3$ in DCM at 0° C. to 45° C. for 16 hours to yield (2-amino-5-bromophenyl)(pyridin-3-yl)methanone (7 g). A portion of the obtained (2-amino-5-bromophenyl)(pyridin-3-yl)methanone (100 mg) was reacted with EAA in ethanol at 180° C. in a sealed tube for 12 hours to yield 3-acetyl-6-bromo-4-(pyridin-3-yl)quinolin-2(1H)-one (20 mg). The aforementioned reaction was repeated to yield additional 3-acetyl-6-bromo-4-(pyridin-3-yl)quinolin-2(1H)-one. A portion of the obtained 3-acetyl-6-bromo-4-(pyridin-3-yl)quinolin-2(1H)-one (400 mg) was treated with benzaldehyde and NaOH (aqueous) in ethanol at room temperature for 16 hours to yield 6-bromo-3-cinnamoyl-4-(pyridin-3-yl)quinolin-2(1H)-one (130 mg). A portion of the 6-bromo-3-cinnamoyl-4-(pyridin-3-yl)quinolin-2(1H)-one 940 mg) was treated with 3,5-dimethylisoxazol-4-ylboronic acid, Pd(dppf)$_2$Cl$_2$, N-methyldicyclohexyl amine, NaOH, in THF at 70° C. for 16 hours to yield 3-cinnamoyl-6-(3,5-dimethylisoxazol-4-yl)-4-(pyridin-3-yl)quinolin-2(1H)-one (6 mg) (LCMS (m/z)=448.04).

Example 27: N1,N3-bis(4-bromophenyl)malonamide

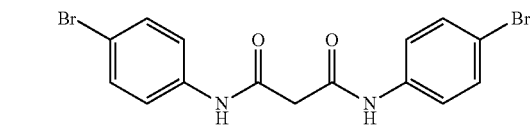 [SMILES: O=C(CC(=O)Nc1ccc(Br)cc1)Nc1ccc(Br)cc1]

4-Bromoaniline (20 mmol) and diethylmalonate (10 mmol) was heated to 150° C. for 20 hr. Reaction was cooled and diluted with ethanol and filtered to give the desired product as a grey solid (1.10 g). $\delta_H$ (DMSO-d$_6$, 400 MHz) 10.32 (s, 2H, 2×NH$_2$), 7.58 (d, 4H, J=9.6, Ar), 7.51 (d, 4H, J=9.6, Ar), 3.48 (s, 2H, CH$_2$); $\delta_C$ (DMSO-d$_6$, 100 MHz) 165.9, 138.7, 132.0, 121.4, 115.4, 46.4.

Example 28: N1,N3-bis(4-(3,6-dimethylisoxazol-4-yl)phenyl)malonamide

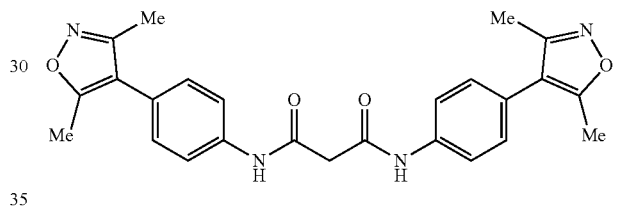

N1,N3-bis(4-bromophenyl)malonamide (0.50 mmol) and isoxazole boronic acid (1.08 mmol) were dissolved in toluene/EtOH (8 mL/8:2). 2M Na$_2$CO$_3$ (735 uL) and palladium tetrakis (113 mg) were added and heated to 90° C. for 5 hr. Reaction was cooled, partitioned between EtOAc and H$_2$O. The organic portion was washed with H$_2$O, sat. NaCl and dried over Na$_2$SO$_4$. Column chromatography gave the desired product as a yellow solid (117 mg). $\delta_H$ (CDCl$_3$, 400 MHz) 9.25 (s, 2H, 2×NH2), 7.66 (d, 4H, J=8.6, Ar), 7.23 (d, 4H, J=8.6, Ar), 3.61 (s, 2H, CH$_2$), 2.39 (s, 3H, Me), 2.56 (s, 3H, Me).

Example 29: 6-(3,5-dimethylisoxazol-4-yl)-4-hydroxyquinolin-2(1H)-one

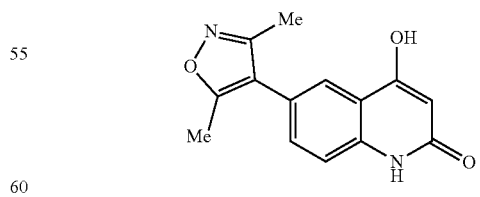

N1,N3-bis(4-(3,5-dimethylisoxazol-4-yl)phenyl)malonamide (117 mg) was treated with polyphosphoric acid (5 eq. by weight) and heated to 140° C. for 5 hr. Reaction was cooled, diluted with H$_2$O and filtered to give the desired product as a white solid (65 mg). $\delta_H$ (DMSO-d$_6$, 400 MHz) 11.43 (br s, 1H, OH), 11.30 (s, 1H, NH), 7.70 (s, 1H, Ar), 7.51 (dd, 1H, J=8.4, 1.6, Ar), 7.35 (d, 1H, J=8.4, Ar), 5.77 (s, 1H, CH), 2.40 (s, 3H, Me), 2.22 (s, 3H, Me).

Example 30: 4-chloro-6-(3,5-dimethylisoxazol-4-yl)quinolin-2(1H)-one

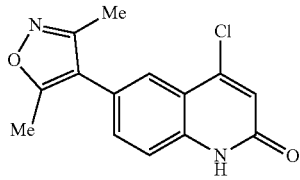 [SMILES: Cc1noc(C)c1-c1ccc2[nH]c(=O)cc(Cl)c2c1]

6-(3,5-dimethylisoxazol-4-yl)-4-hydroxyquinolin-2(1H)-one (40 mg) was treated with NEt₃ (65 uL), POCl₃ (0.5 mL) and heated to 65° C. for 3 hr. Reaction was cooled, partitioned between EtOAc and H₂O. The organic portion was washed with H₂O, sat. NaCl and dried over Na₂SO₄. Column chromatography gave the desired intermediate as a brown solid. The solid was dissolved in dioxane (2 mL) and 6M HCl (2 mL) was added and refluxed for 4 hr. Reaction was cooled, diluted with H₂O, neutralized to pH 9 with solid K₂CO₃ and filtered to give the desired product as a cream solid (34 mg). $\delta_H$ (DMSO-d₆, 400 MHz) 12.15 (s, 1H, NH), 7.78 (s, 1H, Ar), 7.67 (d, 1H, J=8.4, Ar), 7.48 (d, 1H, J=8.4, Ar), 6.89 (s, 1H, CH), 2.42 (s, 3H, Me), 2.24 (s, 3H, Me).

Example 31: 4-(benzylamino)-6-(3,5-dimethylisoxazol-4-yl)quinolin-2(1H)-one

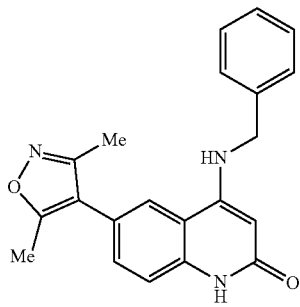 [SMILES: Cc1noc(C)c1-c1ccc2[nH]c(=O)cc(NCc3ccccc3)c2c1]

4-chloro-6-(3,5-dimethylisoxazol-4-yl)quinolin-2(1H)-one was heated to 120° C. in a 1:1 mixture of DMSO and benzylamine. Reaction was cooled, partitioned between EtOAc and H₂O. The organic portion was washed with H₂O, sat. NaCl and dried over Na₂SO₄. Column chromatography gave the desired product as a cream solid (10 mg) after lyophilization. $\delta_H$ (DMSO-d₆, 400 MHz) 10.86 (s, 1H, NH), 7.99 (s, 1H, Ar), 7.71 (t, 1H, J=5.2, NH), 7.56 (d, 1H, J=8.8, Ar), 7.40-7.21 (m, 6H, Ar), 5.16 (s, 1H, CH), 4.46 (d, 2H, J=5.2, CH₂), 2.42 (s, 3H, Me), 2.26 (s, 3H, Me).

Example 32: 4-(2-chlorobenzylamino)-6-(3,5-dimethylisoxazol-4-yl)quinolin-2(1H)-one

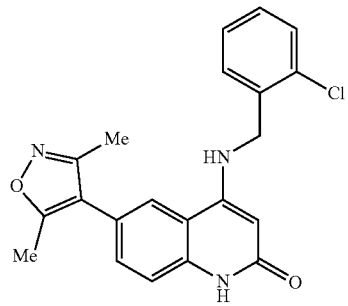 [SMILES: Cc1noc(C)c1-c1ccc2[nH]c(=O)cc(NCc3ccccc3Cl)c2c1]

A similar procedure as set forth in Example 16 gave the desired product as a cream solid (15 mg). $\delta_H$ (DMSO-d₆, 400 MHz) 10.94 (s, 1H, NH), 8.01 (s, 1H, Ar), 7.18 (t, 1H, J=5.6, NH), 7.53-7.47 (m, 2H, Ar), 7.39-7.30 (m, 4H, Ar), 5.06 (s, 1H, CH), 4.52 (d, 2H, J=5.6, CH₂), 2.44 (s, 3H, Me), 2.28 (s, 3H, Me).

Example 33: 6-(3,5-dimethylisoxazol-4-yl)-4-morpholinoquinolin-2(1H)-one

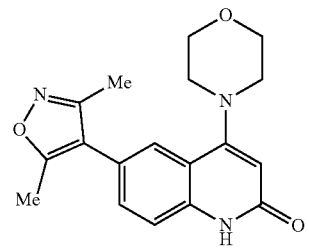 [SMILES: Cc1noc(C)c1-c1ccc2[nH]c(=O)cc(N3CCOCC3)c2c1]

A similar procedure as set forth in Example 16 gave the desired product as a white solid (12 mg). $\delta_H$ (DMSO-d₆, 400 MHz) 11.51 (s, 1H, NH), 7.60 (s, 1H, Ar), 7.54 (d, 1H, J=8.8, Ar), 7.40 (d, 1H, J=8.8, Ar), 5.94 (s, 1H, CH), 3.88-3.80 (m, 4H, Ar), 3.12-3.05 (m, 4H, Ar), 2.43 (s, 3H, Me), 2.25 (s, 3H, Me).

Example 34: 6-(3,5-dimethylisoxazol-4-yl)-4-(piperidin-1-yl)quinolin-2(1H)-one

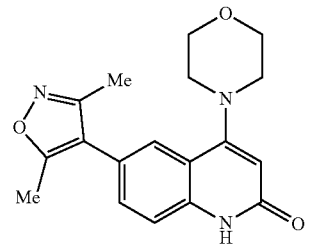 [SMILES: Cc1noc(C)c1-c1ccc2[nH]c(=O)cc(N3CCOCC3)c2c1]

A similar procedure as set forth in Example 16 gave the desired product as a cream solid (6 mg). $\delta_H$ (DMSO-d₆, 400 MHz) OH (DMSO-d₆, 400 MHz) 11.43 (s, 1H, NH), 7.55-7.50 (m, 2H, Ar), 7.38 (d, 1H, J=8.4, CH₂), 5.87 (s, 1H, CH), 3.20-3.01 (m, 4H, Ar), 2.44 (s, 3H, Me), 2.26 (s, 3H, Me), 1.79-1.70 (m, 4H, Ar), 1.67-1.58 (m, 2H, Ar).

Biological Assays

Example 35: In Vitro Cell Viability

MV4-11 acute myeloid leukemia cells (American Type Culture Collection, Manassas, Va.) were added to 96-well clear bottom assay plates containing RPMI-1640 medium supplemented with 10% fetal bovine serum (FBS) at approximately 30,000 cells/well and incubated for 24 hours at 37° C. with 5% $CO_2$ and 95% humidity. Control wells containing no cells were included to measure background fluorescence signal. Test compounds were dissolved at 10-20 µM and diluted two-fold in DMSO to produce a working stock of compound solutions. Aliquots of the working stock solutions were subsequently diluted 100-fold in basal RPMI-1640 medium which was then further diluted 10-fold to the assay plate containing the cells to provide 10 test concentrations ranging from 0.04 µM-20 µM. Following a 72-hour incubation period, viability of the cells was determined by the alamarBlue® assay (Life Technologies, Carlsbad, Calif.) following the manufacturer's protocol. Prior to generation of dose response curves, the data were background subtracted using the no cell control values (mean+/−standard deviation) and fluorescence values versus $Log_{10}$ concentration of test compounds were plotted using GraphPad Prism. The resulting sigmoidal curve was then fit to the graph and $IC_{50}$ values were calculated using a 4 parameter (4PL) algorithm using the following equation: 4(PL) $F(x)=(A-D)/(1+(x/c)^B)+D$, where A=lower asymptote (baseline response), D=upper asymptote (maximum response), C=drug concentration that provokes a response halfway between A and D, B=slope of the curve. The results for selected compounds are set forth in Table 7.

TABLE 7

| Compound | In Vitro Cell Viability ($IC_{50}$) | |
| --- | --- | --- |
| (Table 1) | MV4-11 Cells (AML) | MM1.S Cells (Multiple Myeloma) |
| 1 | 0.11 µM | |
| 5 | 1.49 µM | 2.53 µM |
| 6 | 3.57 µM | 31.9 µM |
| 7 | 2.3 µM | |
| 8 | 10.31 µM | |
| 9 | 5.52 µM | |
| 10 | 1.75 µM | 3 µM |
| 11 | 0.97 µM | 4.21 µM |
| 12 | 1.04 µM | 2.44 µM |
| 13 | 4.73 µM | 3.1 µM |
| 14 | 0.71 µM | 14.1 µM |
| 15 | 1.18 µM | |
| 16 | 0.4 µM | |
| 21 | 8.6 µM | |
| 22 | 1.8 µM | |
| 81 | 3 µM | |
| 127 | 5.45 µM | |
| 147 | 0.22 µM | |
| 148 | 0.25 µM | |

Example 36: Gene Expression Change of MYC Oncogene

Approximately $1\times10^6$ MV4-11 were exposed to either DMSO as vehicle control or test compounds at 10 µM for one hour in RPMI medium supplemented with 10% FBS. Total RNA was prepared from the exposed cells using RNeasy® Mini Kit (Qiagen, Venlo, Netherlands) and reverse transcription was performed with qScript™ cDNA SuperMix (Quanta BioSciences, Gaithersburg, Md.) following manufacturers' protocols to yield complementary DNA (cDNA). Quantitative polymerase chain reaction was performed on MX3000 7500 Real-Time PCR system (Agilent Technologies, Santa Clara, Calif.) using cDNA derived from approximately 50 ng of total RNA and PerfeCTa® SYBR® Green FastMix® (Quanta BioSciences) with a thermal profile consisting of denaturation at 95° C. for 10 min followed by 40 cycles of denaturation at 95° C. for 10 seconds and annealing/elongation at 60° C. for 30 seconds. The expression of MYC gene was detected by using the forward primer 5'-CTG GTG CTC CAT GAG GAG A-3' and reverse primer 5'-CCT GCC TCT TTT CCA CAG AA-3' while the expression of GAPDH gene was measured with GAPDH PerfeCTa® Reference Gene Assay primers (Quanta BioSciences). Critical threshold (CT) values were obtained with MX Pro software (Agilent Technologies) and the gene expression fold changes were calculated for both MYC and GAPDH genes compared to vehicle control assuming that 1 CT value change corresponds to two-fold difference in gene expressions. MYC gene expression fold changes were then divided by the values for GAPDH gene in order to account for sample-to-sample loading differences. The results for selected compounds are set forth in Table 8.

TABLE 8

| Compound (Table 1) | Gene Expression Change of MYC Oncogene (in vitro) MV4-11 Cells (AML)-Fold Change |
| --- | --- |
| 1 | −1.4/−1.3 |
| 2 | −1.4 |
| 3 | −1.4 |
| 4 | −1.4 |
| 5 | −1.6 |
| 6 | −1.7 |
| 7 | −1.3 |
| 8 | −1.3 |
| 10 | −1.3 |
| 11 | −3.0 |
| 12 | −2.8 |
| 13 | −1.3 |
| 14 | −3.0 |
| 15 | −2.3 |
| 21 | −1.2 |
| 22 | −1.1 |
| 23 | −1.0 |
| 24 | −1.2 |
| 70 | −1.2 |
| 71 | −1.1 |
| 72 | −1.3 |
| 73 | −1.5 |
| 74 | −1.0 |
| 75 | −1.5 |
| 76 | −1.3 |
| 77 | −1.2 |
| 78 | −1.5 |
| 79 | −1.1 |
| 80 | −1.3 |
| 81 | −1.9 |
| 82 | −1.2 |
| 90 | −3.0 |
| 91 | −1.3 |
| 92 | −1.5 |
| 93 | −1.6 |
| 94 | −1.2 |
| 95 | −1.4 |
| 96 | −1.3 |
| 97 | −1.5 |
| 98 | −1.5 |
| 99 | −1.4 |
| 100 | −1.0 |
| 101 | −1.5 |

TABLE 8-continued

| Compound (Table 1) | Gene Expression Change of MYC Oncogene (in vitro) MV4-11 Cells (AML)-Fold Change |
|---|---|
| 102 | −1.1 |
| 143 | −1.2 |
| 144 | −1.6/−1.7 |
| 145 | −1.6/−1.6 |

Example 37: Amplified Luminescent Proximity Homogeneous Assay (ALPHA)

The interactions between test compounds and BRD4 protein containing both bromodomain 1 and bromodomain 2 were measured with human BRD4 protein with N-terminal His tag (BPS Bioscience, San Diego, Calif.) using AlphaScreen® assay at room temperature. A 9 µl reaction mixture in BRD Assay Buffer (BPS Bioscience) containing 25 nM BRD4 and test compounds at various concentrations were incubated for 30 minutes followed by additional 30-minute incubation with 1 µl of 20 µM histone H4 peptide (residue 1-21) in the presence of 5% DMSO. Test compounds (see Table 4) were assayed at 10 µM or 31.6 µM for screening purpose, while 8 different concentrations (10 nM-10 µM) were used for $IC_{50}$ measurements. After the incubation, 20 µl of BRD Detection Buffer (BPS Bioscience) containing 10 µg/ml Glutathione Acceptor beads and 10 µg/ml Streptavidin Donor beads (PerkinElmer, Waltham, Mass.) was added and the mixture was incubated for 50 minutes in darkroom. Binding measurements were taken in duplicate at each concentration using EnSpire® Alpha Multimode Plate Reader Model 2390 (PerkinElmer). The AlphaScreen data were analyzed using Graphpad Prism (La Jolla, Calif.). In the absence of the compound, the AlphaScreen signal ($A_t$) in each data set was defined as 100% activity. In the absence of the histone H4 peptide ligand, the AlphaScreen signal ($A_b$) in each data set was defined as 0% activity. The percent activity in the presence of each compound was calculated according to the following equation: % activity=$[(A-A_b)/(A_t-A_b)] \times 100$, where A=the AlphaScreen signal in the presence of compound; $A_b$=the AlphaScreen signal in the absence of the histone peptide ligand; and $A_t$=the AlphaScreen signal in the absence of the compound. The percent inhibition was calculated according to the following equation: % inhibition=100−% activity.

The inhibitory effects of select compounds from Table 1 are shown in Table 9.

TABLE 9

| Compound (Table 1) | BRD4-BD1-BD2 | |
|---|---|---|
| | $IC_{50}$ | % Inhibition |
| 1 | 2.43 µM | 87% |
| 83 | 442 nM | 99% |
| 84 | 372 nM | 98% |
| 85 | 876 nM | 99% |
| 86 | 670 nM | 99% |
| 87 | 139 nM | 99% |
| 88 | 864 nM | 98% |
| 89 | 586 nM | 99% |
| 90 | 11.2 µM | 62% |
| 97 | 5.8 µM | 59% |
| 98 | 6.7 µM | 64% |
| 121 | 7.3 µM | 68% |
| 122 | 26.8 µM | 65% |
| 124 | 17.3 µM | 50% |
| 126 | 23.6 µM | 50% |

TABLE 9-continued

| Compound (Table 1) | BRD4-BD1-BD2 | |
|---|---|---|
| | $IC_{50}$ | % Inhibition |
| 128 | 16.3 µM | 64% |
| 132 | 3.7 µM | 92% |
| 143 | | 99% |
| 144 | 0.049 µM | >90% |
| 145 | 1.44 µM | 72% |

Example 38: Amplified Luminescent Proximity Homogeneous Assay (ALPHA)

Assays were performed by AlphaScreening technology using a recombinant BRD4-BD1-BD2 and BET Ligand. The AlphaScreening signal from the assay was correlated with the amount of BET Ligand binding to the bromodomain. The compounds were diluted in 50% DMSO and 1 µl of the dilution was added to a 10 µl reaction so that the final concentration of DMSO is 5% in all of reactions. All reactions were conducted at room temperature. The 9 µl reaction mixture in BRD Assay Buffer contains 2.5 nM BRD4-BD1-BD2 and the indicated amount of the inhibitor, and the reaction mixture were incubated for 30 min followed by additional 30 min incubation after the addition of 1 µl of BET Ligand (Table 2.3.1). For the negative control (blank), 1 µl of the assay buffer was added instead of the BET Ligand. After the 30 min incubation with the BET Ligand, 20 µl of BRD Detection buffer containing 10 µg/ml Glutathione acceptor beads and 10 µg/ml Streptavidin Donor beads was added and the final 30 JAI mixture was incubated for 50 min in a dark room.

AlphaScreening signal was measured using EnSpire Alpha 2390 Multilabel reader (Perkin Elmer). Binding experiments were performed in duplicate at each concentration. The AlphaScreening data were analyzed using the computer software, Graphpad Prism. In the absence of the compound, the AlphaScreening signal ($A_t$) in each data set was defined as 100% activity. In the absence of the BET Ligand, the AlphaScreening signal ($A_b$) in each data set was defined as 0% activity. The percent activity in the presence of each compound was calculated according to the following equation: % activity=$[(A-A_b)/(A_t-A_b)] \times 100$, where A=the AlphaScreening signal in the presence of the compound, $A_b$=the AlphaScreening signal in the absence of the BET Ligand, and $A_t$=the AlphaScreening signal in the absence of the compound. The percent inhibition was calculated for certain compounds according to the following equation: % inhibition=100−% activity.

The inhibitory effects of select compounds are shown in Table 10.

TABLE 10

| Compound Structure | % inhibition at 10 µM |
|---|---|
| 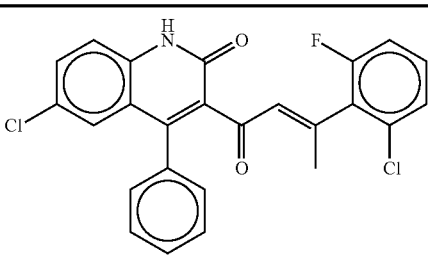 | 50 |

TABLE 10-continued

| Compound Structure | % inhibition at 10 μM |
|---|---|
| (6-(3,5-dimethylisoxazol-4-yl)-4-hydroxyquinolin-2(1H)-one) | 51 |
| (6-(3,5-dimethylisoxazol-4-yl)-3-cinnamoyl-4-(pyridin-3-yl)quinolin-2(1H)-one) | 62 |
| (7-(3,5-dimethylisoxazol-4-yl)-6-methoxy-3-(diethylcarbamothioyl)-4-phenylquinolin-2(1H)-one) | 65 |
| (6-chloro-3-((5-(p-tolyl)-4-(benzylideneamino)-4H-1,2,4-triazol-3-yl)thio)-4-phenylquinolin-2(1H)-one) | 70 |
| (6-chloro-3-((5-(p-tolyl)-4-(benzylideneamino)-4H-1,2,4-triazol-3-yl)thio)-4-phenylquinolin-2(1H)-one isomer) | 71 |

TABLE 10-continued

| Compound Structure | % inhibition at 10 μM |
|---|---|
| (1-benzyl-6-(3,5-dimethylisoxazol-4-yl)-4-phenylquinolin-2(1H)-one) | 74 |
| (6-(3,5-dimethylisoxazol-4-yl)-4-phenylquinolin-2(1H)-one) | 82 |
| (7-(3,5-dimethylisoxazol-4-yl)-4-phenylquinolin-2(1H)-one) | 85 |
| (6-chloro-1-(4-methoxybenzyl)-3-(2-methyloxazol-4-yl)-4-(phenylsulfonyloxy)quinolin-2(1H)-one) | 98 |

TABLE 10-continued

| Compound Structure | % inhibition at 10 μM |
|---|---|
| 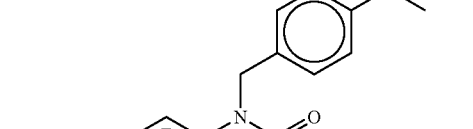 | 98 |
| 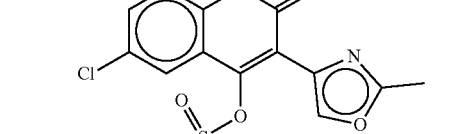 | 99 |
| 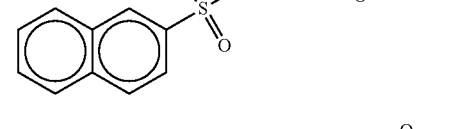 | 99 |
| 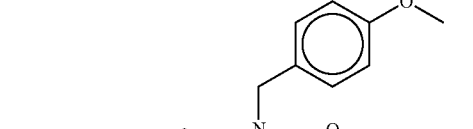 | 99 |

TABLE 10-continued

| Compound Structure | % inhibition at 10 μM |
|---|---|
| 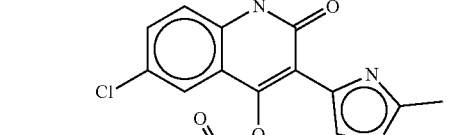 | 99 |
| 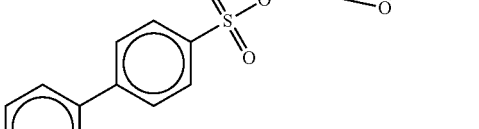 | 99 |
| 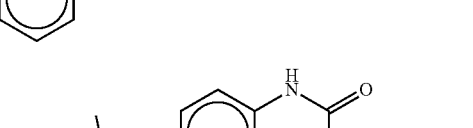 | 99 |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A method of treating a disease or condition selected from fibrosis, inflammation, and lung cancer in a patient in need thereof, comprising administering to the patient a compound of Formula IC:

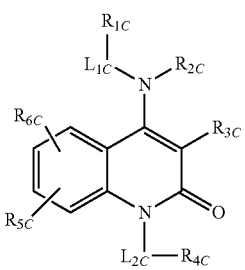

Formula IC or a pharmaceutically acceptable salt thereof, wherein:
$R_{6C}$ is:

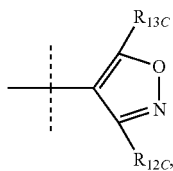

wherein $R_{12C}$ and $R_{13C}$ are independently selected from hydrogen, hydroxyl, sulfhydryl, alkoxy, thioalkoxy, alkyl and halogen;

$L_{1C}$ is $-(CR_{10C}R_{11C})_{nC}$ wherein $R_{10C}$ and $R_{11C}$ are independently selected from hydrogen and alkyl; and nc is 0, 1, 2, or 3;

$L_{2C}$ is selected from the group consisting of $-(CR_{10C}R_{11C})_{n}-$, $-CON(R_{7C})-$, $-SO_2N(R_{7C})-$, $-NR_{7C}CON(R_{8C})-$, and $-OCON(R_{7C})$; and n is 0, 1, 2, or 3;

$R_{1C}$ is selected from alkyl, substituted or unsubstituted aryl, substituted or unsubstituted heteroaryl, substituted or unsubstituted cycloalkyl and substituted or unsubstituted heterocycloalkyl wherein the heteroaryl and heterocycloalkyl include one or more nitrogen, oxygen or sulfur as a heteroatom, and wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}$, $CONR_{7C}R_{8C}$, $NR_{7C}R_{8C}$, $NR_{7C}COR_{8C}$, $NR_{7C}SO_2R_{8C}$, $NR_{9C}CONR_{7C}R_{8C}$;

$R_{2C}$ is hydrogen or alkyl;

optionally, $R_{1C}$ and $R_{2C}$ are connected to make a substituted or unsubstituted cycloalkyl and substituted or unsubstituted heterocycloalkyl wherein the heteroatom is nitrogen, oxygen or sulfur; wherein said substitutions are selected from hydrogen, hydroxyl, sulfhydryl, alkoxy, thioalkoxy, alkyl, halogen, CN, $CF_3$, $NO_2$, $COOR_7$, $NC(O)OR_{7C}$, $CONR_{7C}R_{8C}$, $NR_7R_{8C}$, $NR_{7C}COR_{8C}$, $NR_{7C}SO_2R_{8C}$, $NR_{7C}CONR_{8C}R_{9C}$;

$R_{3C}$ is hydrogen or alkyl;

$R_{4C}$ is selected from hydrogen, alkyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include one or more nitrogen, oxygen or sulfur as a heteroatom;

wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}$, $CONR_{7C}R_{8C}$, $NR_{7C}R_{8C}$, $NR_{7C}COR_{8C}$, $NR_{7C}SO_2R_{8C}$, $NR_{7C}CONR_{8C}R_{9C}$;

$R_{5C}$ is selected from hydrogen, alkyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include one or more nitrogen, oxygen or sulfur as a heteroatom; wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}C$, $CONR_{7C}R_{8C}$, $NR_{7C}R_{8C}$, $NR_{7C}COR_{8C}$, $NR_{7C}SO_2R_{8C}$, $NR_{7C}CONR_{8C}R_{9C}$;

$R_{7C}$, $R_{8C}$ and $R_{9C}$ are each independently selected from hydrogen, alkyl, heteroalkyl, substituted or unsubstituted aryl, substituted or unsubstituted arylalkyl, substituted or unsubstituted heteroaryl, substituted or unsubstituted heteroarylalkyl, substituted or unsubstituted cycloalkyl, and substituted or unsubstituted heterocycloalkyl; and or optionally, $R_{7C}$ and $R_{8C}$, along with the atoms to which they are attached form a 4, 5, 6 or 7-member cyclic ring system, which is optionally substituted with one or more substituents selected from hydrogen, hydroxyl, sulfhydryl, alkoxy, thioalkoxy, alkyl and halogen.

2. The method of claim 1, wherein $R_{1C}$ is substituted or unsubstituted aryl, or substituted or unsubstituted heteroaryl.

3. The method of claim 1, wherein $L_{1C}$ is $-(CR_{10C}R_{11C})_{nC}$, wherein $R_{10C}$ and $R_{11C}$ are each hydrogen or methyl and nc is 1 or 2.

4. The method of claim 1, wherein $L_{2C}$-$R_{4C}$ is methyl.

5. The method of claim 1, wherein $R_{2C}$ is H.

6. The method of claim 1, wherein $R_{3C}$ is H.

7. The method of claim 1, wherein $R_{5C}$ is H.

8. The method of claim 1, wherein $R_{6C}$ is

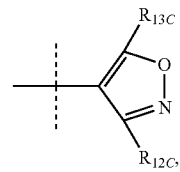

wherein $R_{12C}$ and $R_{13C}$ are independently selected $C_{1-6}$ alkyl groups.

9. The method of claim 1, wherein $R_{6C}$ is

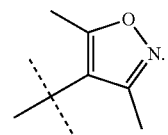

10. The method of claim 1, wherein:
$L_{1C}$ is $-(CR_{10C}R_{11C})_{nC}$ wherein $R_{10C}$ and $R_{11C}$ are independently selected from hydrogen and methyl; and nc is 1 or 2;
$L_{2C}$-$R_{4C}$ is methyl;
$R_{1c}$ is $C_{1-6}$ alkyl, halogen-substituted phenyl, unsubstituted phenyl, or unsubstituted 5-7 membered heteroaryl, wherein the heteroaryl includes 1, 2, or 3 heteroatoms selected from nitrogen, oxygen, and sulfur;
$R_{2C}$ is hydrogen;
$R_{3C}$ is hydrogen; and
$R_{5C}$ is hydrogen.

11. The method of claim 1, wherein $R_{1C}$ is selected from substituted or unsubstituted aryl, or substituted or unsubstituted heteroaryl; $R_{2C}$ and $R_{3C}$ are hydrogen; $R_{4C}$ is selected from substituted or unsubstituted aryl, or substituted or unsubstituted heteroaryl; $R_{5C}$ is selected from substituted or unsubstituted aryl, or substituted or unsubstituted heteroaryl;
$L_{1C}$ is $-(C-R_{10C}R_{11C})_{nC}-$ wherein $R_{10C}$ and $R_{11C}$ are independently selected from hydrogen and methyl and nC is 1 or 2; and $L_{2C}$ is $-(CR_{10C}R_{11C})_{n}-$, wherein n is 0, 1, 2, or 3.

12. The method of claim 1, wherein the compound of Formula IC is a compound of Formula IC', and is selected from the compounds defined according to the following Table:

Formula IC'

[Structure: quinolin-2(1H)-one core with $R_{1C}$ and $L_{1C}$ on N at the 4-amino position with $R_{2C}$; $R_{3C}$ at C3; $R_{6C}$ at position 4; $R_{5C}$ at position 1 of benzo ring; $L_{2C}-R_{4C}$ on ring N]

| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| phenyl | H | H | H | H | 3,5-dimethylisoxazol-4-yl, 3 | $-CH_2-$ | $-CH_2-$ |
| phenyl | $CH_3$ | H | H | H | 3,5-dimethylisoxazol-4-yl, 3 | $-CH_2-$ | $-CH_2-$ |
| phenyl | H | H | H | 2, $CH_3$ | 3,5-dimethylisoxazol-4-yl, 3 | $-CH_2-$ | $-CH_2-$ |
| phenyl | $CH_3$ | H | H | 2, $CH_3$ | 3,5-dimethylisoxazol-4-yl, 3 | $-CH_2-$ | $-CH_2-$ |
| 2-chlorophenyl | H | H | H | 2, $CH_3$ | 3,5-dimethylisoxazol-4-yl, 3 | $-CH_2-$ | bond |
| 2-chlorophenyl | $CH_3$ | H | H | 2, $CH_3$ | 3,5-dimethylisoxazol-4-yl, 3 | $-CH_2-$ | bond |

Formula IC'

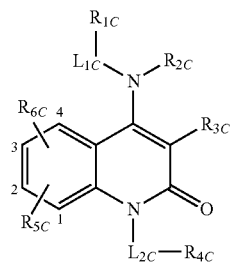

| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 2-Cl-phenyl | H | H | H | H | 3, dimethylisoxazol-4-yl | —CH$_2$— | —CH$_2$— |
| 2-Cl-phenyl | CH$_3$ | H | H | H | 3, dimethylisoxazol-4-yl | —CH$_2$— | —CH$_2$— |
| 2-Cl-phenyl | H | H | H | 2, CH$_3$ | 3, dimethylisoxazol-4-yl | —CH$_2$— | —CH$_2$— |
| 2-Cl-phenyl | CH$_3$ | H | H | 2, CH$_3$ | 3, dimethylisoxazol-4-yl | —CH$_2$— | —CH$_2$— |
| phenyl | H | CH$_3$ | H | H | 3, dimethylisoxazol-4-yl | —CH$_2$— | —CH$_2$— |
| phenyl | CH$_3$ | CH$_3$ | H | H | 3, dimethylisoxazol-4-yl | —CH$_2$— | —CH$_2$— |
| phenyl | H | CH$_3$ | H | 2, CH$_3$ | 3, dimethylisoxazol-4-yl | —CH$_2$— | —CH$_2$— |
| phenyl | CH$_3$ | CH$_3$ | H | 2, CH$_3$ | 3, dimethylisoxazol-4-yl | —CH$_2$— | —CH$_2$— |

Formula IC'

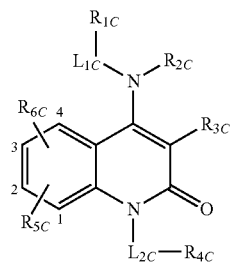

| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 2-Cl-phenyl | H | CH₃ | H | H | 3, dimethylisoxazolyl | —CH₂— | —CH₂— |
| 2-Cl-phenyl | CH₃ | CH₃ | H | H | 3, dimethylisoxazolyl | —CH₂— | —CH₂— |
| 2-Cl-phenyl | H | CH₃ | H | 2, CH₃ | 3, dimethylisoxazolyl | —CH₂— | —CH₂— |
| 2-Cl-phenyl | CH₃ | CH₃ | H | 2, CH₃ | 3, dimethylisoxazolyl | —CH₂— | —CH₂— |
| phenyl | H | H | H | 2, dimethylisoxazolyl | 3, dimethylisoxazolyl | —CH₂— | —CH₂— |
| phenyl | CH₃ | H | H | 2, dimethylisoxazolyl | 3, dimethylisoxazolyl | —CH₂— | —CH₂— |
| phenyl | H | H | H | 2, Ph | 3, dimethylisoxazolyl | —CH₂— | —CH₂— |
| phenyl | CH₃ | H | H | 2, Ph | 3, dimethylisoxazolyl | —CH₂— | —CH₂— |

Formula IC'

[Structure: quinolin-2(1H)-one core with R1C-L1C-N(R2C) at position 4, R3C at position 3, L2C-R4C on N1, R5C at position 1 (aromatic), R6C at position 4 (aromatic), positions 2 and 3 on benzene ring]

| R1C | R2C | R3C | R4C | Position, R5C | Position, R6C | L1C | L2C |
|---|---|---|---|---|---|---|---|
| 2-chlorophenyl | H | H | H | 2, 3,5-dimethylisoxazol-4-yl at position 3 | 3,5-dimethylisoxazol-4-yl | —CH2— | —CH2— |
| 2-chlorophenyl | CH3 | H | H | 2, 3,5-dimethylisoxazol-4-yl at position 3 | 3,5-dimethylisoxazol-4-yl | —CH2— | —CH2— |
| 2-chlorophenyl | H | H | H | 2, Ph | 3,5-dimethylisoxazol-4-yl at position 3 | —CH2— | —CH2— |
| 2-chlorophenyl | CH3 | H | H | 2, Ph | 3,5-dimethylisoxazol-4-yl at position 3 | —CH2— | —CH2— |
| phenyl | H | CH3 | H | 2, 3,5-dimethylisoxazol-4-yl at position 3 | 3,5-dimethylisoxazol-4-yl | —CH2— | —CH2— |
| phenyl | CH3 | CH3 | H | 2, 3,5-dimethylisoxazol-4-yl at position 3 | 3,5-dimethylisoxazol-4-yl | —CH2— | —CH2— |
| phenyl | H | CH3 | H | 2, Ph | 3,5-dimethylisoxazol-4-yl at position 3 | —CH2— | —CH2— |
| phenyl | CH3 | CH3 | H | 2, Ph | 3,5-dimethylisoxazol-4-yl at position 3 | —CH2— | —CH2— |

-continued

Formula IC'

[Structure: quinolin-2(1H)-one core with R1C-L1C-N(R2C)- at position 4, R3C at position 3, L2C-R4C at N1, R5C at position 1/2, R6C at position 3/4]

| R1C | R2C | R3C | R4C | Position, R5C | Position, R6C | L1C | L2C |
|---|---|---|---|---|---|---|---|
| 2-chlorophenyl | H | CH₃ | H | 2, 3,4-dimethylisoxazol-4-yl (pos 3) | 3,5-dimethylisoxazol-4-yl | —CH₂— | —CH₂— |
| 2-chlorophenyl | CH₃ | CH₃ | H | 2, 3,5-dimethylisoxazol-4-yl (pos 3) | 3,5-dimethylisoxazol-4-yl | —CH₂— | —CH₂— |
| 2-chlorophenyl | H | CH₃ | H | 2, Ph | 3,5-dimethylisoxazol-4-yl (pos 3) | —CH₂— | —CH₂— |
| 2-chlorophenyl | CH₃ | CH₃ | H | 2, Ph | 3,5-dimethylisoxazol-4-yl (pos 3) | —CH₂— | —CH₂— |
| phenyl | H | H | Ph | H | 3,5-dimethylisoxazol-4-yl (pos 3) | —CH₂— | —CH₂— |
| phenyl | CH₃ | H | Ph | H | 3,5-dimethylisoxazol-4-yl (pos 3) | —CH₂— | —CH₂— |
| phenyl | H | H | Ph | 2, CH₃ | 3,5-dimethylisoxazol-4-yl (pos 3) | —CH₂— | —CH₂— |
| phenyl | CH₃ | H | Ph | 2, CH₃ | 3,5-dimethylisoxazol-4-yl (pos 3) | —CH₂— | —CH₂— |

-continued

Formula IC'

| R$_{1C}$ | R$_{2C}$ | R$_{3C}$ | R$_{4C}$ | Position, R$_{5C}$ | Position, R$_{6C}$ | L$_{1C}$ | L$_{2C}$ |
|---|---|---|---|---|---|---|---|
| Ph | H | H | Ph | H | 3, dimethylisoxazolyl | —CH$_2$— | —CH$_2$— |
| Ph | CH$_3$ | H | Ph | H | 3, dimethylisoxazolyl | —CH$_2$— | —CH$_2$— |
| Ph | H | H | Ph | 2, CH$_3$ | 3, dimethylisoxazolyl | —CH$_2$— | —CH$_2$— |
| Ph | CH$_3$ | H | Ph | 2, CH$_3$ | 3, dimethylisoxazolyl | —CH$_2$— | —CH$_2$— |
| 2-Cl-Ph | H | H | Ph | H | 3, dimethylisoxazolyl | —CH$_2$— | —CH$_2$— |
| 2-Cl-Ph | CH$_3$ | H | Ph | H | 3, dimethylisoxazolyl | —CH$_2$— | —CH$_2$— |
| 2-Cl-Ph | H | H | Ph | 2, CH$_3$ | 3, dimethylisoxazolyl | —CH$_2$— | —CH$_2$— |
| 2-Cl-Ph | CH$_3$ | H | Ph | 2, CH$_3$ | 3, dimethylisoxazolyl | —CH$_2$— | —CH$_2$— |

-continued

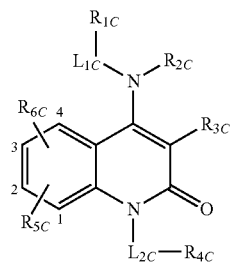

Formula IC'

| R$_{1C}$ | R$_{2C}$ | R$_{3C}$ | R$_{4C}$ | Position, R$_{5C}$ | Position, R$_{6C}$ | L$_{1C}$ | L$_{2C}$ |
|---|---|---|---|---|---|---|---|
| 2-Cl-phenyl | H | H | Ph | H | 3, 3,5-dimethylisoxazol-4-yl | —CH$_2$— | —CH$_2$— |
| 2-Cl-phenyl | CH$_3$ | H | Ph | H | 3, 3,5-dimethylisoxazol-4-yl | —CH$_2$— | —CH$_2$— |
| 2-Cl-phenyl | H | H | Ph | 2, CH$_3$ | 3, 3,5-dimethylisoxazol-4-yl | —CH$_2$— | —CH$_2$— |
| 2-Cl-phenyl | CH$_3$ | H | Ph | 2, CH$_3$ | 3, 3,5-dimethylisoxazol-4-yl | —CH$_2$— | —CH$_2$— |
| phenyl | H | H | Ph | H | 3, 3,5-dimethylisoxazol-4-yl | —CH$_2$— | —CH$_2$— |
| phenyl | CH$_3$ | CH$_3$ | Ph | H | 3, 3,5-dimethylisoxazol-4-yl | —CH$_2$— | —CH$_2$— |
| phenyl | H | CH$_3$ | Ph | 2, CH$_3$ | 3, 3,5-dimethylisoxazol-4-yl | —CH$_2$— | —CH$_2$— |
| phenyl | CH$_3$ | CH$_3$ | Ph | 2, CH$_3$ | 3, 3,5-dimethylisoxazol-4-yl | —CH$_2$— | —CH$_2$— |

-continued

Formula IC'

| R₁C | R₂C | R₃C | R₄C | Position, R₅C | Position, R₆C | L₁C | L₂C |
|---|---|---|---|---|---|---|---|
| Ph | H | CH₃ | Ph | H | 3, (3,5-dimethylisoxazol-4-yl) | —CH₂— | —CH₂— |
| Ph | CH₃ | CH₃ | Ph | H | 3, (3,5-dimethylisoxazol-4-yl) | —CH₂— | —CH₂— |
| Ph | H | CH₃ | Ph | 2, CH₃ | 3, (3,5-dimethylisoxazol-4-yl) | —CH₂— | —CH₂— |
| Ph | CH₃ | CH₃ | Ph | 2, CH₃ | 3, (3,5-dimethylisoxazol-4-yl) | —CH₂— | —CH₂— |
| 2-Cl-Ph | H | CH₃ | Ph | H | 3, (3,5-dimethylisoxazol-4-yl) | —CH₂— | —CH₂— |
| 2-Cl-Ph | CH₃ | CH₃ | Ph | H | 3, (3,5-dimethylisoxazol-4-yl) | —CH₂— | —CH₂— |
| 2-Cl-Ph | H | CH₃ | Ph | 2, CH₃ | 3, (3,5-dimethylisoxazol-4-yl) | —CH₂— | —CH₂— |
| 2-Cl-Ph | CH₃ | CH₃ | Ph | 2, CH₃ | 3, (3,5-dimethylisoxazol-4-yl) | —CH₂— | —CH₂— |

-continued

Formula IC'

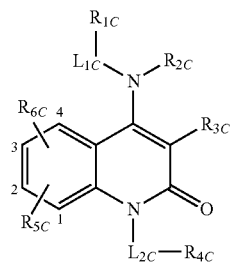

| R$_{1C}$ | R$_{2C}$ | R$_{3C}$ | R$_{4C}$ | Position, R$_{5C}$ | Position, R$_{6C}$ | L$_{1C}$ | L$_{2C}$ |
|---|---|---|---|---|---|---|---|
| 2-Cl-phenyl | H | CH$_3$ | Ph | H | 3, 3,5-dimethylisoxazol-4-yl | —CH$_2$— | —CH$_2$— |
| 2-Cl-phenyl | CH$_3$ | CH$_3$ | Ph | H | 3, 3,5-dimethylisoxazol-4-yl | —CH$_2$— | —CH$_2$— |
| 2-Cl-phenyl | H | CH$_3$ | Ph | 2, CH$_3$ | 3, 3,5-dimethylisoxazol-4-yl | —CH$_2$— | —CH$_2$— |
| 2-Cl-phenyl | CH$_3$ | CH$_3$ | Ph | 2, CH$_3$ | 3, 3,5-dimethylisoxazol-4-yl | —CH$_2$— | —CH$_2$— |
| pyridin-2-yl | H | H | Ph | 2, CH$_3$ | 3, 3,5-dimethylisoxazol-4-yl | —CH$_2$— | —CH$_2$— |
| pyridin-2-yl | CH$_3$ | H | Ph | 2, CH$_3$ | 3, 3,5-dimethylisoxazol-4-yl | —CH$_2$— | —CH$_2$— |
| pyridin-2-yl | H | H | H | H | 3, 3,5-dimethylisoxazol-4-yl | —CH$_2$— | —CH$_2$— |
| pyridin-2-yl | CH$_3$ | H | H | H | 3, 3,5-dimethylisoxazol-4-yl | —CH$_2$— | —CH$_2$— | or a pharmaceutically acceptable salt of any of the aforementioned.

13. The method of claim 1, wherein the compound is 4-(benzylamino)-6-(3,5-dimethylisoxazol-4-yl)-1-methylquinolin-2(1H)-one, or a pharmaceutically acceptable salt thereof.

14. The method of claim 1, wherein the compound of Formula IC is a compound of Formula IC', and is selected from the compounds defined according to the following Table:

Formula IC'

| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| phenyl | H | H | H | H | 3, (3,5-dimethylisoxazol-4-yl) | —CH$_2$— | bond |
| phenyl | CH$_3$ | H | H | H | 3, (3,5-dimethylisoxazol-4-yl) | —CH$_2$— | bond |
| phenyl | H | H | H | 2, CH$_3$ | 3, (3,5-dimethylisoxazol-4-yl) | —CH$_2$— | bond |
| phenyl | CH$_3$ | H | H | 2, CH$_3$ | 3, (3,5-dimethylisoxazol-4-yl) | —CH$_2$— | bond |
| 2-chlorophenyl | H | H | H | H | 3, (3,5-dimethylisoxazol-4-yl) | —CH$_2$— | bond |
| 2-chlorophenyl | CH$_3$ | H | H | H | 3, (3,5-dimethylisoxazol-4-yl) | —CH$_2$— | bond |
| 2-chlorophenyl | H | H | H | 2, CH$_3$ | 3, (3,5-dimethylisoxazol-4-yl) | —CH$_2$— | bond |

-continued
Formula IC'
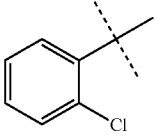
| R$_{1C}$ | R$_{2C}$ | R$_{3C}$ | R$_{4C}$ | Position, R$_{5C}$ | Position, R$_{6C}$ | L$_{1C}$ | L$_{2C}$ |
|---|---|---|---|---|---|---|---|
| 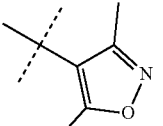 | CH$_3$ | H | H | 2, CH$_3$ | 3, 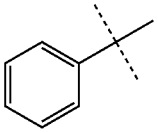 | —CH$_2$— | bond |
| 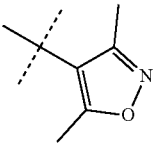 | H | H | H | H | 3, 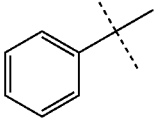 | —CH$_2$— | bond |
| 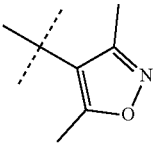 | CH$_3$ | CH$_3$ | H | H | 3, 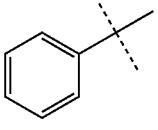 | —CH$_2$— | bond |
| 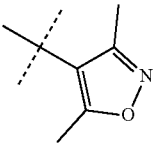 | H | CH$_3$ | H | 2, CH$_3$ | 3, 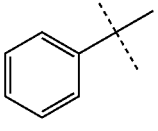 | —CH$_2$— | bond |
| 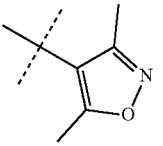 | CH$_3$ | CH$_3$ | H | 2, CH$_3$ | 3, 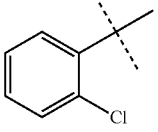 | —CH$_2$— | bond |
| 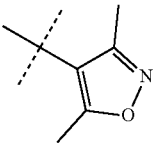 | H | CH$_3$ | H | H | 3, 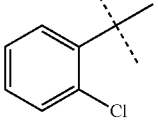 | —CH$_2$— | bond |
| 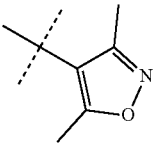 | CH$_3$ | CH$_3$ | H | H | 3, 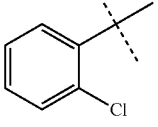 | —CH$_2$— | bond |
| 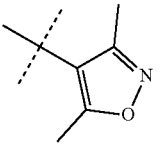 | H | CH$_3$ | H | 2, CH$_3$ | 3, | —CH$_2$— | bond |

-continued
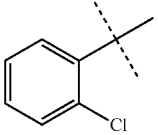
Formula IC'
| R$_{1C}$ | R$_{2C}$ | R$_{3C}$ | R$_{4C}$ | Position, R$_{5C}$ | Position, R$_{6C}$ | L$_{1C}$ | L$_{2C}$ |
|---|---|---|---|---|---|---|---|
| 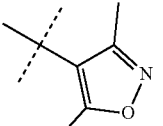 | CH$_3$ | CH$_3$ | H | 2, CH$_3$ | 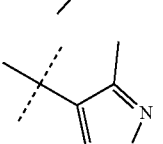 3, | —CH$_2$— | bond |
| 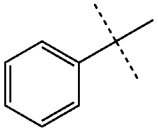 | H | H | H | 2, 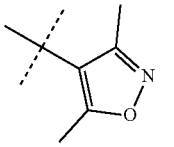 |  3, | —CH$_2$— | bond |
| 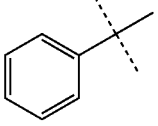 | CH$_3$ | H | H | 2, 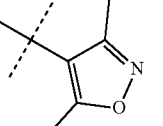 | 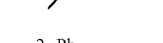 3, | —CH$_2$— | bond |
| 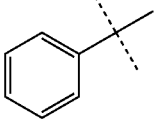 | H | H | H | 2, Ph | 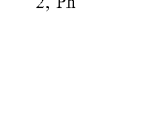 3, | —CH$_2$— | bond |
| 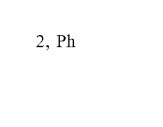 | CH$_3$ | H | H | 2, Ph | 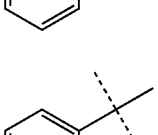 3, | —CH$_2$— | bond |
| 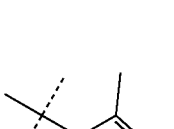 | H | H | H | 2, 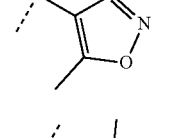 | 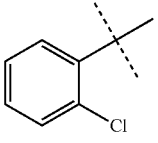 3, | —CH$_2$— | bond |
| 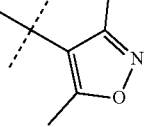 | CH$_3$ | H | H | 2, 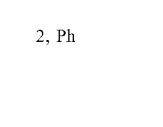 | 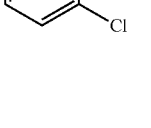 3, | —CH$_2$— | bond |
|  | H | H | H | 2, Ph |  3, | —CH$_2$— | bond |

-continued

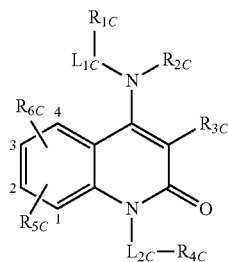

Formula IC'

| $R_{1C}$ | $R_{2C}$ | $R_{3C}$ | $R_{4C}$ | Position, $R_{5C}$ | Position, $R_{6C}$ | $L_{1C}$ | $L_{2C}$ |
|---|---|---|---|---|---|---|---|
| 2-Cl-phenyl | CH₃ | H | H | 2, Ph | 3, 3,5-dimethylisoxazol-4-yl | —CH₂— | bond |
| phenyl | H | H | H | 2, 3,5-dimethylisoxazol-4-yl | 3, 3,5-dimethylisoxazol-4-yl | —CH₂— | bond |
| phenyl | CH₃ | CH₃ | H | 2, 3,5-dimethylisoxazol-4-yl | 3, 3,5-dimethylisoxazol-4-yl | —CH₂— | bond |
| phenyl | H | CH₃ | H | 2, Ph | 3, 3,5-dimethylisoxazol-4-yl | —CH₂— | bond |
| phenyl | CH₃ | CH₃ | H | 2, Ph | 3, 3,5-dimethylisoxazol-4-yl | —CH₂— | bond |
| 2-Cl-phenyl | H | CH₃ | H | 2, 3,5-dimethylisoxazol-4-yl | 3, 3,5-dimethylisoxazol-4-yl | —CH₂— | bond |
| 2-Cl-phenyl | CH₃ | CH₃ | H | 2, 3,5-dimethylisoxazol-4-yl | 3, 3,5-dimethylisoxazol-4-yl | —CH₂— | bond |
| 2-Cl-phenyl | H | CH₃ | H | 2, Ph | 3, 3,5-dimethylisoxazol-4-yl | —CH₂— | bond |

-continued
Formula IC'
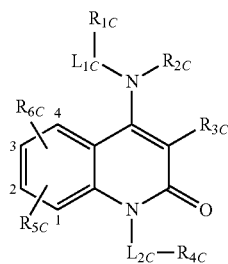
| R$_{1C}$ | R$_{2C}$ | R$_{3C}$ | R$_{4C}$ | Position, R$_{5C}$ | Position, R$_{6C}$ | L$_{1C}$ | L$_{2C}$ |
|---|---|---|---|---|---|---|---|
| 2-Cl-phenyl | CH$_3$ | CH$_3$ | H | 2, Ph | 3, 3,5-dimethylisoxazol-4-yl | —CH$_2$— | bond |
| 2-F-phenyl | H | H | H | H | 3, 3,5-dimethylisoxazol-4-yl | —CH$_2$— | bond |
| 2-Br-phenyl | H | H | H | H | 3, 3,5-dimethylisoxazol-4-yl | —CH$_2$— | bond |
| 2-OMe-phenyl | H | H | H | H | 3, 3,5-dimethylisoxazol-4-yl | —CH$_2$— | bond |
| 4-Cl-phenyl | H | H | H | H | 3, 3,5-dimethylisoxazol-4-yl | —CH$_2$— | bond | or a pharmaceutically acceptable salt of any of the aforementioned.

15. The method of claim 1, wherein the compound of Formula IC is a compound of Formula IC', and is selected from the compounds defined according to the following Table:

Formula IC'

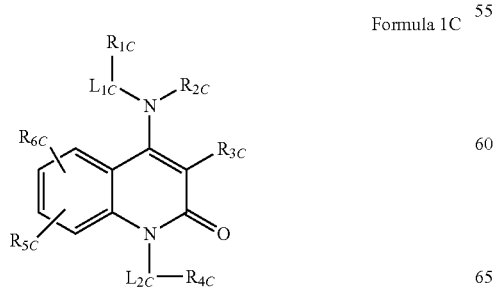

| $R_{1C}$—$L_{1C}$—N—$R_{2C}$ | $R_{3C}$ | —$L_{2C}$—$R_{4C}$ | $R_{5C}$ | Position, Position, $R_{6C}$ |
|---|---|---|---|---|
| morpholinyl | H | H | H | 3, isoxazolyl |
| piperidinyl | H | H | H | 3, isoxazolyl |
| ethylpiperazinyl | H | H | H | 3, isoxazolyl | or a pharmaceutically acceptable salt of any of the aforementioned.

16. The method of claim 1, wherein the compound is 4-(benzylamino)-6-(3,5-dimethylisoxazol-4-yl)quinolin-2 (1H)-one, or a pharmaceutically acceptable salt thereof.

17. A method of treating a disease or condition selected from fibrosis, inflammation, and lung cancer in a patient in need thereof, comprising administering to the patient a compound of Formula IC:

Formula IC or a pharmaceutically acceptable salt thereof, wherein:
$R_{6C}$ is

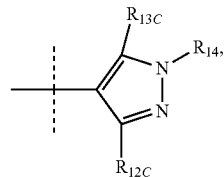

wherein $R_{12C}$ and $R_{13C}$ are independently selected from hydrogen, hydroxyl, sulfhydryl, alkoxy, thioalkoxy, alkyl and halogen, and $R_{14}$ is —H or $C_1$-$C_6$ alkyl optionally substituted with aryl, wherein the aryl is optionally substituted with one or more hydroxyl, sulfhydryl, CN, $CF_3$, $NO_2$, halo, alkyl, aryl, alkoxy, carboxyamido, sulfamido, or mono or dialkylsubstituted amine;

$L_{1C}$ is —$(CR_{10C}R_{11C})_{nC}$ wherein $R_{10C}$ and $R_{11C}$ are independently selected from hydrogen and alkyl; and nc is 0, 1, 2, or 3;

$L_{2C}$ is selected from the group consisting of —$(CR_{10C}R_{11C})_n$—, —$CON(R_{7C})$—, —$SO_2N(R_{7C})$—, —$NR_{7C}CON(R_{8C})$—, and —$OCON(R_{7C})$; and n is 0, 1, 2, or 3;

$R_{1C}$ is selected from alkyl, substituted or unsubstituted aryl, substituted or unsubstituted heteroaryl, substituted or unsubstituted cycloalkyl and substituted or unsubstituted heterocycloalkyl wherein the heteroaryl and heterocycloalkyl include one or more nitrogen, oxygen or sulfur as a heteroatom, and wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}$, $CONR_{7C}R_{8C}$, $NR_{7C}R_{8C}$, $NR_{7C}COR_{8C}$, $NR_{7C}SO_2R_{8C}$, $NR_{9C}CONR_{7C}R_{8C}$;

$R_{2C}$ is hydrogen or alkyl;

optionally, $R_{1C}$ and $R_{2C}$ are connected to make a substituted or unsubstituted cycloalkyl and substituted or unsubstituted heterocycloalkyl wherein the heteroatom is one or more nitrogen, oxygen or sulfur; wherein said substitutions are selected from hydrogen, hydroxyl, sulfhydryl, alkoxy, thioalkoxy, alkyl, halogen, CN, $CF_3$, $NO_2$, $COOR_7$, $NC(O)OR_{7C}$, $CONR_{7C}R_{8C}$, $NR_7R_{8C}$, $NR_{7C}COR_{8C}$, $NR_{7C}SO_2R_{8C}$, $NR_{7C}CONR_{8C}R_{9C}$;

$R_{3C}$ is hydrogen or alkyl;

$R_{4C}$ is selected from alkyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include one or more nitrogen, oxygen or sulfur as a heteroatom; wherein said substitutions are selected from hydrogen, hydroxyl, sulfhydryl, alkoxy, thioalkoxy, alkyl, halogen, CN, $CF_3$, $NO_2$, $COOR_{7C}$, $NC(O)OR_{7C}$, $CONR_{7C}R_{8C}$, $NR_{7C}R_{8C}$, $NR_{7C}COR_{8C}$, $NR_{7C}SO_2R_{8C}$, $NR_{7C}CONR_{8C}R_{9C}$;

$R_{5C}$ is selected from hydrogen, alkyl, substituted or unsubstituted aryl, substituted or unsubstituted heteroaryl, substituted or unsubstituted cycloalkyl and substituted or unsubstituted heterocycloalkyl, wherein the heterocycloalkyl and heteroaryl include one or more nitrogen, oxygen or sulfur as a heteroatom; wherein said substitutions are selected from hydrogen, hydroxyl, sulfhydryl, alkoxy, thioalkoxy, alkyl, halogen, CN, CF$_3$, NO$_2$, COOR$_{7C}$, NC(O)OR$_{7C}$C, CONR$_{7C}$R$_{8C}$, NR$_{7C}$R$_{8C}$, NR$_{7C}$COR$_{8C}$, NR$_{7C}$SO$_2$R$_{8C}$, NR$_{7C}$CONR$_{8C}$R$_{9C}$;

R$_{7C}$, R$_{8C}$ and R$_{9C}$ are each independently selected from hydrogen, alkyl, heteroalkyl, substituted or unsubstituted aryl, substituted or unsubstituted arylalkyl, substituted or unsubstituted heteroaryl, substituted or unsubstituted heteroarylalkyl, substituted or unsubstituted cycloalkyl, and substituted or unsubstituted heterocycloalkyl;

or optionally, R$_{7C}$ and R$_{8C}$, along with the atoms to which they are attached form a 4, 5, 6 or 7-member cyclic ring system, which is optionally substituted with one or more substituents selected from hydrogen, hydroxyl, sulfhydryl, alkoxy, thioalkoxy, alkyl and halogen.

18. The method of claim 17, wherein R$_{1C}$ is substituted or unsubstituted aryl, or substituted or unsubstituted heteroaryl.

19. The method of claim 17, wherein L$_{1C}$ is —(CR$_{10C}$R$_{11C}$)$_{nC}$, wherein R$_{10C}$ and R$_{11C}$ are each hydrogen or methyl and nc is 1 or 2.

20. The method of claim 17, wherein L$_{2C}$-R$_{4C}$ is methyl.

21. The method of claim 17, wherein R$_{2C}$ is H, R$_{3C}$ is H, and R$_{5C}$ is H.

22. The method of claim 1, wherein the disease or condition is lung cancer.

23. The method of claim 1, wherein the disease or condition is fibrosis.

24. The method of claim 23, wherein the fibrosis is idiopathic pulmonary fibrosis.

25. The method of claim 1, wherein the disease or condition is inflammation.

26. The method of claim 25, wherein the inflammation is associated with an inflammatory disease or condition selected from rheumatoid arthritis, osteoarthritis, acute gout, psoriasis, systemic lupus erythematosus, multiple sclerosis, inflammatory bowel disease, asthma, chronic obstructive airways disease, pneumonitis, myocarditis, pericarditis, myositis, eczema, dermatitis, alopecia, vitiligo, bullous skin diseases, nephritis, vasculitis, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes, and acute rejection of transplanted organ.

27. The method of claim 25, wherein the inflammation is associated with an inflammatory disease or condition selected from acute gout, giant cell arteritis, nephritis, vasculitis, glomerulonephritis, Wegener's granulomatosis, Polyarteritis nodosa, Behcet's disease, Kawasaki disease, and Takayasu's Arteritis.

28. The method of claim 25, wherein the inflammation is associated with sepsis, septic shock, endotoxaemia, systemic inflammatory response syndrome, multiorgan dysfunction syndrome, toxic shock syndrome, acute lung injury, adult respiratory distress syndrome, acute renal failure, fulminant hepatitis, acute pancreatitis, post-surgical syndromes, sarcoidosis, Herxheimer reactions, encephalitis, myelitis, meningitis, malaria, and SIRS associated with influenza, herpes zoster, herpes simplex, or coronavirus.

29. The method of claim 1, wherein the compound is administered by oral administration.

* * * * *